(12) United States Patent
George et al.

(10) Patent No.: US 12,396,892 B2
(45) Date of Patent: Aug. 26, 2025

(54) EXTERNAL EAR CANAL PRESSURE REGULATION DEVICE

(71) Applicant: NOCIRA, LLC, Tempe, AZ (US)

(72) Inventors: David George, Scottsdale, AZ (US); George Buckler, Phoenix, AZ (US); Timothy A. Crown, Tempe, AZ (US); David Brice Sullivan, Mechanicsburg, PA (US)

(73) Assignee: NOCIRA, LLC, Tempe, AZ (US)

( * ) Notice: Subject to any disclaimer, the term of this patent is extended or adjusted under 35 U.S.C. 154(b) by 845 days.

(21) Appl. No.: 17/401,733

(22) Filed: Aug. 13, 2021

(65) Prior Publication Data

US 2022/0202617 A1    Jun. 30, 2022

Related U.S. Application Data

(63) Continuation of application No. 14/900,607, filed as application No. PCT/US2014/044159 on Jun. 25, (Continued)

(51) Int. Cl.
*A61F 11/12* (2006.01)
*A61F 11/00* (2022.01)
(Continued)

(52) U.S. Cl.
CPC .............. *A61F 11/12* (2013.01); *A61F 11/00* (2013.01); *A61F 11/08* (2013.01); *A61H 9/0007* (2013.01);
(Continued)

(58) Field of Classification Search
CPC .. A61F 11/00; A61F 11/12; A61F 2250/0069; A61H 9/0071; A61H 21/00;
(Continued)

(56) References Cited

U.S. PATENT DOCUMENTS

| 787,443 A | 4/1905 | Godman et al. |
| 841,146 A | 1/1907 | Hasbrouck |

(Continued)

FOREIGN PATENT DOCUMENTS

| CA | 1136751 | 11/1982 |
| CA | 1222464 | 6/1987 |

(Continued)

OTHER PUBLICATIONS

Akerman, et al. Pearls and pitfalls in experimental in vivo models of migraine: Dural trigeminovascular nociception. Cephalalgia, 2013, 33 (8), pp. 557-592.
(Continued)

*Primary Examiner* — Rachel T Sippel
(74) *Attorney, Agent, or Firm* — Knobbe, Martens, Olson & Bear, LLP

(57) ABSTRACT

An external ear canal pressure regulation device including a fluid flow generator, an earpiece having an axial earpiece bore, and a valved conduit fluidicly coupled to the fluid flow generator and the axial earpiece bore, whereby the earpiece has a compliant earpiece external surface configured to sealably engage an external ear canal as a barrier between an external ear canal pressure and an ambient pressure.

20 Claims, 17 Drawing Sheets

Related U.S. Application Data 2014, now Pat. No. 11,090,194, which is a continuation-in-part of application No. 14/292,469, filed on May 30, 2014, now Pat. No. 10,251,790.

(60) Provisional application No. 61/983,865, filed on Apr. 24, 2014, provisional application No. 61/863,317, filed on Aug. 7, 2013, provisional application No. 61/841,111, filed on Jun. 28, 2013.

(51) Int. Cl.
*A61F 11/08* (2006.01)
*A61H 9/00* (2006.01)
*A61H 21/00* (2006.01)

(52) U.S. Cl.
CPC ........... *A61H 9/005* (2013.01); *A61H 9/0071* (2013.01); *A61H 21/00* (2013.01); *A61F 11/085* (2022.01); *A61F 2250/0013* (2013.01); *A61H 2201/0153* (2013.01); *A61H 2201/0207* (2013.01); *A61H 2201/0214* (2013.01); *A61H 2201/10* (2013.01); *A61H 2201/105* (2013.01); *A61H 2205/027* (2013.01)

(58) Field of Classification Search
CPC ............... A61H 23/02; A61H 23/04; A61H 2201/0153; A61H 2201/1207; A61H 2201/123–1246; A61H 2201/5071; A61H 2205/027; A61H 9/0007; A61M 13/003; A61M 2205/3344; A61M 2205/362; A61M 2210/0662–0675; H04R 1/42
See application file for complete search history.

(56) References Cited

U.S. PATENT DOCUMENTS

| | | |
|---|---|---|
| 853,645 A | 5/1907 | Meyer |
| 2,176,366 A | 10/1939 | Smith |
| 2,437,490 A | 3/1948 | Watson et al. |
| 2,570,675 A | 10/1951 | Morris |
| 2,652,048 A | 9/1953 | Joers |
| 3,757,769 A | 9/1973 | Arguimbau et al. |
| 3,872,559 A | 3/1975 | Leight |
| 4,002,161 A | 1/1977 | Klar et al. |
| 4,133,984 A | 1/1979 | Watson et al. |
| 4,160,449 A | 7/1979 | Wade |
| 4,206,756 A | 6/1980 | Grossan |
| 4,244,377 A | 1/1981 | Grams |
| 4,289,143 A | 9/1981 | Canavesio et al. |
| 4,325,386 A | 4/1982 | Katz |
| 4,349,083 A | 9/1982 | Bennett |
| 4,472,342 A | 9/1984 | Carr |
| 4,552,137 A | 11/1985 | Strauss |
| 4,594,058 A | 6/1986 | Fischell |
| 4,632,104 A | 12/1986 | Conrow |
| 4,667,676 A | 5/1987 | Guinta |
| 4,688,582 A | 8/1987 | Heller et al. |
| 4,754,748 A | 7/1988 | Antowski |
| 4,757,807 A | 7/1988 | Densert et al. |
| 4,775,370 A | 10/1988 | Berry |
| 4,809,708 A | 3/1989 | Geisler et al. |
| 4,896,380 A | 1/1990 | Kamitani |
| 4,896,679 A | 1/1990 | St. Pierre |
| 4,964,769 A | 10/1990 | Hass |
| 4,984,579 A | 1/1991 | Burgert et al. |
| 5,024,612 A * | 6/1991 | van den Honert ...... A61F 11/10 604/36 |
| 5,105,822 A | 4/1992 | Stevens et al. |
| 5,131,411 A | 7/1992 | Casali et al. |
| 5,228,431 A | 7/1993 | Giarretto |
| 5,241,967 A | 9/1993 | Yasushi et al. |
| 5,421,818 A | 6/1995 | Arenberg |
| 5,431,636 A | 7/1995 | Stangerup |
| 5,467,784 A | 11/1995 | Mobley et al. |
| 5,476,446 A | 12/1995 | Arenburg |
| 5,483,027 A | 1/1996 | Krause |
| 5,483,975 A | 1/1996 | Hirschebain |
| 5,488,961 A | 2/1996 | Adams |
| 5,631,965 A | 5/1997 | Chang et al. |
| 5,699,809 A | 12/1997 | Combs et al. |
| 5,740,258 A | 4/1998 | Goodwin-Johansson |
| 5,746,725 A | 5/1998 | Shalon et al. |
| 5,755,234 A | 5/1998 | Mobley et al. |
| 5,769,891 A | 6/1998 | Clayton |
| 5,776,179 A | 7/1998 | Ren et al. |
| 5,819,745 A | 10/1998 | Mobley et al. |
| 5,865,183 A | 2/1999 | Hirschebain |
| 5,868,682 A | 2/1999 | Combe et al. |
| 5,944,711 A | 8/1999 | Pender |
| 6,004,274 A | 12/1999 | Nolan et al. |
| 6,016,499 A | 1/2000 | Ferguson |
| 6,024,726 A | 2/2000 | Hill |
| 6,129,174 A | 10/2000 | Brown et al. |
| 6,139,507 A | 10/2000 | Jeng |
| 6,159,171 A | 12/2000 | Densert et al. |
| 6,186,959 B1 | 2/2001 | Canfield et al. |
| 6,258,067 B1 | 7/2001 | Hill |
| 6,296,652 B1 | 10/2001 | Qingmin |
| 6,359,993 B2 | 3/2002 | Birmhall |
| 6,430,443 B1 | 8/2002 | Karell |
| 6,511,437 B1 | 1/2003 | Nakamura et al. |
| 6,543,445 B1 | 4/2003 | Hopper |
| 6,592,512 B2 | 7/2003 | Stöckert et al. |
| 6,629,938 B1 | 10/2003 | Engvall et al. |
| 6,725,568 B2 | 4/2004 | Gronka |
| 6,748,275 B2 | 6/2004 | Lattner et al. |
| 6,800,062 B2 | 10/2004 | Epley |
| 6,820,717 B2 | 11/2004 | Fleming et al. |
| 6,878,128 B2 | 4/2005 | MacMahon et al. |
| 6,958,043 B2 | 10/2005 | Hissong |
| 6,981,569 B2 | 1/2006 | Stilp |
| 7,022,090 B1 | 4/2006 | Engvall et al. |
| 7,162,039 B1 | 1/2007 | Callahan |
| 7,179,238 B2 | 2/2007 | Hissong |
| 7,189,252 B2 | 3/2007 | Krueger |
| 7,268,466 B2 | 9/2007 | Rasmussen |
| 7,352,871 B1 | 4/2008 | Mozo |
| D570,457 S | 6/2008 | Brown |
| 7,613,519 B2 | 11/2009 | De Ridder |
| 7,766,858 B2 | 8/2010 | Franz et al. |
| 7,779,844 B2 | 8/2010 | Purcell et al. |
| 7,785,346 B2 | 8/2010 | Blumberg |
| 7,797,042 B2 | 9/2010 | Dietrich et al. |
| 7,833,282 B2 | 11/2010 | Mandpe |
| 7,892,180 B2 | 2/2011 | Epley |
| 7,959,597 B2 | 6/2011 | Baker et al. |
| 7,988,657 B2 | 8/2011 | Shapiro et al. |
| 8,020,563 B2 | 9/2011 | Pfanstiehl |
| 8,047,207 B2 | 11/2011 | Perez et al. |
| 8,052,693 B2 | 11/2011 | Shahoian |
| 8,122,892 B2 | 2/2012 | Johnson et al. |
| 8,142,373 B1 | 3/2012 | Riles |
| 8,199,919 B2 | 6/2012 | Goldstein et al. |
| 8,241,224 B2 | 8/2012 | Keefe |
| 8,249,285 B2 | 8/2012 | Killion et al. |
| 8,251,925 B2 | 8/2012 | Keady et al. |
| 8,262,717 B2 | 9/2012 | Rogers et al. |
| 8,267,983 B2 | 9/2012 | Rogers et al. |
| 8,267,984 B2 | 9/2012 | Rogers |
| 8,328,830 B1 | 12/2012 | Pandit |
| 8,398,562 B2 | 3/2013 | Keller |
| 8,414,521 B2 | 4/2013 | Baker et al. |
| 8,442,632 B2 | 5/2013 | Kullok et al. |
| 8,460,356 B2 | 6/2013 | Rogers et al. |
| 8,506,469 B2 | 8/2013 | Dietrich et al. |
| 8,515,552 B2 | 8/2013 | Englehart |
| 8,550,206 B2 | 10/2013 | Keady et al. |
| 8,568,348 B2 | 10/2013 | Vlodaver |
| 8,603,152 B2 | 12/2013 | Smith et al. |
| 8,625,833 B1 | 1/2014 | Armwood |
| 8,666,502 B2 | 3/2014 | Hartlep et al. |
| 8,688,239 B2 | 4/2014 | Hartlep et al. |

(56) References Cited

U.S. PATENT DOCUMENTS

| | | |
|---|---|---|
| 8,696,724 B2 | 4/2014 | Rogers |
| 8,858,430 B2 | 10/2014 | Oyadiran et al. |
| 8,963,914 B2 | 2/2015 | Rawat et al. |
| 9,039,639 B2 | 5/2015 | George et al. |
| 9,168,171 B2 | 10/2015 | Rogers |
| 9,186,277 B2 | 11/2015 | George et al. |
| 9,283,111 B2 | 3/2016 | Rogers et al. |
| 9,526,653 B2 | 12/2016 | Rogers et al. |
| 9,532,900 B2 | 1/2017 | Smith et al. |
| 9,579,247 B2 | 2/2017 | Juto et al. |
| 9,655,772 B2 | 5/2017 | Smith et al. |
| 9,744,074 B2 | 8/2017 | Rogers |
| 9,849,026 B2 | 12/2017 | Rogers et al. |
| 10,076,464 B2 | 9/2018 | George et al. |
| 10,251,790 B2 | 4/2019 | George et al. |
| 10,271,992 B2 | 4/2019 | Hayahi et al. |
| 10,278,868 B2 | 5/2019 | George et al. |
| 10,319,475 B1 | 6/2019 | Croan et al. |
| 10,376,695 B2 | 8/2019 | Ericco et al. |
| 10,760,566 B2 | 9/2020 | George et al. |
| 10,772,766 B2 | 9/2020 | Sullivan |
| 11,065,444 B2 | 7/2021 | Ericco et al. |
| 11,090,194 B2 | 8/2021 | George et al. |
| 11,096,828 B2 | 8/2021 | George et al. |
| 11,246,793 B2 | 2/2022 | George et al. |
| 11,859,606 B2 | 1/2024 | George et al. |
| 2001/0025191 A1 | 9/2001 | Montgomery |
| 2002/0069883 A1 | 6/2002 | Hirchenbain |
| 2003/0105450 A1 | 6/2003 | Dimick |
| 2003/0195588 A1 | 10/2003 | Fischell et al. |
| 2003/0220536 A1 | 11/2003 | Hissong |
| 2003/0220585 A1 | 11/2003 | Hissong |
| 2004/0097839 A1 | 5/2004 | Epley |
| 2004/0163882 A1 | 8/2004 | Fleming et al. |
| 2004/0225178 A1 | 11/2004 | Kriewall |
| 2005/0065585 A1 | 3/2005 | Salas |
| 2005/0165460 A1 | 7/2005 | Erfan |
| 2005/0209516 A1 | 9/2005 | Fraden |
| 2005/0267388 A1 | 12/2005 | Hanna |
| 2006/0100681 A1 | 5/2006 | Salas Carpizo |
| 2006/0197412 A1 | 9/2006 | Rasmussen |
| 2006/0253087 A1 | 11/2006 | Vlodaver et al. |
| 2006/0272650 A1 | 12/2006 | Hoogenakker et al. |
| 2007/0040454 A1 | 2/2007 | Freudenberger et al. |
| 2007/0112279 A1 | 5/2007 | Iseberg et al. |
| 2007/0250119 A1 | 10/2007 | Tyler et al. |
| 2007/0299362 A1 | 12/2007 | Epley et al. |
| 2008/0011308 A1 | 1/2008 | Fleming |
| 2008/0154183 A1 | 6/2008 | Baker et al. |
| 2008/0168775 A1 | 7/2008 | Windheim et al. |
| 2008/0208100 A1 | 8/2008 | Wolff |
| 2008/0212787 A1 | 9/2008 | Goldstein et al. |
| 2008/0220092 A1 | 9/2008 | Dipierro |
| 2008/0240942 A1 | 10/2008 | Heinrich et al. |
| 2008/0249439 A1 | 10/2008 | Tracey et al. |
| 2008/0264464 A1 | 10/2008 | Lee et al. |
| 2009/0012420 A1 | 1/2009 | Keller |
| 2009/0082831 A1 | 3/2009 | Paul et al. |
| 2009/0173353 A1 | 7/2009 | Pursell et al. |
| 2009/0182399 A1 | 7/2009 | Sylvestre |
| 2009/0228103 A1 | 9/2009 | Clayton |
| 2009/0293886 A1 | 12/2009 | Dedrick et al. |
| 2010/0002897 A1 | 1/2010 | Keady |
| 2010/0030131 A1 | 2/2010 | Morris et al. |
| 2010/0071707 A1 | 3/2010 | Wohl |
| 2010/0071708 A1 | 3/2010 | Lenhardt |
| 2010/0113991 A1 | 5/2010 | Wu |
| 2010/0179490 A1 | 7/2010 | Connelly et al. |
| 2010/0198282 A1 | 8/2010 | Rogers |
| 2010/0211142 A1 | 8/2010 | Rogers |
| 2010/0322454 A1 | 12/2010 | Ambrose et al. |
| 2011/0079227 A1 | 4/2011 | Turcot et al. |
| 2011/0097141 A1 | 4/2011 | Browm |
| 2011/0098551 A1 | 4/2011 | Zhang |
| 2011/0130786 A1 | 6/2011 | Clayton et al. |
| 2011/0172739 A1 | 7/2011 | Mann et al. |
| 2011/0184341 A1 | 7/2011 | Baker et al. |
| 2011/0224493 A1 | 9/2011 | Oyadiran et al. |
| 2011/0245902 A1 | 10/2011 | Katz |
| 2011/0301572 A1 | 12/2011 | Vlodaver et al. |
| 2011/0313481 A1* | 12/2011 | De Vos ............... A61N 1/0546 607/42 |
| 2012/0046607 A1 | 2/2012 | Syk |
| 2012/0203309 A1 | 8/2012 | Englehart |
| 2012/0265093 A1 | 10/2012 | Allen et al. |
| 2012/0296268 A1 | 11/2012 | Vlodavaer et al. |
| 2012/0302859 A1 | 11/2012 | Keefe |
| 2012/0310077 A1 | 12/2012 | Rogers |
| 2012/0310313 A1 | 12/2012 | Rogers et al. |
| 2012/0318605 A1 | 12/2012 | Brown |
| 2013/0123889 A1 | 5/2013 | Katz et al. |
| 2013/0136285 A1 | 5/2013 | Naumann |
| 2013/0152949 A1 | 6/2013 | Simon |
| 2013/0177179 A1 | 7/2013 | Ambrose et al. |
| 2013/0183173 A1 | 7/2013 | Kohli et al. |
| 2013/0282070 A1 | 10/2013 | Cowan et al. |
| 2013/0303953 A1 | 11/2013 | Lattner |
| 2013/0304103 A1 | 11/2013 | Burres |
| 2013/0310907 A1 | 11/2013 | Rogers et al. |
| 2013/0324932 A1 | 12/2013 | Cogley |
| 2013/0331823 A1 | 12/2013 | Askem et al. |
| 2014/0069442 A1 | 3/2014 | Lewis et al. |
| 2014/0088671 A1 | 3/2014 | Rogers et al. |
| 2014/0243941 A1 | 8/2014 | Rogers et al. |
| 2014/0249608 A1 | 9/2014 | Rogers |
| 2014/0275827 A1 | 9/2014 | Gill et al. |
| 2014/0309718 A1 | 10/2014 | Smith et al. |
| 2014/0334652 A1 | 11/2014 | Gebert |
| 2014/0344740 A1 | 11/2014 | Kaula et al. |
| 2014/0365175 A1 | 12/2014 | Packer et al. |
| 2015/0005661 A1 | 1/2015 | Trammell |
| 2015/0141879 A1 | 5/2015 | Harper et al. |
| 2015/0320591 A1 | 11/2015 | Smith et al. |
| 2015/0320592 A1 | 11/2015 | Black et al. |
| 2015/0324544 A1 | 11/2015 | Maslowski et al. |
| 2015/0328413 A1 | 11/2015 | Cain |
| 2015/0335466 A1 | 11/2015 | Schöggler |
| 2015/0374538 A1 | 12/2015 | Rogers |
| 2016/0067099 A1 | 3/2016 | Hayashi |
| 2016/0166203 A1 | 6/2016 | Goldstein |
| 2016/0279435 A1 | 9/2016 | Hyde et al. |
| 2016/0346117 A1 | 12/2016 | Rogers et al. |
| 2016/0378945 A1 | 12/2016 | Mian et al. |
| 2017/0105876 A1 | 4/2017 | O'Connell, Sr. et al. |
| 2017/0109988 A1 | 4/2017 | O'Connell, Sr. et al. |
| 2017/0135854 A1 | 5/2017 | Rogers et al. |
| 2017/0235889 A1 | 8/2017 | Main et al. |
| 2018/0008457 A1 | 1/2018 | Smith et al. |
| 2018/0106244 A1 | 4/2018 | Wang et al. |
| 2018/0125748 A1 | 5/2018 | Goldenberg et al. |
| 2020/0121544 A1 | 4/2020 | George et al. |
| 2021/0222684 A1 | 7/2021 | George et al. |
| 2021/0228414 A1 | 7/2021 | George et al. |
| 2021/0330928 A1 | 10/2021 | George et al. |
| 2022/0226158 A1 | 7/2022 | George et al. |
| 2022/0370286 A1 | 11/2022 | George et al. |
| 2024/0271609 A1 | 8/2024 | George |

FOREIGN PATENT DOCUMENTS

| | | |
|---|---|---|
| CA | 1241152 | 8/1988 |
| CA | 2003452 | 6/1990 |
| CA | 2275057 | 10/1999 |
| CA | 2 337 076 | 1/2000 |
| CA | 2429560 | 1/2004 |
| CN | 2075517 U | 4/1991 |
| CN | 2418864 | 2/2001 |
| CN | 1308513 A | 8/2001 |
| CN | 2530645 | 1/2003 |
| CN | 2721057 Y | 8/2005 |
| CN | 1791370 A | 6/2006 |
| CN | 2912525 | 6/2007 |
| CN | 200945215 Y | 9/2007 |
| CN | 201143258 | 11/2008 |

(56) References Cited

FOREIGN PATENT DOCUMENTS

| | | |
|---|---|---|
| CN | 201164541 | 12/2008 |
| CN | 101668497 | 3/2010 |
| CN | 201505220 U | 6/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |
| CN | 102892392 A | 1/2013 |
| CN | 102986250 | 3/2013 |
| DE | 37 83 917 T2 | 8/1993 |
| DE | 102011008802 | 7/2012 |
| EP | 0 026 247 | 4/1981 |
| EP | 0 400 900 | 12/1990 |
| EP | 1 027 863 | 8/2000 |
| EP | 2 207 366 | 7/2010 |
| EP | 2 990 017 | 3/2016 |
| FR | 2 605 516 A1 | 4/1988 |
| FR | 2 779 944 | 12/1999 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | S 57-188245 | 11/1982 |
| JP | H 02-220650 | 9/1990 |
| JP | H 07-111987 | 5/1995 |
| JP | H 11-514898 | 12/1999 |
| JP | 2002-519150 | 7/2002 |
| JP | 2003-018359 | 1/2003 |
| JP | 2006-345903 | 12/2006 |
| JP | 2009-022699 | 2/2009 |
| JP | 2010-233643 | 10/2010 |
| JP | 2010-535542 | 11/2010 |
| JP | 2011-217986 | 11/2011 |
| JP | 2013-068448 | 4/2013 |
| JP | 2013-102784 | 5/2013 |
| JP | 2020-44371 | 3/2020 |
| KR | 10-1273296 | 6/2013 |
| MX | PA03005598 | 10/2004 |
| MX | 2010014470 | 2/2011 |
| MX | 2011006854 | 8/2011 |
| MX | 2012007726 | 8/2012 |
| RU | 90 333 U1 | 1/2010 |
| WO | WO 1986/01399 | 3/1986 |
| WO | WO 1994/22372 | 10/1994 |
| WO | WO 1996/23293 | 8/1996 |
| WO | WO 1997/23178 | 7/1997 |
| WO | WO 2000/001331 | 1/2000 |
| WO | WO 2000/001346 | 1/2000 |
| WO | WO 2000/010484 | 3/2000 |
| WO | WO 2000/010627 | 3/2000 |
| WO | WO 2000/010848 | 3/2000 |
| WO | WO 2001/19244 | 3/2001 |
| WO | WO 2003/075761 | 9/2003 |
| WO | WO 2004/064672 | 8/2004 |
| WO | WO 2004/100844 | 11/2004 |
| WO | WO 2006/003910 | 1/2006 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2010/005899 | 1/2010 |
| WO | WO 2010/016925 | 2/2010 |
| WO | WO 2010/085196 | 7/2010 |
| WO | WO 2011/075573 | 6/2011 |
| WO | WO 2011/075574 | 6/2011 |
| WO | WO 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/175257 | 10/2014 |
| WO | WO 2014/210457 | 12/2014 |
| WO | WO 2015/009421 | 1/2015 |
| WO | WO 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| WO | WO 2017/079783 | 5/2017 |
| WO | WO 2017/197150 | 11/2017 |
| WO | WO 2018/106839 | 6/2018 |
| WO | WO 2018/157143 | 8/2018 |
| WO | WO 2019/246456 | 12/2019 |

OTHER PUBLICATIONS

Baguley et al. Does caloric vestibular stimulation modulate tinnitus? Neuroscience Letters, Mar. 2011, 492(1), pp. 52-54.

Baier, et al.: "Vestibular-Evoked Myogenic Potentials in "Vestibular Migraine" and Meniere's Disease," Ann. N.Y. Acad. Sci., May 2009, 1164, pp. 324-327.

Becker: Weather and migraine: Can so many patients be wrong? Cephalalgia, Mar. 2011, 31(4), pp. 387-390.

Berthold Langguth, Verena Hund, Volker Busch, et al., "Tinnitus and Headache," BioMed Research International, vol. 2015, Article ID 797416, 7 pages, 2015. https://doi.org/10.115/2015/797416 (Year: 2015) in 7 pages.

Bolay et al.,: "Does Low Atmospheric Pressure Independently Trigger Migraine?" Headache, Oct. 2011, 51(9), pp. 1426-1430.

Breathometer. Breathometer—The World's First Smartphone Breathalyzer. Website, http://www.breathometer.com, originally downloaded Jun. 19, 2014, 8 total pages.

Cadwell. Sierra Wave. Website, http://www.cadwell.com, originally downloaded Feb. 27, 2014, 1 page.

Cathcart, et al., "Pain sensitivity mediates the relationship between stress and headache intensity in chronic tension-type headache", Nov. 2012 (Year: 2012) in 5 pages.

Cranial Nerves—Wikipedia, axes, printed Aug. 16, 2019 in 12 pages.

Croley, Christen, "Mechanicsburg doctor develops new migraine therapy," The Sentinel, Nov. 9. 2012.

DaSilva, et al.: "tdCS-Induced Analgesia and Electrical Fields in Pain-Related Neural Networks in Chronic Migraine," The Journal of Head and Face Pain, Sep. 2012, 52, pp. 1283-1295.

Dirckx et al. Human tympanic membrane deformation under static pressure. Hearing Research, Jan. 1991, 51(1), pp. 93-106.

Doherty, Colleen. "The Link Between Migraines and Tinnitus". Verywell Health, Nov. 23, 2019, https://www.verywellhealth.com/link-between-migraines-and-tinnitus-4077631#citation-10 (Year: 2019) in 4 pages.

Facebook. Zōk: The first migraine and headache solution, Webpage, https://www.facebook.com, originally downloaded May 18, 2017, 10 pages total.

Fasold et al. Human Vestibular Cortex as Identified with Caloric Stimulation in Functional Magnetic Resonance Imaging. Neuroimage, Nov. 2002, 17(3), pp. 1384-1393.

Ferrotec. Thermal Solutions. Website: http://thermal.ferrotec.com, originally downloaded Feb. 27, 2014, 1 page.

(56) References Cited

OTHER PUBLICATIONS

Ferrotec. Thermoelectric Technical Reference—Installation of Thermoelectric Modules. Website, http://thermal.ferrotec.com, originally downloaded May 21, 2014, 4 total pages.
Ferrotec. Thermoelectric Technical Reference—Introduction to Thermoelectric Cooling. Website, http://forrotec.com, originally downloaded Feb. 27, 2014, 2 total pages.
Frangos E, Ellrich J, Komisaruk B. Non-invasive access to the vagus nerve central projections via electrical stimulation of the external ear: fMRI evidence in humans. Brain Stimul. Dec. 6, 2014. 8(3), 624-636 in 13 pages.
George et al. Safety and usability factors in development of a novel, automated treatment device for acute migraine. Biomedical sciences instrumentation. Biomedical sciences instrumentation, Jan. 2017, 53, pp. 398-403.
Hahn: "Let Me Blow in Your Ear, for Migraine Treatment, of Course," Smile Columbia Dentistry, https://www.tmjtreatments.com, originally downloaded Apr. 25, 2016, 2 pages total.
Hu et al. Burden of migraine in the United States: disability and economic costs. Arch. Intern. Med., Apr. 1999, 159, pp. 813-818.
Janetta Neurovascular Compress in Cranial Nerve and Systemic Disease. Ann Surg, Oct. 1980, 192 (4), pp. 518-524.
Job et al. Cortical Representation of Tympanic Membrane Movements due to Pressure Variation: An ±MRI Study Human Brain Mapping, May 2011, 32(5), pp. 744-749.
Kanzara T, Hall A, Virk J, Leung B, Singh A. Clinical anatomy of the tympanic nerve: A review. World J Otorhinolaryngol. Nov. 2014; 4(4), 17-22 in 8 pages.
Kickstarter. Zok: The first headache product that solves migraines and headaches. Website, https://www.funded.today, originally downloaded May 18, 2017, 3 pages total.
Kiyokawa J., Yamaguchi K, Okada R, Maehara T, Akita K. Origin, course and distribution of the nerves to the posterosuperior wall of the external acoustic meatus. Anat Sci Int. Mar. 2014; 89(4), 238-245.
Klingner et al.: "Components of vestibular cortical function," Behavioral Brain Research, Jan. 2013, 236(1), pp. 194-199.
Kolev. How caloric vestibular irrigation influences migraine attacks. Cephalalgia. Aug. 1990, vol. 10 issue 4, pp. 167-169 (abstract only).
Lifting the Burden. The Global Campaign Against Headache. Website, http://www.I-t-b.org, originally downloaded Feb. 27, 2014, 1 page.
Liszewski: Ear Pressure Equalizer. Website, http://www.ohgizmo.com, originally downloaded Dec. 18, 2013, 1 page.
Long Island news12.com. Long Island Naturally: Migraines. Website video, http://longisland.news12.com/multimedia/long-island-naturally-migraines-1.6501113, Nov. 26, 2013, 3 total pages.
Mayr: The Origins of Feedback Control. M.I.T. Press, 1970.
McGeoch et al. Vestibular stimulation can relieve central pain of spinal origin. Spinal Cord, Nov. 2008, 46(11), pp. 756-757.
Medscape. Peripheral Nerve Stimulator-Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 total pages.
Medtronic. Restore Life's Balance with Meniett Therapy. The Meniett Device for Meniere's Disease. On-line article, http://www.medtronic.com, originally downloaded Mar. 13, 2015, 2 total pages.
Meng et al. Migraine Prevention with a Supraorbital Transcutaneous Stimulator: A Randomized Controlled Trial. Neurology, Sep. 2013, 81, pp. 1102-1103.
Minen. Tinnitus and Headache. American Migraine Foundation, website, downloaded Feb. 8, 2017, 3 pages total.
Mosqueria et al. Vagus Nerve Stimulation in Patients with Migraine. Rev Neurol, 2013, 57(2), English Abstract.
Nagai et al. Encapsulated nerve corpuscles in the human tympanic membrane. Archives of Otorhinolaryngology, 1989, 246(3), pp. 169-172.

New York Health Solutions. Migraine Headaches. Website, http://www.nyhealthsolutions.com, originally downloaded May 23, 2014, 2 pages.
Nihashi et al. Representation of the ear in human primary somatosensory cortex. Neuroimage, Feb. 2001, 13(2), pp. 295-304 (abstract only).
Olesen et al. Emerging Migraine treatments and drug targets. Trends in Pharmacological Sciences, 2011, 32(6), pp. 352-359.
Pederson et al. Neurostimulation in cluster headache: A review of current progress. Cephalalgia, 2013, 33(14), pp. 1179-1193.
Pietrobon, Migraine: new molecular mechanism. Neuroscientist. Aug. 2005, vol. 11, Issue 4, pp. 373-386 (abstract only).
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.
Saunders R, Tympanic membrane sensation. Brain. 1985, 108, 378-404 in 18 pages.
Schoenen et al. Migraine prevention with a supraorbital transcutaneous stimulator. Neurology, 2013, 80(8), pp. 697-704.
Schulman. Breath-Holding, Head Pressure, and Hot Water: An Effective Treatment for Migraine Headache. Headache, Nov.-Dec. 2002, 42(10), pp. 1048-1050.
Scion Neurostim. Therapeutic Neuromodulation via Caloric Vestibular Stimulation. Thermoneuromodulation (TNM). Slides for presentation, dated Sep. 2015, 12 pages total.
Sheftell, F, Steiner, TJ, Thhomas, H. Harry Potter and the Curse of Headache. Headache: The Journal of Head and Face Pain. Jun. 2007, vol. 47, Issue 6, pp. 911-916 (abstract only) in 1 page.
Shevel, "Headaches and tinnitus: correlation found", May 2008 (Year: 2006).
Silberstein et al.: "Botulinum Toxin Type A as a Migraine Preventive Treatment," The Journal of Head and Face Pain, Jun. 2000, 40, pp. 445-450.
Smartproducts. Series 100—Cartridge Specialty Check Valves and Pressure Relief Valves. Online catalog, www.smartproducts,com, originally downloaded Mar. 28, 2014, 2 total.
Stender, DR., "Easing Migraine Symptoms with a Simple Puff of Air into the Ear," Pasadena Pain Management, http://www.pasadenapainmanagement.com, downloaded Apr. 25, 2016, 5 pages total.
Stovnver, LJ, et al. The global burden of headache: a documentation of headache prevalence and disability worldwide. Cephalalgia, 2007. vol. 27, pp. 193-210.
Sullivan: "Ear Insufflation as a Novel Therapy Which Produces Rapid Relief of Migraine Headache—a Case Study," Funct Neurol Rehabil Egon 2013; vol. 3, Issue 1, pp. 93-107. Published on Jun. 7, 2013. Received on Jan. 2, 2013. Revised Jan. 28, 2013. Accepted Feb. 15, 2013.
Sullivan: "Ear Insufflation Produces Rapid and Significant Relief of Trigeminal Neuralgia," Funct Neurol Rehabil Egon 2013; vol. 3, Issue 4, pp. 1-6. Published on May 26, 2014. Received on Jun. 21, 2013. Revised Dec. 24, 2013. Accepted Jan. 12, 2014.
Tekdemir I, Aslan A, Elhan A., A clinico-anatomic study of the auricular branch of the vagus nerve and Arnold's ear-cough reflex. Surg Radiol Anat. 1998. 20(4), 253-257 in 5 pages.
Tekdemir I, Aslan A, Tuccar E, He C, Elhan A, Deda H. An anatomical study of the tympanic branch of the glossopharyngeal nerve (nerve of Jacobson). Ann Anat. Aug. 1998; 180(4): 349-52 in 4 pages.
Transcript of News Story, Aug. 22, 2013, video available at: https://www.facebook.com/178787878873891/videos/10201196245541704/.
"New Migraine Therapy," Aug. 22, 2013, video available at https://www.facebook.com/178787878873891/videos/10201196245541704/.

(56) References Cited

OTHER PUBLICATIONS

Transcript of News Story, Nov. 13, 2013, video available at: https://www.facebook.com/178787878873891/videos/treatment-for-migraines-and-trigeminal-neuralgia/10201781732138503/.
"Revolutionary Pain Therapy," Nov. 13, 2013, video available at https://www.facebook.com/178787878873891/videos/treatment-for-migraines-and-trigeminal-neuralgia/10201781732138503/.
Transcript of News Story, Jul. 7, 2014, video available at: https://www.facebook.com/178787878873891/videos/681870651898942/.
"New Therapy for Migraines," Jul. 7, 2014, video available at https://www.facebook.com/178787878873891/videos/treatment-for-migraines-and-trigeminal-neuralgia/10201781732138503/.
Transcript of Webinar, Apr. 10, 2013, video available at: https://www.anymeeting.com/WebConference/RecordingDefault.aspx?c_psrid=ED57DC868548.
A novel application to resolve migraine headaches—A Functionalvideo available at: https://www.anymeeting.com/WebConference/RecordingDefault.aspx?c_psrid=ED57DC868548.
Ultimate Ears. Ultimate Ears Custom In-Ear Monitors. Website, http://pro.ultimateears.com, originally downloaded Feb. 27, 2014, 3 total pages.
Von Korff, et al., "Assessing headaches severity. New Directions", Jul. 1994 (Year: 1994).
Westone. Occupational Earpieces. Website, http://www.westone.com, originally downloaded Feb. 27, 2014, 2 total pages.
Widemar L, Hellstrom S, Schultzberg M, Stenfors LE. Autonomic innervation of the tympanic membrane. An immunocytochemical and histofluorescence study. Acta Otolaryngol. Jul.-Aug. 1985;100(1-2):58:65 in 9 pages.
Wikipedia. Microcurrent electrical neuromuscular stimulator. Website, http://en.wikipedia.org, originally downloaded Feb. 27, 2014, 3 total pages.
Wikipedia. Somatosensory evoked potential. Website, http://en.wikipedia.org, originally downloaded Feb. 27, 2014, 5 pages total.
Wikipedia. Transcutaneous electrical nerve stimulation. Website, http://en.wikipedia.org, originally downloaded Feb. 27, 2014, 5 pages total.
World Health Organization. Headache disorders. Website, http://www.who.int, originally downloaded Feb. 27, 2014, 4 total pages.
Chinese Patent Application No. 201480042665.7; Office Action dated Jan. 22, 2017, 26 pages total.
Chinese Office Action, dated Sep. 4, 2017, re CN Application No. 201480042665.7, 6 pages total.
European Supplemental Search Report dated Dec. 8, 2016, re EP Application No. 14826160.5, 8 pages total.
European Office Action, dated Nov. 24, 2017, re EP Application No. 14816984.0, 6 pages total.
International Search Report and Written Opinion in co-pending application No. PCT/US2018/019981, mailed Jun. 27, 2018 in 15 pages.
New Zealand Patent Application No. 713887; Office Action mailed Feb. 20, 2017, 9 pages total.
PCT International Patent Cooperation Treaty Patent Application No. PCT/US14/044159, filed Jun. 25, 2014.
PCT International Patent Application No. PCT/US2014/0066191; Written Opinion of the International Searching Authority mailed Feb. 26, 2015, 7 pages total.
U.S. Appl. No. 61/841,111, filed Jun. 28, 2013.
U.S. Appl. No. 14/292,469, filed May 30, 2014.
U.S. Appl. No. 61/863,317, filed Aug. 7, 2013.
U.S. Appl. No. 61/905,616, filed Nov. 18, 2013.
U.S. Appl. No. 61/983,865, filed Apr. 24, 2014.
U.S. Appl. No. 07/286,744, filed Dec. 19, 1988.
Teixido, Michael: "Migraine—More than a Headache," Dec. 15, 1999, ENT and Allergy of Delaware (Year: 1999).
U.S. Appl. No. 18/949,671, filed Nov. 15, 2024.

* cited by examiner

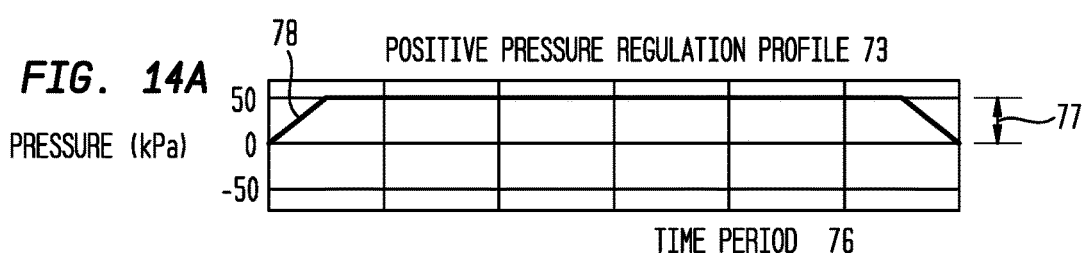
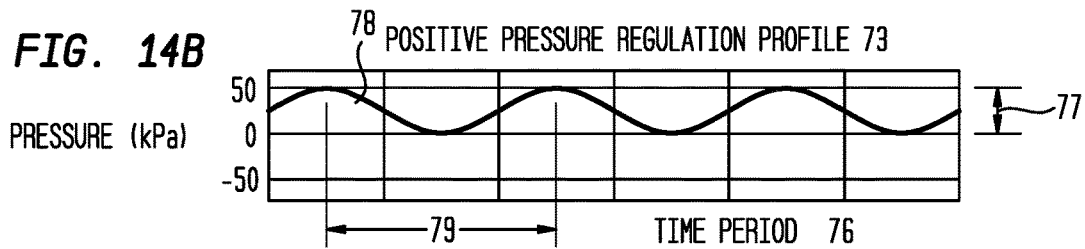
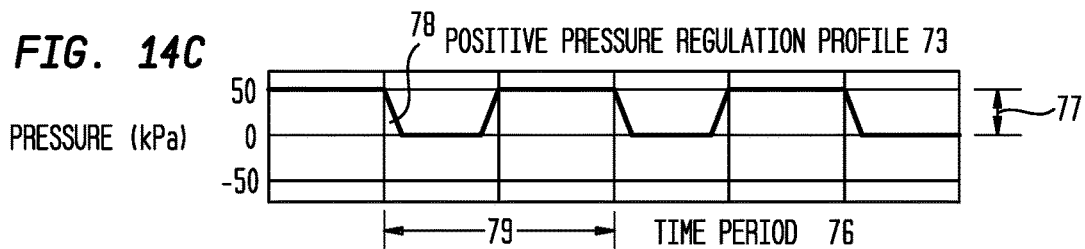
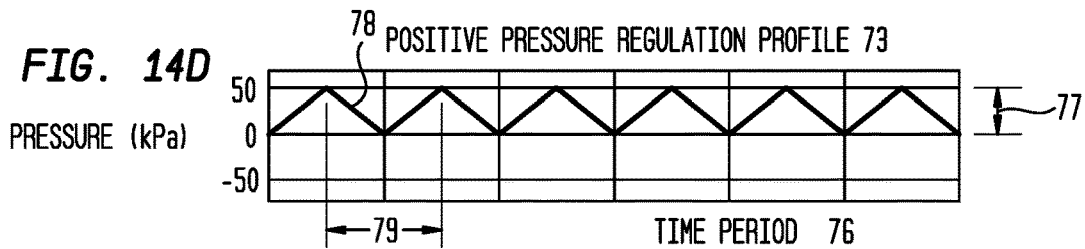
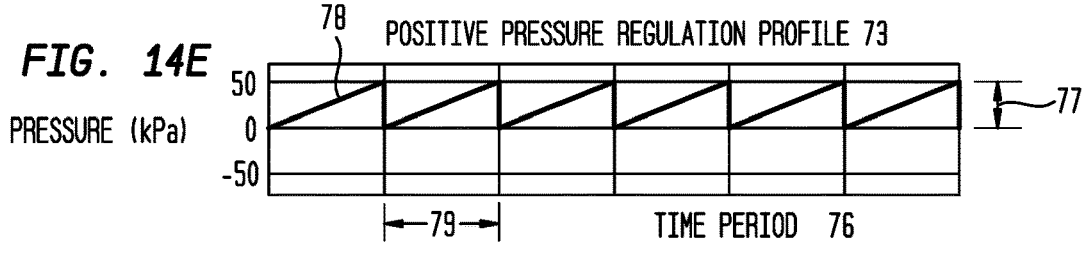
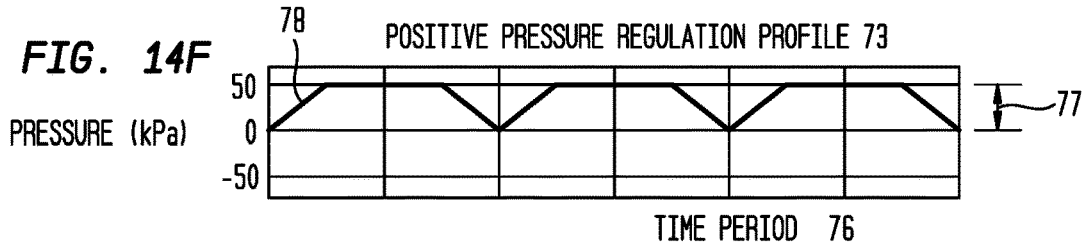
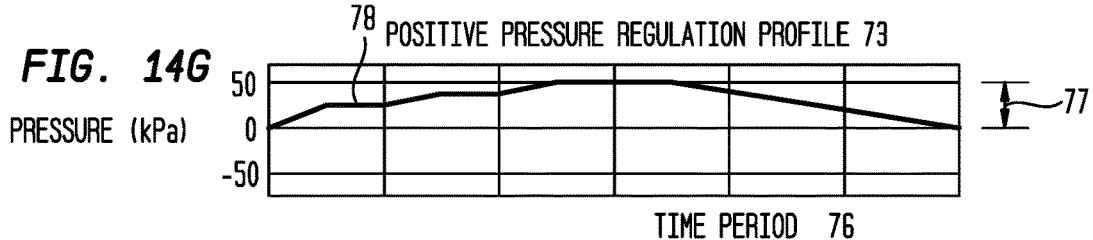

EXTERNAL EAR CANAL PRESSURE REGULATION DEVICE

This application is a continuation of U.S. Non-Provisional patent application Ser. No. 14/900,607, filed Dec. 21, 2015, now U.S. Pat. No. 11,090,194, issued Aug. 17, 2021, which is a national phase application of International Patent Cooperation Treaty Patent Application No. PCT/US2014/044159, filed on Jun. 25, 2014, which is a continuation-in-part of U.S. Non-Provisional patent application Ser. No. 14/292,469, filed May 30, 2014, now U.S. Pat. No. 10,251,790, issued Apr. 9, 2019, and claims the benefit of U.S. Provisional Patent Application No. 61/983,865, filed Apr. 24, 2014, U.S. Provisional Patent Application No. 61/863,317, filed Aug. 7, 2013, and U.S. Provisional Patent Application No. 61/841,111, filed Jun. 28, 2013, each of which is hereby incorporated by reference herein.

I. BACKGROUND OF THE INVENTION

Pain or discomfort associated with a disorder, including neurologically-mediated disorders such as craniofacial pain syndromes or headache syndromes, may negatively impact the quality of life of the sufferer. In addition to the burden upon the individual, chronic neurological conditions may be a significant strain upon family members, employers, and the healthcare system.

Regarding migraine headaches, concomitant symptoms such as pain, nausea, aura, photophobia, dysesthesias, dizziness, vertigo, and dysequilibrium may represent a significant burden to the population. Epidemiological studies indicate that, in the United States, approximately 18% of women and 6% of men experience frequent migraine headaches and 2% of the general population suffer from chronic migraine headaches. Additionally, persons suffering with chronic migraine headaches or other headaches of similar severity and disability may be at a significantly greater risk for depression and attempted suicide. Thus, it is prudent for clinicians and researchers to continue searching for effective devices and methods to alleviate the symptoms associated with these disorders or to treat the disorders.

Standard pharmaceutical therapies for migraine headaches may generally be prescribed to prevent pain or to relieve pain. The various agents which fall under these two broad categories may exhibit a wide range of effectiveness and also incur varying degrees of side effects. From the perspective of economics, the expense of these medications may be a major source of financial burden on the consumer. Moreover, advanced interventions such as botulinum toxin injections, nerve blockades, neurosurgical alterations, and implanted electrical stimulators may significantly increase costs associated with treatment, while subjecting patients to potential changes in their anatomy and physiology, with no guarantee of complete or permanent symptomatic relief or disorder resolution.

There is a burgeoning field of understanding and applications within the neurosciences which seek to affect positive physiological changes in the nervous system through non-pharmaceutical and non-surgical applications. This field of 'functional neurology' views the human nervous system as a receptor driven system, which may be activated and stimulated in specific ways to produce adaptive, long-term changes through the process of neuroplasticity. This approach to neurorehabilitation utilizes, but not necessarily exclusively includes, various forms and patterns of receptor activation or deactivation to promote positive neurophysiological adaptations within the central nervous system, including the brain, brainstem, and spinal cord, which may promote physiological function of associated tissues, organs, and systems.

There would be a substantial advantage in providing a device or methods which can generate one or more stimuli which can alleviate one or more symptoms associated with a disorder, such as craniofacial pain syndromes or headache syndromes, or treat one or more disorders.

II. DISCLOSURE OF THE INVENTION

A broad object of particular embodiments of the invention can be to provide an external ear canal pressure regulation device including a fluid flow generator which generates a fluid flow; a valved conduit fluidicly coupled to the fluid flow generator, the valved conduit having a first fluid flow conduit interruptible by one or more valves to unidirectionally regulate the fluid flow in the first fluid flow conduit; and an earpiece having an axial earpiece bore which communicates between an earpiece first end and an earpiece second end, the axial earpiece bore fluidicly coupled to the valved conduit opposite the fluid flow generator, the earpiece having a compliant earpiece external surface configured to sealably engage an external ear canal as a barrier between an external ear canal pressure and an ambient pressure.

Another broad object of particular embodiments of the invention can be to provide an external ear canal pressure regulation device having the valved conduit coupled in a first configuration with the fluid flow generator and the earpiece to unidirectionally regulate the fluid flow in a first direction in the first fluid flow conduit such that the fluid flow can egress from the axial earpiece bore of the earpiece toward the external ear canal, thereby achieving an external ear canal pressure greater than the ambient pressure.

Another broad object of particular embodiments of the invention can be to provide an external ear canal pressure regulation device having the valved conduit coupled in a second configuration with the fluid flow generator and the earpiece to unidirectionally regulate the fluid flow in a second direction in the first fluid flow conduit such that the fluid flow can ingress to the axial earpiece bore of the earpiece from the external ear canal, thereby achieving an external ear canal pressure lesser than the ambient pressure.

Another broad object of particular embodiments of the invention can be to provide an external ear canal pressure regulation device having a valved conduit which removably couples to the fluid flow generator and the earpiece. The valved conduit can be coupled in the first configuration with the fluid flow generator and the earpiece to unidirectionally regulate the fluid flow in the first direction in the first fluid flow conduit. Additionally, the valved conduit can be coupled in the second configuration with the fluid flow generator and the earpiece to unidirectionally regulate the fluid flow in the second direction in the first fluid flow conduit.

Another broad object of particular embodiments of the invention can be to provide a method of producing an external ear canal pressure regulation device, the method including providing a fluid flow generator capable of generating a fluid flow; providing a valved conduit capable of being fluidicly coupled to the fluid flow generator, the valved conduit having a first fluid flow conduit; providing one or more valves capable of interrupting the first fluid flow conduit to unidirectionally regulate the fluid flow in the first fluid flow conduit; and providing an axial earpiece bore, which communicates between an earpiece first end and an earpiece second end of an earpiece, the axial earpiece bore capable of being fluidicly coupled to the valved conduit opposite the fluid flow generator, the earpiece having a compliant earpiece external surface configured to sealably engage an external ear canal as a barrier between an external ear canal pressure and an ambient pressure.

Another broad object of particular embodiments of the invention can be to provide a method of using an external ear canal pressure regulation device, the method including obtaining the external ear canal pressure regulation device including a fluid flow generator which generates a fluid flow; a valved conduit fluidicly coupled to the fluid flow generator, the valved conduit having a first fluid flow conduit interruptible by one or more valves to unidirectionally regulate the fluid flow in the first fluid flow conduit; and an earpiece having an axial earpiece bore which communicates between an earpiece first end and an earpiece second end, the axial earpiece bore fluidicly coupled to the valved conduit opposite the fluid flow generator, the earpiece having a compliant earpiece external surface configured to sealably engage an external ear canal as a barrier between an external ear canal pressure and an ambient pressure; sealably engaging the earpiece external surface of the earpiece with the external ear canal; generating the fluid flow between the fluid flow generator and the axial earpiece bore; and regulating an external ear canal pressure differential between the external ear canal pressure and the ambient pressure.

Naturally, further objects of the invention are disclosed throughout other areas of the specification, drawings, and claims.

III. BRIEF DESCRIPTION OF THE DRAWINGS

Figure 11A:
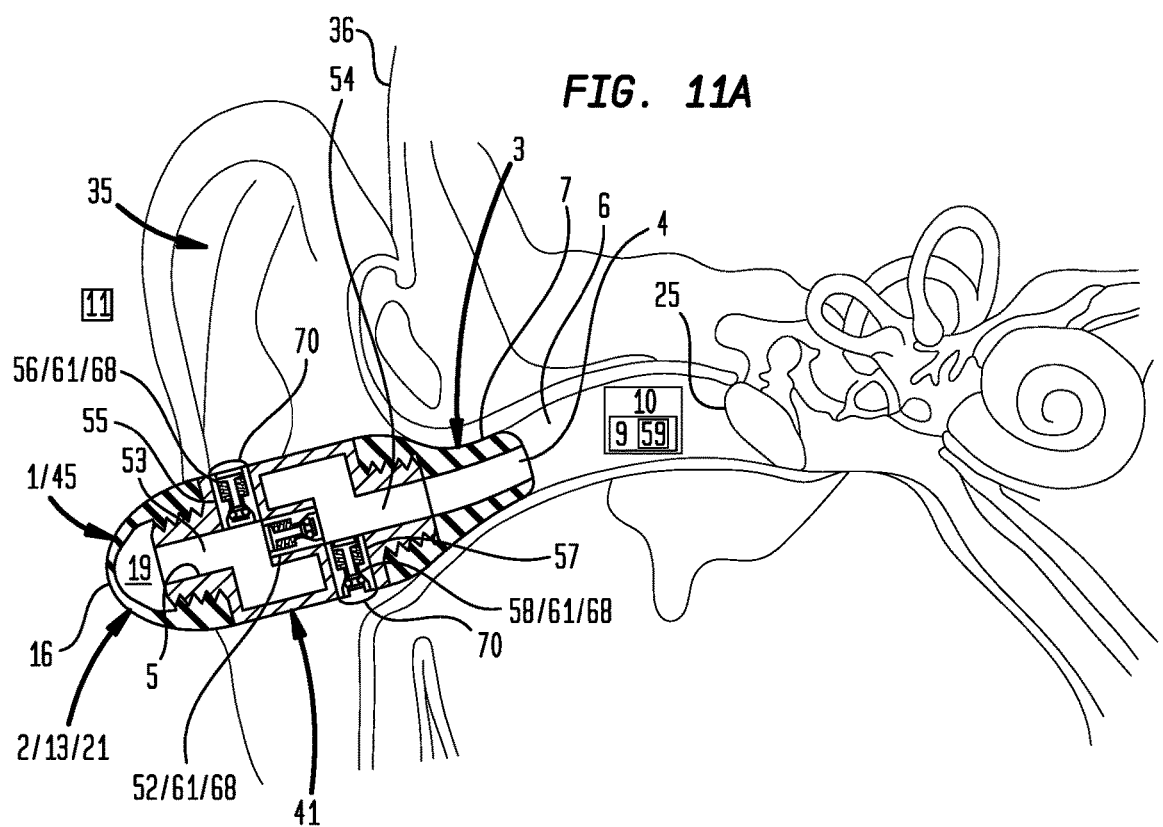
FIG. 11A is an illustration of a first configuration of the external ear canal pressure regulation device having the earpiece external surface sealably engaged with the external ear canal.
Figure 11B:
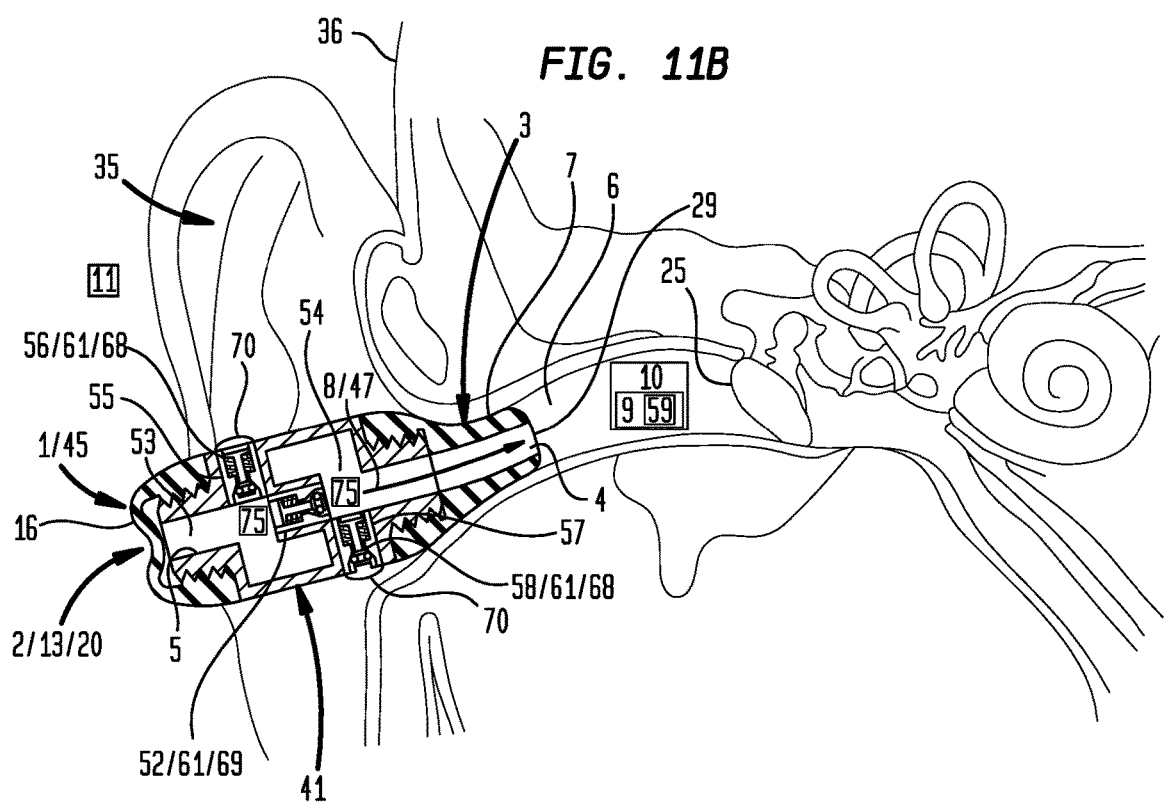

FIG. 11B is an illustration of the first configuration of the external ear canal pressure regulation device having the earpiece external surface sealably engaged with the external ear canal and having the fluid flow generator in a deformed condition generating sufficient pressure within the valved conduit to place a first valve in the open condition to provide a fluid flow toward the external ear canal to achieve an external ear canal pressure greater than the ambient pressure.

Figure 11C:
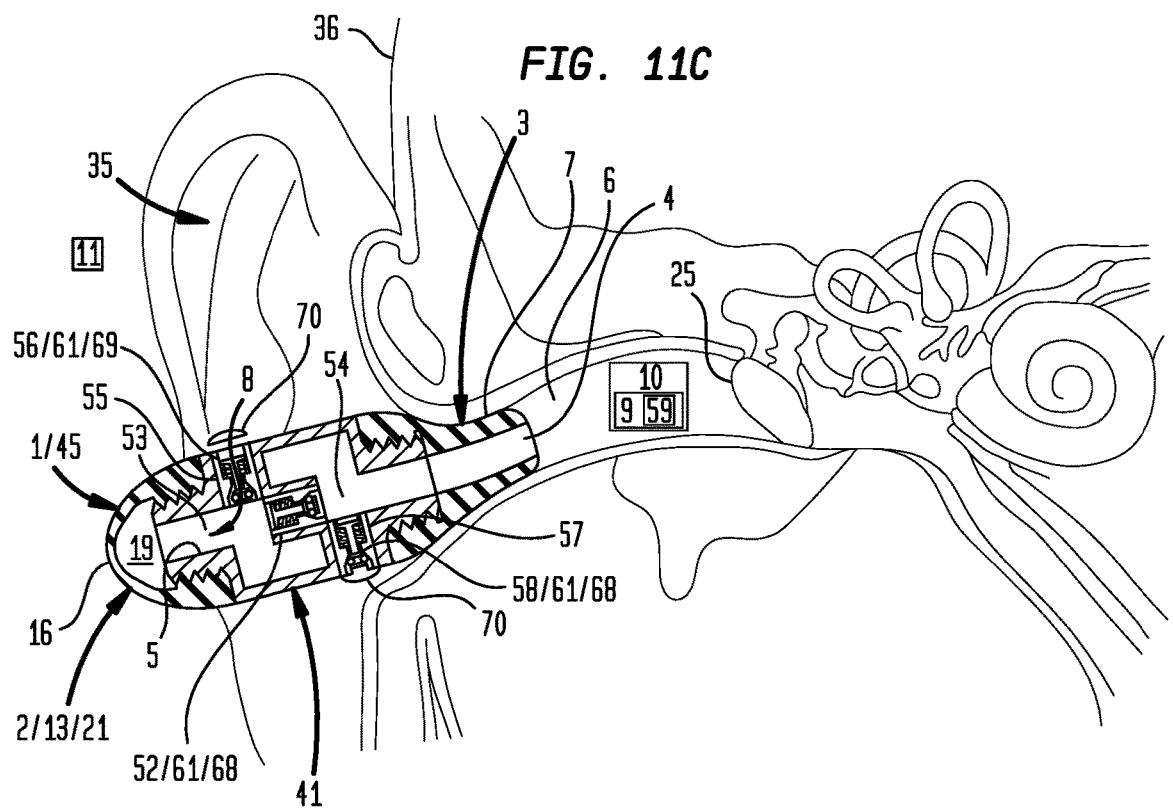

FIG. 11C is an illustration of the first configuration of the external ear canal pressure regulation device having the earpiece external surface sealably engaged with the external ear canal and having the fluid flow generator returning toward a non-deformed condition which generates sufficient pressure to place the first valve in the closed condition to maintain the external ear canal pressure and place a second valve in an open condition to generate a fluid flow from the ambient pressure toward the fluid flow generator.

Figure 11D:
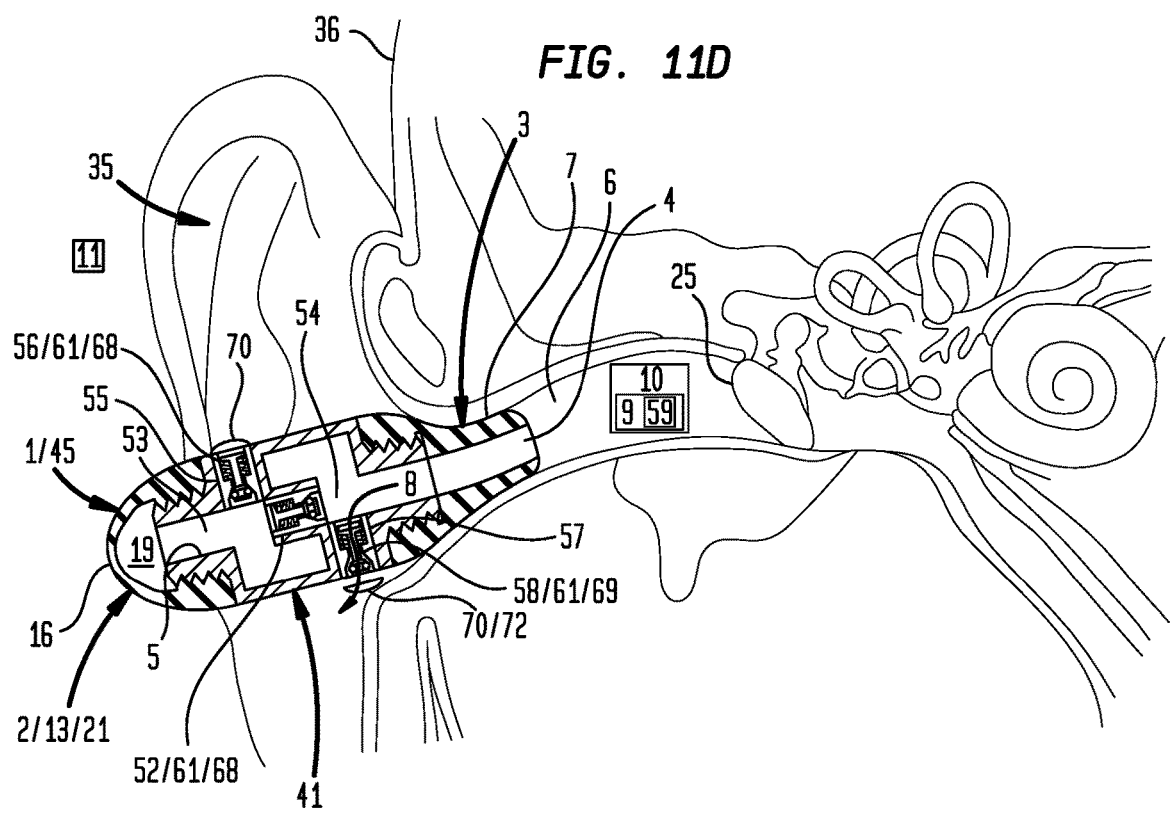

FIG. 11D is an illustration of the first configuration of the external ear canal pressure regulation device having the earpiece external surface sealably engaged with the external ear canal and having a third valve manually placed in the open condition by operation of a pressure relief element to generate a fluid flow from the external ear canal toward the ambient pressure to return the external ear canal pressure toward the ambient pressure.

Figure 12A:
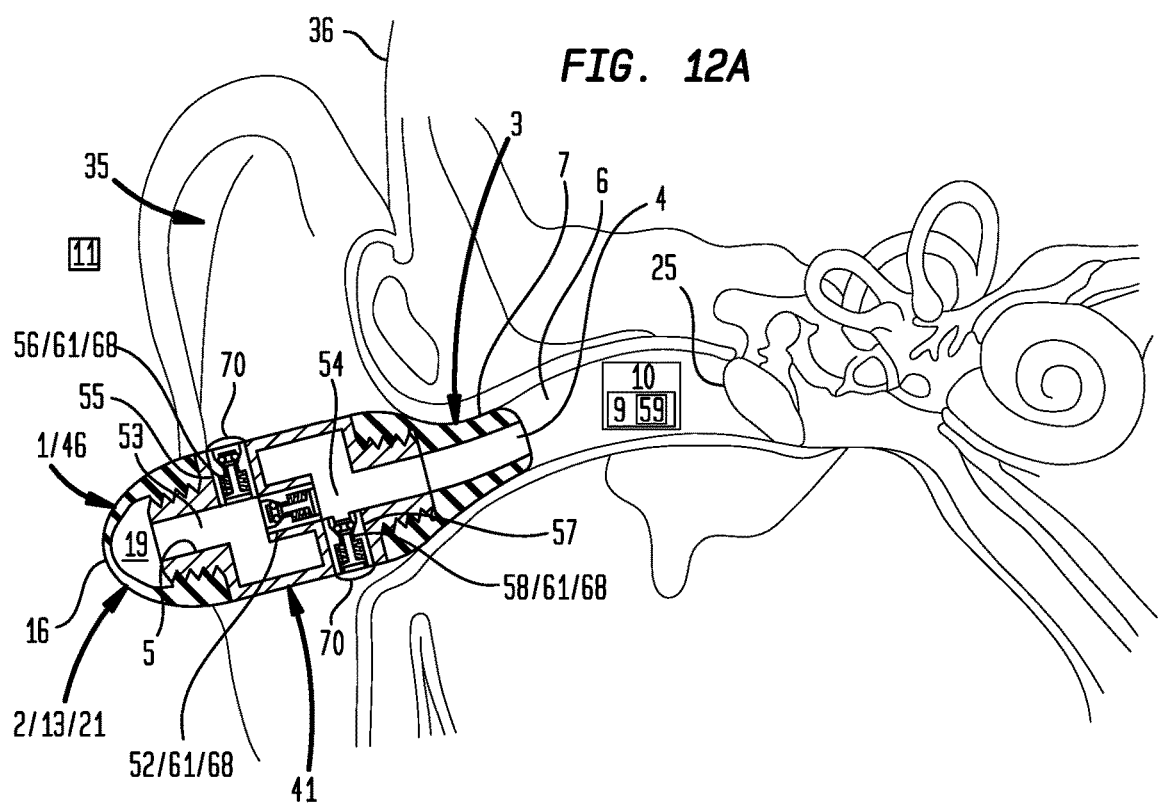

FIG. 12A is an illustration of a second configuration of the external ear canal pressure regulation device having the earpiece external surface sealably engaged with the external ear canal.

Figure 12B:
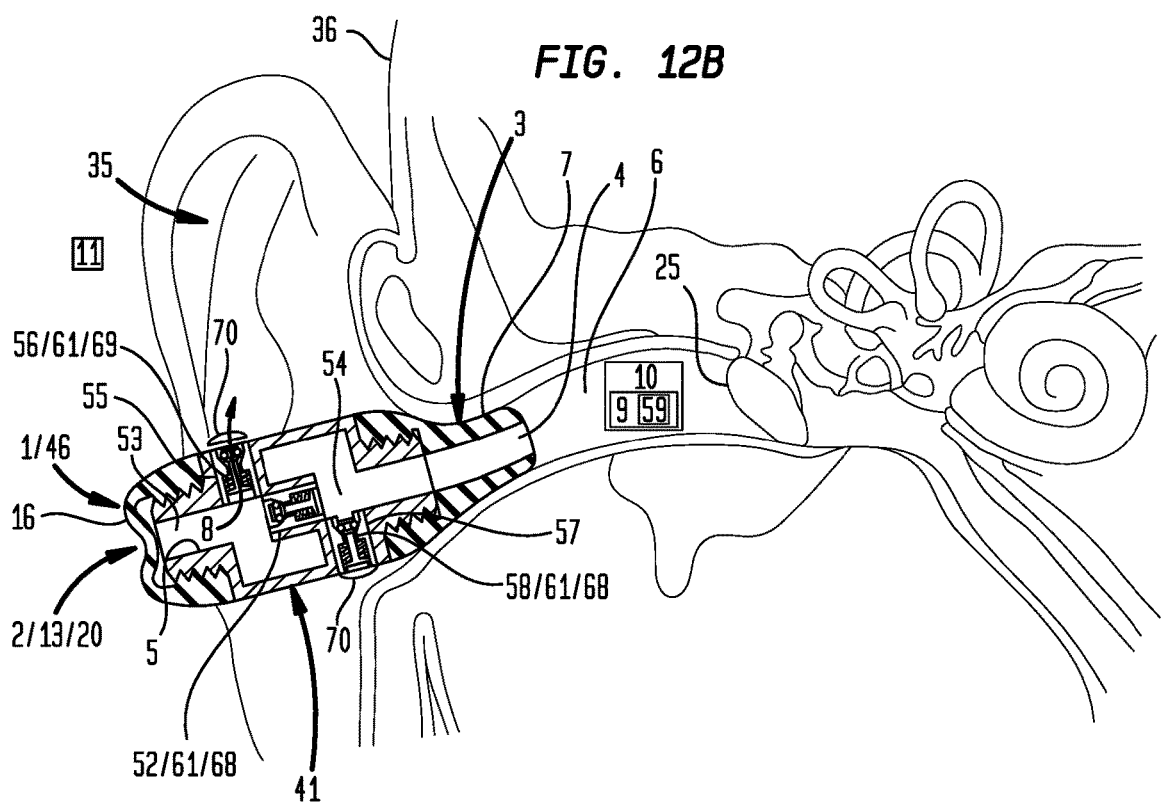

FIG. 12B is an illustration of the second configuration of the external ear canal pressure regulation device having the earpiece external surface sealably engaged with the external ear canal and having the fluid flow generator in a deformed condition generating sufficient pressure within the valved conduit to place the second valve in the open condition to provide a fluid flow toward the ambient pressure while maintaining the external ear canal pressure at the ambient pressure.

Figure 12C:
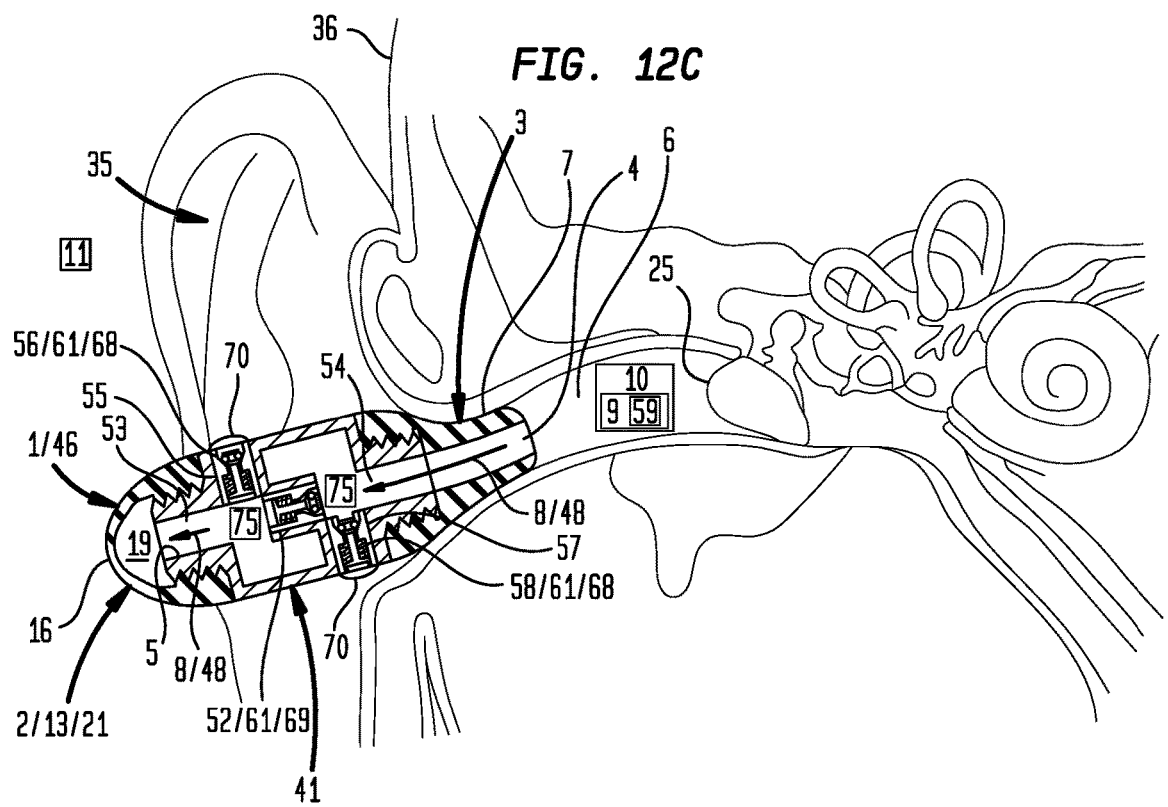

FIG. 12C is an illustration of the second configuration of the external ear canal pressure regulation device having the earpiece external surface sealably engaged with the external ear canal and having the fluid flow generator returning toward a non-deformed condition which generates sufficient pressure to place the first valve in the open condition and the second valve in the closed condition to generate a fluid flow from the external ear canal toward the fluid flow generator to generate an external ear canal pressure less than the ambient pressure.

Figure 12D:
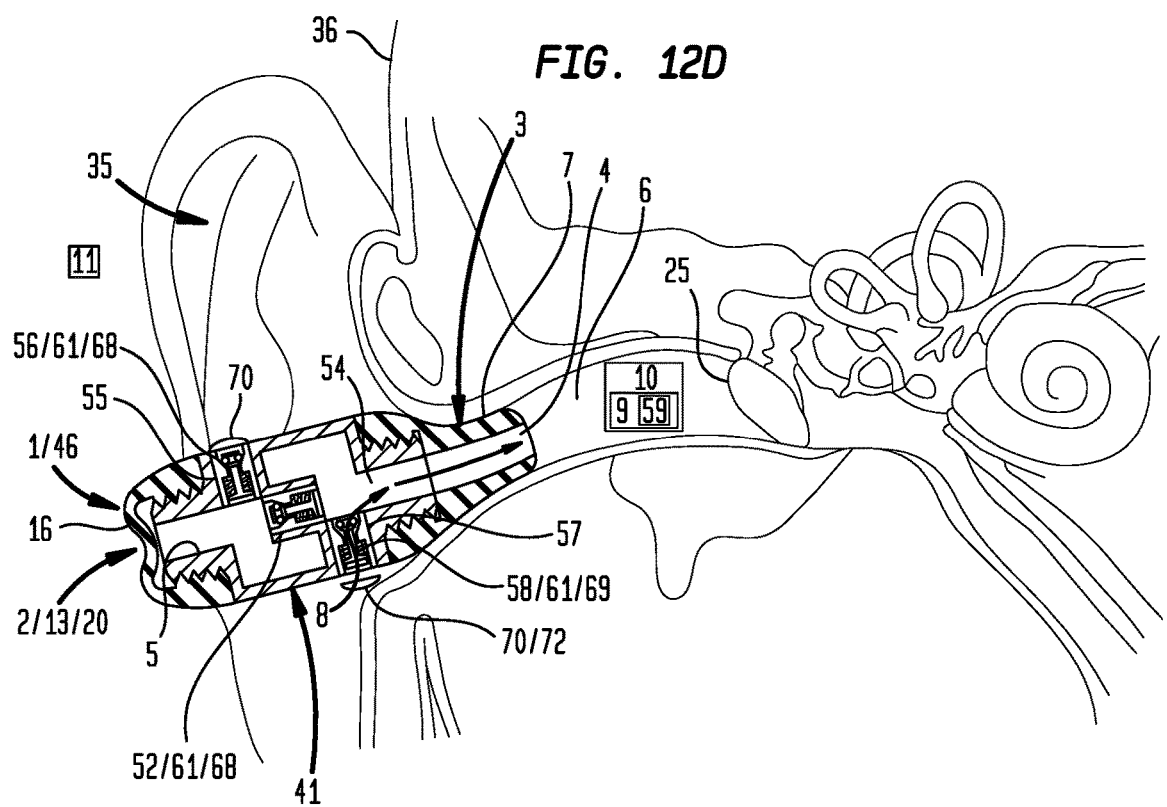

FIG. 12D is an illustration of the second configuration of the external ear canal pressure regulation device having the earpiece external surface sealably engaged with the external ear canal and having a third valve manually placed in the open condition by operation of a pressure relief element to generate a fluid flow from the ambient pressure toward the external ear canal to return the external ear canal pressure toward the ambient pressure.

Figure 13A:
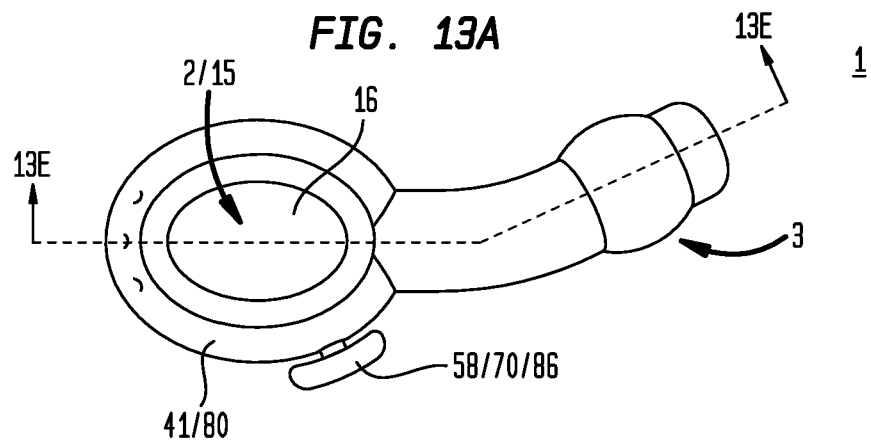

FIG. 13A is a top view of a particular embodiment of an external ear canal pressure regulation device.

Figure 13B:
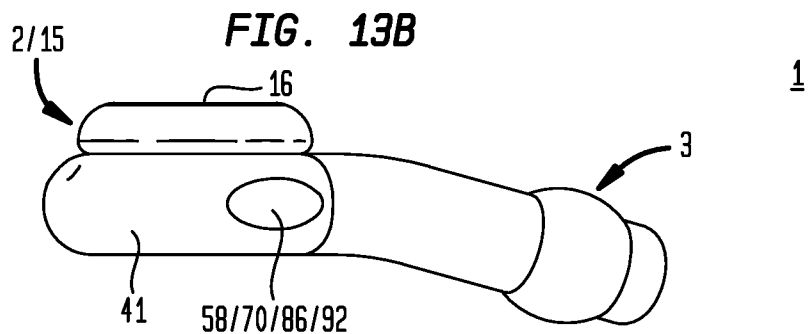

FIG. 13B is a side view of a particular embodiment of an external ear canal pressure regulation device.

Figure 13C:
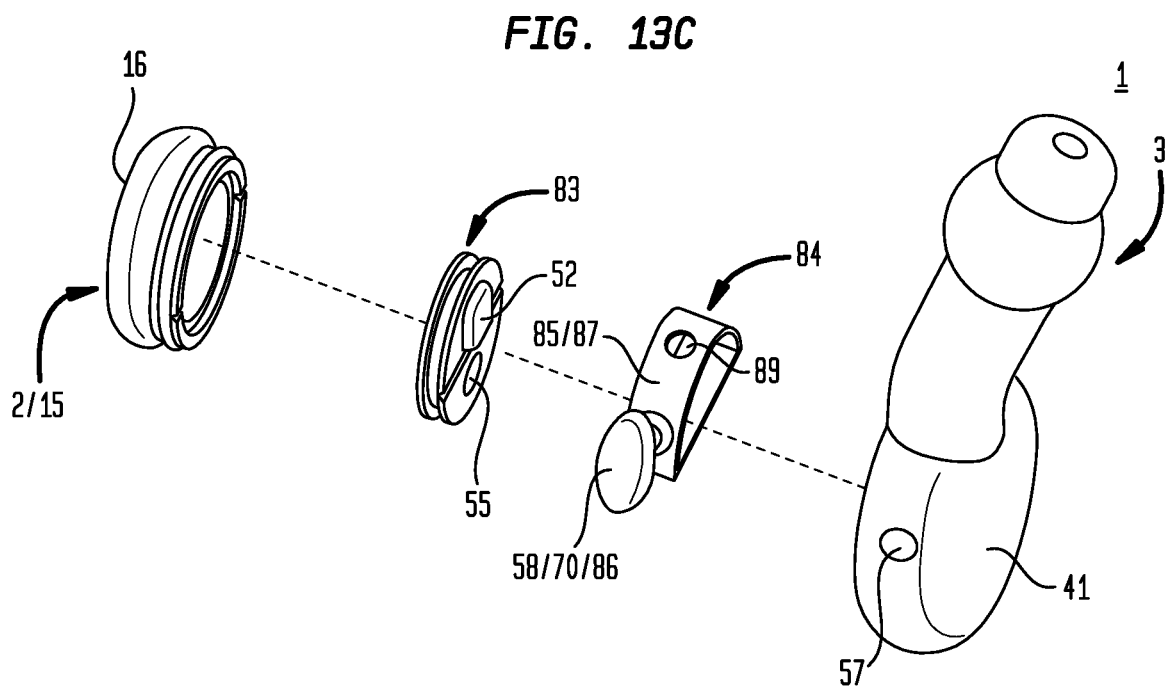

FIG. 13C is an exploded view of a particular embodiment of an external ear canal pressure regulation device.

Figure 13D:
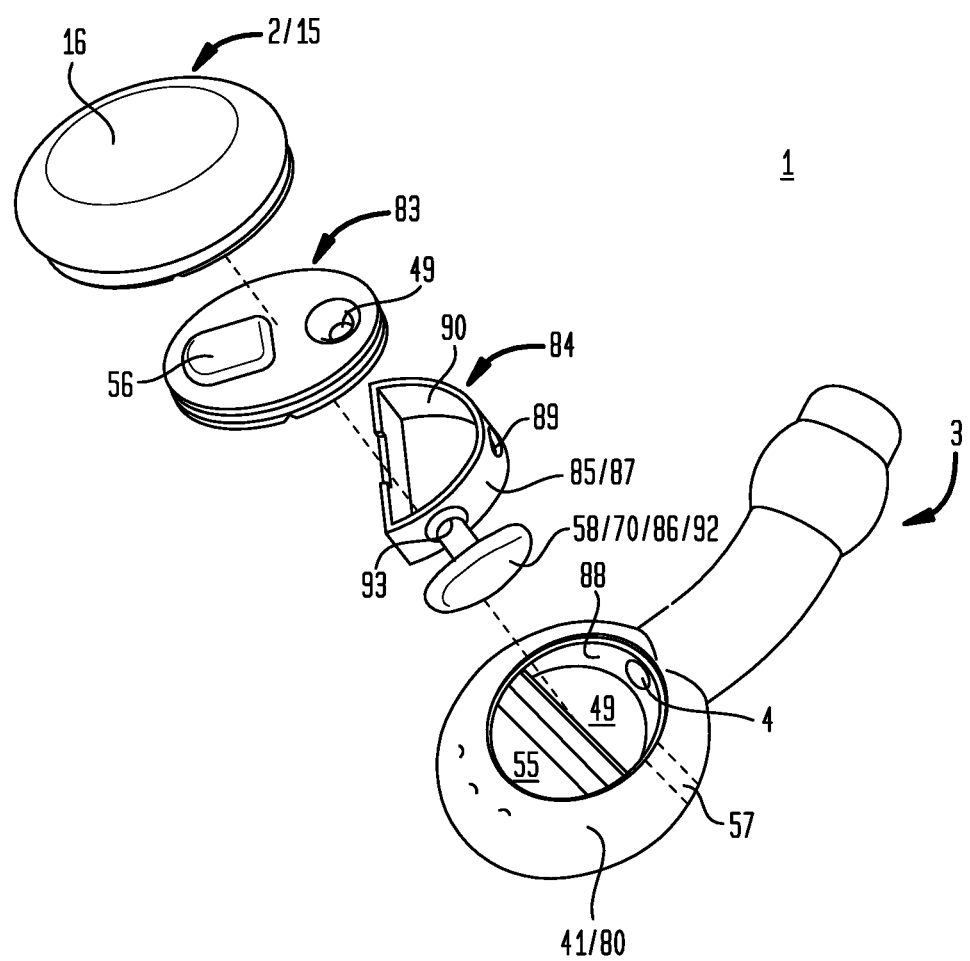

FIG. 13D is an exploded view of a particular embodiment of an external ear canal pressure regulation device.

Figure 13E:
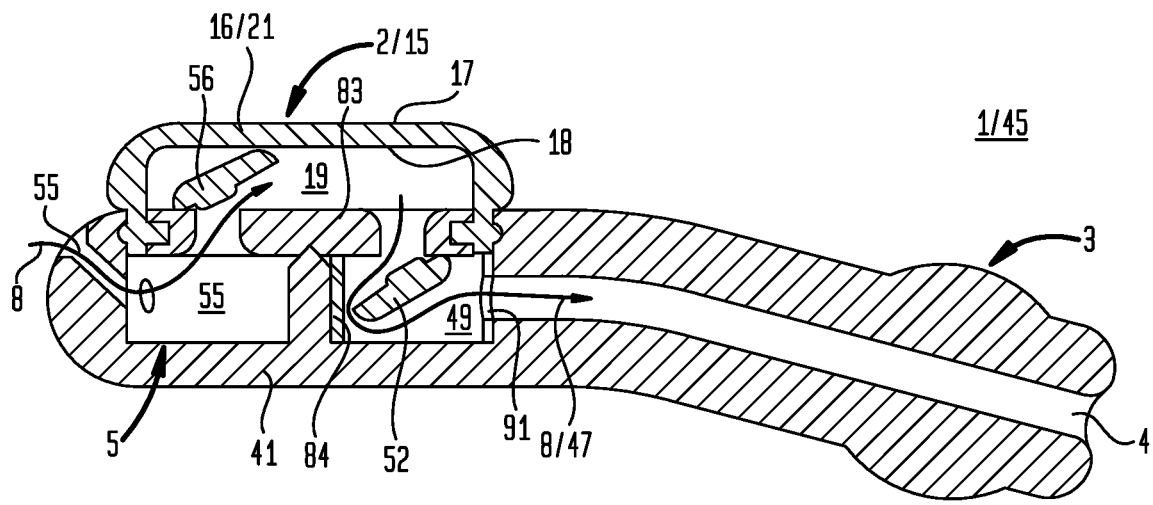

FIG. 13E is a cross sectional view of the particular embodiment of the external ear canal pressure regulation device shown in FIG. 13A operable to generate an external ear canal pressure greater than the ambient pressure.

Figure 13F:
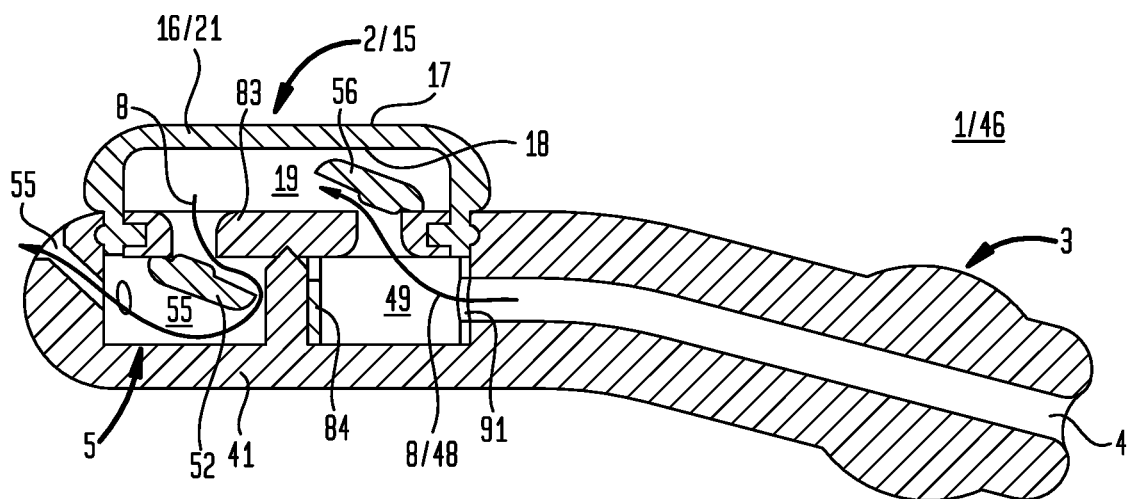

FIG. 13F is a cross sectional view of a particular embodiment of the external ear canal pressure regulation device operable to generate an external ear canal pressure lesser than the ambient pressure.

FIG. 14A is a plot of the external ear canal pressure relative to the ambient pressure achieved over a time period which represents a method of use of the first configuration of the external ear canal pressure regulation device in which operation of the fluid flow generator generates and maintains a substantially invariant external ear canal pressure greater than the ambient pressure at a maximum pressure for a time period and by operation of the pressure relief element, the external ear canal pressure returns toward the ambient pressure.

FIG. 14B is a plot of the external ear canal pressure relative to the ambient pressure achieved over a time period which represents a method of use of the first configuration of the external ear canal pressure regulation device in which operation of the fluid flow generator with intermittent operation of the pressure relief element generates a pulsatile external ear canal pressure greater than the ambient pressure with the pressure wave being a sine wave having smooth repetitive periodic oscillations.

FIG. 14C is a plot of the external ear canal pressure relative to the ambient pressure achieved over a time period which represents a method of use of the first configuration of the external ear canal pressure regulation device in which operation of the fluid flow generator with intermittent operation of the pressure relief element generates a pulsatile external ear canal pressure greater than the ambient pressure with the pressure wave being a truncated wave in which the apex of the pressure wave has a constant pressure over a time period.

FIG. 14D is a plot of the external ear canal pressure relative to the ambient pressure achieved over a time period which represents a method of use of the first configuration of the external ear canal pressure regulation device in which operation of the fluid flow generator with intermittent operation of the pressure relief element generates a pulsatile external ear canal pressure greater than the ambient pressure with the pressure wave being a triangle wave having linear leading and trailing edges.

FIG. 14E is a plot of the external ear canal pressure relative to the ambient pressure achieved over a time period which represents a method of use of the first configuration of the external ear canal pressure regulation device in which operation of the fluid flow generator with intermittent operation of the pressure relief element generates a pulsatile external ear canal pressure greater than the ambient pressure with the pressure wave being a sawtooth wave in which the leading edge changes pressure over a time period which is greater than the time period in which the trailing edge changes pressure.

FIG. 14F is a plot of the external ear canal pressure relative to the ambient pressure achieved over a time period which represents a method of use of the first configuration of the external ear canal pressure regulation device in which operation of the fluid flow generator with intermittent operation of the pressure relief element generates a pulsatile external ear canal pressure greater than the ambient pressure with the pressure wave being a truncated wave in which the apex of the pressure wave has a constant pressure over a time period.

FIG. 14G is a plot of the external ear canal pressure relative to the ambient pressure achieved over a time period which represents a method of use of the first configuration of the external ear canal pressure regulation device in which operation of the fluid flow generator with intermittent operation of the pressure relief element generates a pulsatile external ear canal pressure greater than the ambient pressure.

Figure 15A:
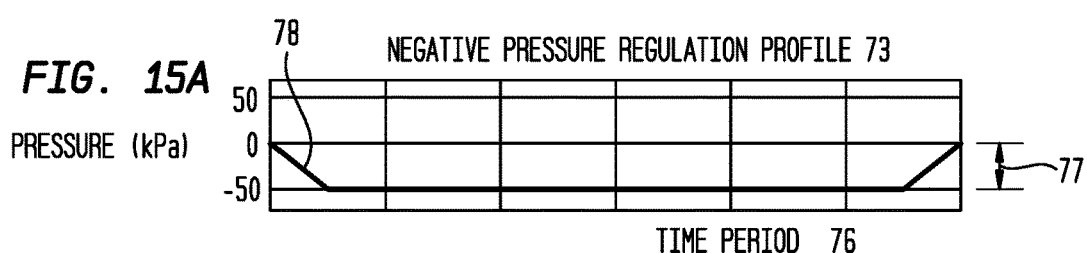

FIG. 15A is a plot of the external ear canal pressure relative to the ambient pressure achieved over a time period which represents a method of use of the second configuration of the external ear canal pressure regulation device in which operation of the fluid flow generator generates and maintains a substantially invariant external ear canal pressure lesser than the ambient pressure at a maximum pressure for a time period and by operation of the pressure relief element, the external ear canal pressure returns toward the ambient pressure.

Figure 15B:
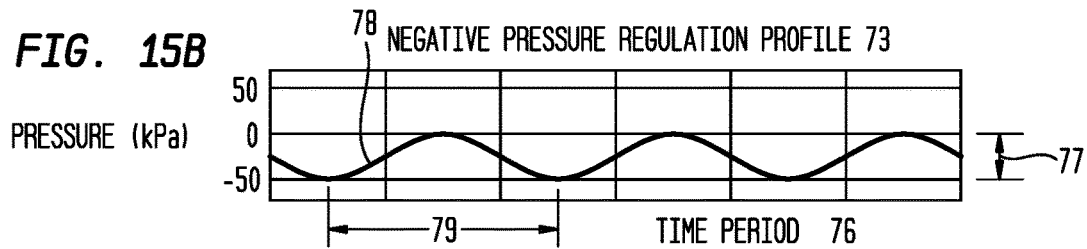

FIG. 15B is a plot of the external ear canal pressure relative to the ambient pressure achieved over a time period which represents a method of use of the second configuration of the external ear canal pressure regulation device in which operation of the fluid flow generator with intermittent operation of the pressure relief element generates a pulsatile external ear canal pressure lesser than the ambient pressure with the pressure wave being a sine wave having smooth repetitive periodic oscillations.

Figure 15C:
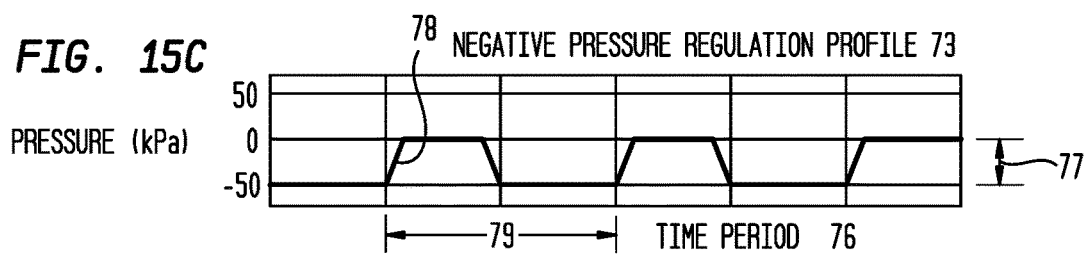

FIG. 15C is a plot of the external ear canal pressure relative to the ambient pressure achieved over a time period which represents a method of use of the second configuration of the external ear canal pressure regulation device in which operation of the fluid flow generator with intermittent operation of the pressure relief element generates a pulsatile external ear canal pressure lesser than the ambient pressure with the pressure wave being a truncated wave in which the apex of the pressure wave has a constant pressure over a time period.

Figure 15D:
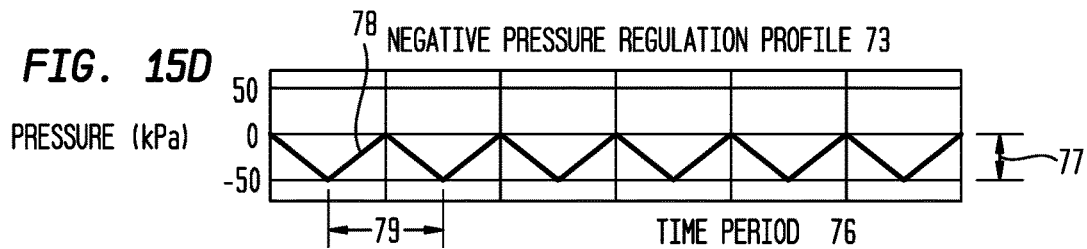

FIG. 15D is a plot of the external ear canal pressure relative to the ambient pressure achieved over a time period which represents a method of use of the second configuration of the external ear canal pressure regulation device in which operation of the fluid flow generator with intermittent operation of the pressure relief element generates a pulsatile external ear canal pressure lesser than the ambient pressure with the pressure wave being a triangle wave having linear leading and trailing edges.

Figure 15E:
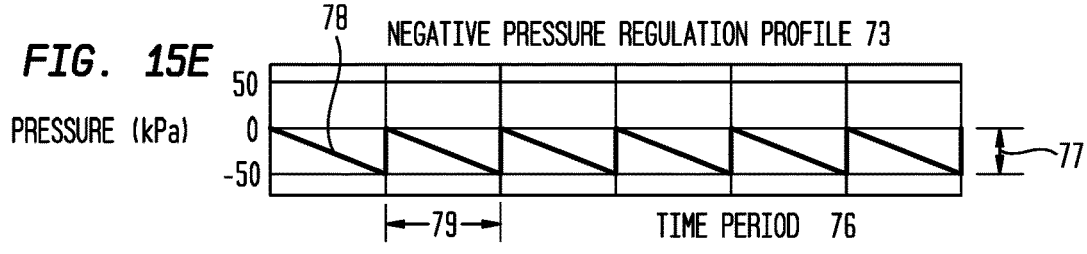

FIG. 15E is a plot of the external ear canal pressure relative to the ambient pressure achieved over a time period which represents a method of use of the second configuration of the external ear canal pressure regulation device in which operation of the fluid flow generator with intermittent operation of the pressure relief element generates a pulsatile external ear canal pressure lesser than the ambient pressure with the pressure wave being a reverse sawtooth wave in which the leading edge changes pressure over a time period which is lesser than the time period in which the trailing edge changes pressure.

Figure 15F:
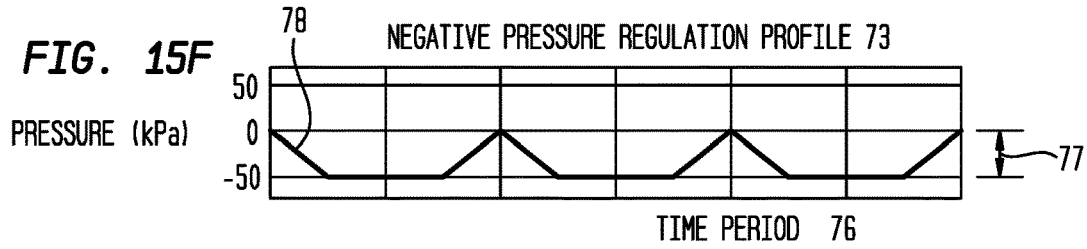

FIG. 15F is a plot of the external ear canal pressure relative to the ambient pressure achieved over a time period which represents a method of use of the second configuration of the external ear canal pressure regulation device in which operation of the fluid flow generator with intermittent operation of the pressure relief element generates a pulsatile external ear canal pressure lesser than the ambient pressure with the pressure wave being a truncated wave in which the apex of the pressure wave has a constant pressure over a time period.

Figure 15G:
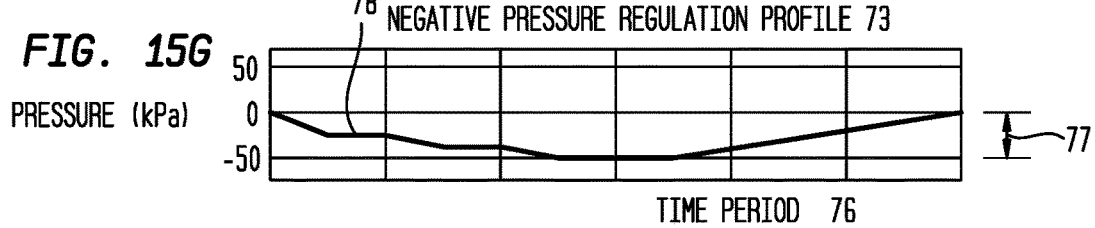

FIG. 15G is a plot of the external ear canal pressure relative to the ambient pressure achieved over a time period which represents a method of use of the second configuration of the external ear canal pressure regulation device in which operation of the fluid flow generator with intermittent operation of the pressure relief element generates a pulsatile external ear canal pressure lesser than the ambient pressure.

IV. MODE(S) FOR CARRYING OUT THE INVENTION

Figure 1A:
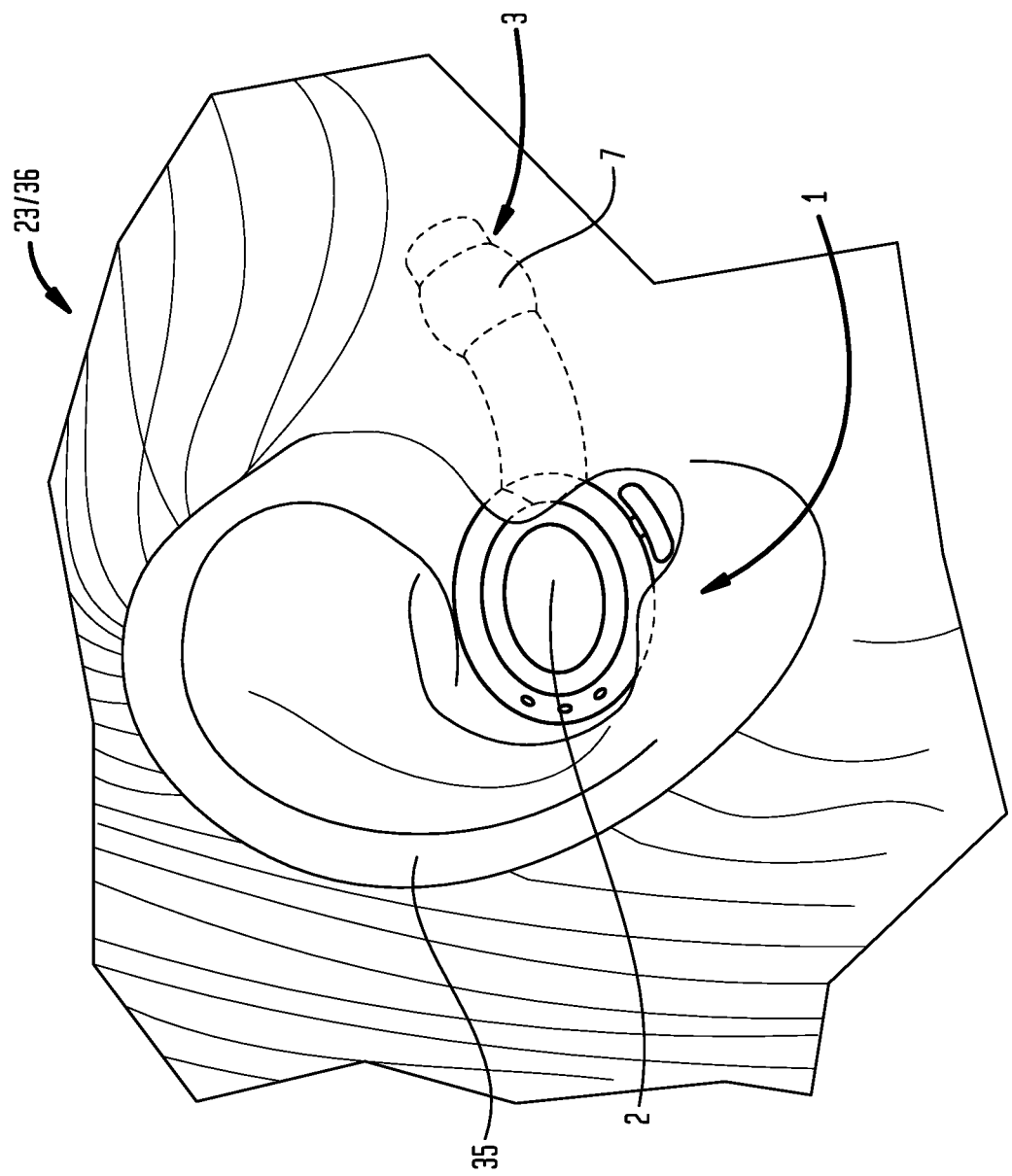
FIG. 1A is an illustration of a particular embodiment of an external ear canal pressure regulation device sealably engaged with the external ear canal.
Figure 1B:
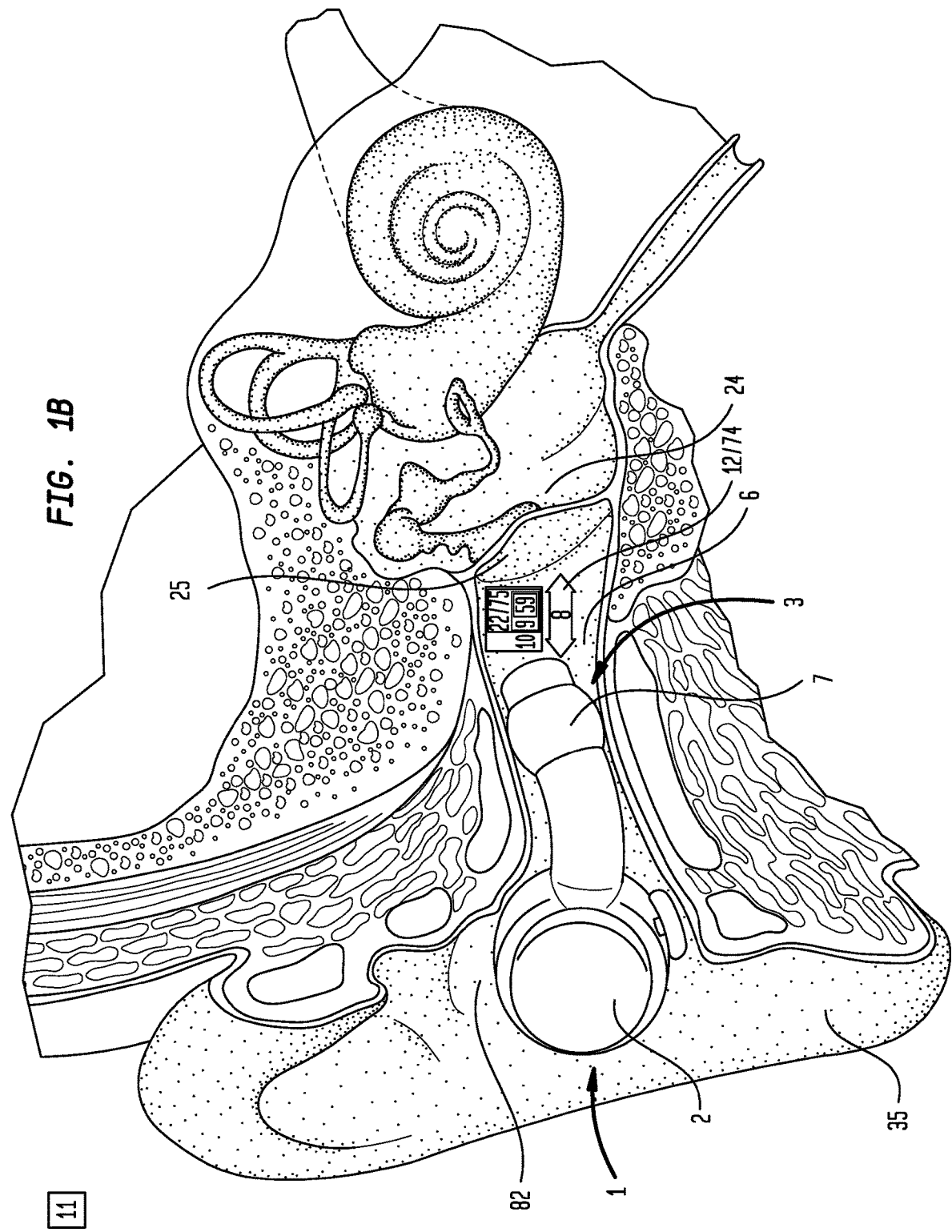
FIG. 1B is an illustration of a particular embodiment of an external ear canal pressure regulation device sealably engaged with the external ear canal.

Now referring primarily to FIG. 1A and FIG. 1B, which illustrate particular methods of using an external ear canal pressure regulation device (1) including one or more of: a fluid flow generator (2), an earpiece (3) having an axial earpiece bore (4), and a valved conduit (5) fluidicly coupled to the fluid flow generator (2) and the axial earpiece bore (4). The method of use can include sealably engaging an external ear canal (6) with an earpiece external surface (7) of the earpiece (3), generating a fluid flow (8) between the fluid flow generator (2) and the axial earpiece bore (4), and regulating a pressure differential (9) between an external ear canal pressure (10) and an ambient pressure (11) to alleviate one or more disorder symptoms or treat one or more disorders.

The term "pressure differential" for the purposes of this invention means the difference in pressure between two locations.

The term "pressure differential amplitude" for the purposes of this invention means the numerical value of the difference in pressure between two locations. The pressure differential amplitude (59) can be expressed as a number without a sign (positive or negative), regardless of whether the pressure is greater or lesser in the first location relative to the second location. As an illustrative example, an external ear canal pressure (10) of +50 kilopascals above the ambient pressure (11) and an external ear canal pressure (10) of −50 kilopascals below the ambient pressure (11) can both have a pressure differential amplitude (59) of 50 kilopascals.

The term "external ear canal pressure" for the purposes of this invention means forces exerted within the external ear canal (6) and, without limitation to the breadth of the foregoing, means forces exerted within the external ear canal (6) by a fluid volume (12), a pre-selected fluid volume (12), or a fluid flow (8) delivered to or generated in the external ear canal (6) by operation of the external ear canal pressure regulation device (1).

The term "ambient pressure" for the purposes of this invention means forces exerted external to the external ear canal (6) in the ambient environment and, without limitation to the breadth of the foregoing, means forces exerted on the earpiece (3) having the earpiece external surface (7) sealably engaged with the external ear canal (6), as herein described.

The term "pre-selected" for the purposes of this invention means a parameter, such as a fluid volume (12) or a pressure differential amplitude (59) which has been determined prior to administration, for example by a user (23) of the external ear canal pressure regulation device (1), for delivery to, generation in, or administration to the external ear canal (6) by operation of the external ear canal pressure regulation device (1) and subsequently delivered to, generated in, or administered to the external ear canal (6) by operation of the external ear canal pressure regulation device (1). For example, a pre-selected fluid volume (12) of 10 milliliters can be prior selected for delivery to the external ear canal (6) by operation of the external ear canal pressure regulation device (1) and subsequently, the pre-selected fluid volume (12) of 10 milliliters can be delivered to the external ear canal (6) by operation of the external ear canal pressure regulation device (1).

The term "symptom" for the purposes of this invention means any discomfort or combination of discomforts associated with a disorder. Without limiting the breadth of the foregoing, symptoms can include: dizziness; vertigo; nausea; imbalance; paresthesia; dysesthesia; sensitivity to light; sensitivity to odor; sensitivity to sound; anxiety; sleeplessness; irritability; fatigue; loss of appetite; blurred vision; gut disturbances; acute pain or chronic pain of varying characteristics including but not limited to throbbing, tearing, sharp, dull, deep, lancinating, burning, aching, stabbing, intense, lightning-like, sense of swelling, or tingling; or the like; or combinations thereof.

The term "disorder" for the purposes of this invention means a physical or mental condition which may not be normal or healthy. Without limiting the breadth of the foregoing, a disorder can include: neuropathic craniofacial pain syndromes such as neuralgias, for example trigeminal neuralgia; temporomandibular joint syndrome; headache syndromes such as migraine headaches, chronic daily headaches, cluster headaches, muscle tension headaches, post-traumatic headaches, or chronic paroxysmal hemicranias; endolymphatic hydrops; vertigo; tinnitus; syndromes resulting from brain injury; syndromes resulting from impaired neurologic function, including cognitive disorders such as attention deficit disorder, emotional disorders such as anxiety disorders, or seizure disorders; phantom limb; middle ear disorders; inner ear disorders; or the like, or combinations thereof.

Figure 2A:
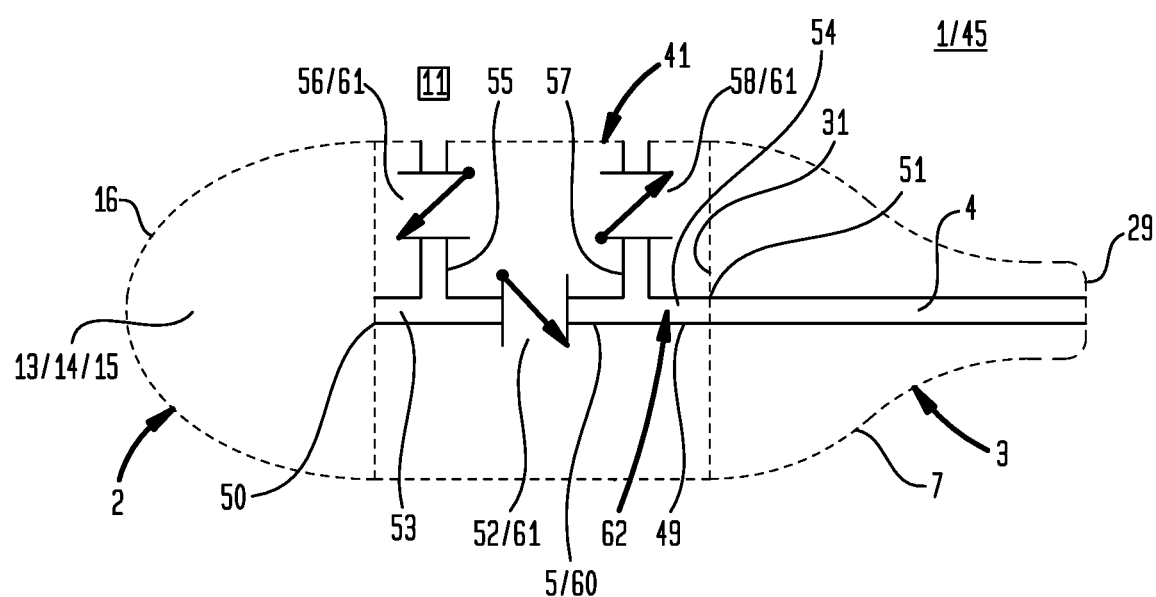
FIG. 2A is a schematic diagram of a particular embodiment of an external ear canal pressure regulation device operable to achieve an external ear canal pressure greater than the ambient pressure.
Figure 2B:
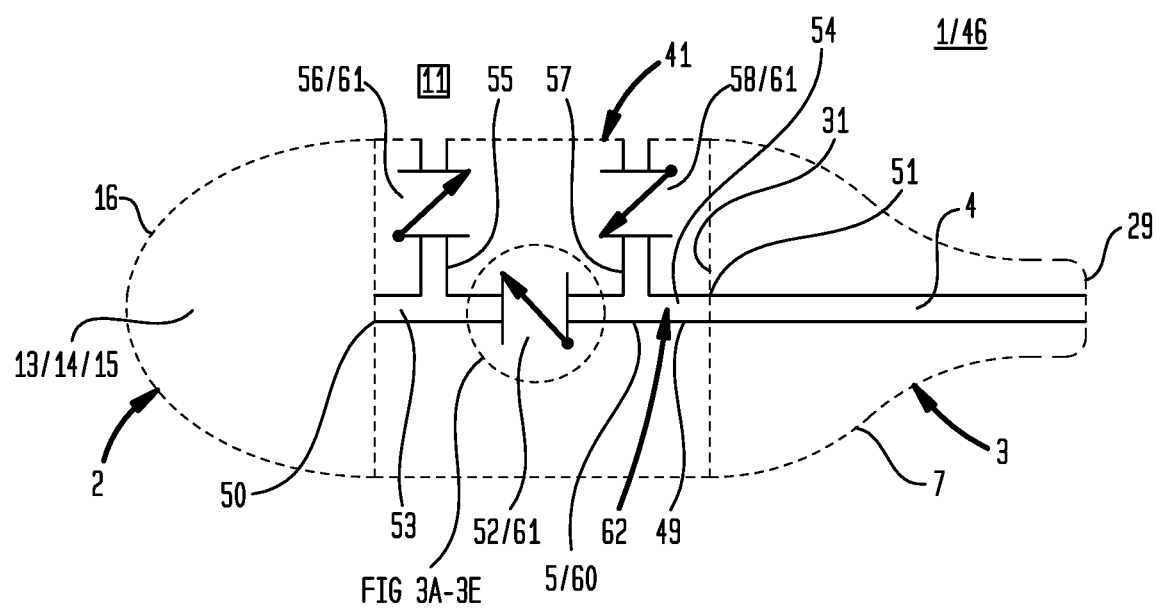
FIG. 2B is a schematic diagram of a particular embodiment of an external ear canal pressure regulation device operable to achieve an external ear canal pressure lesser than the ambient pressure.

Now referring primarily to FIG. 2A and FIG. 2B, the fluid flow generator (2) can have any of a wide variety of numerous configurations capable of generating a fluid flow (8) between the fluid flow generator (2) and the axial earpiece bore (4). As to particular embodiments, the fluid flow generator (2) can include a volumetrically adjustable element (13) capable of adjusting between a greater volume and a lesser volume. As an illustrative example, adjusting the volumetrically adjustable element (13) from a greater volume to a lesser volume can generate a fluid flow (8) away from the fluid flow generator (2) whereas adjusting the volumetrically adjustable element (13) from a lesser volume to a greater volume can generate a fluid flow (8) toward the fluid flow generator (2).

As to particular embodiments, the fluid flow generator (2) can include a bladder (14) or a diaphragm (15) which has a resiliently flexible wall (16) having a wall external surface (17) and a wall internal surface (18). The wall external surface (17) can be configured in any manner which allows deformation of the resiliently flexible wall (16) (as shown in the examples of FIG. 11A through FIG. 12D and FIG. 13A through FIG. 13F). The wall internal surface (18) can define an internal volume (19) (whether in whole or in part as an assembly with the valved conduit (5)). The resiliently flexible wall (16) in a deformed condition (20) (as shown in the examples of FIG. 11B and FIG. 12B) can decrease the internal volume (19), and in return toward a non-deformed condition (21) (as shown in the example of FIG. 11C and FIG. 12C), can increase the internal volume (19). The change in the internal volume (19) can generate a fluid flow (8) between the fluid flow generator (2) and the axial earpiece bore (4), which can be regulated by the valved conduit (5). As to particular embodiments, the bladder (14) or the diaphragm (15) can have an internal volume (19) in the non-deformed condition (21) which can be insufficient upon complete reduction in internal volume (19) to the deformed condition (20) to generate a fluid flow (8) or an amount of pressure (22) capable of causing discomfort to a user (23) of the external ear canal pressure regulation device (1) or injury to an auditory meatus (24) or a tympanic membrane (25).

Figure 4A:
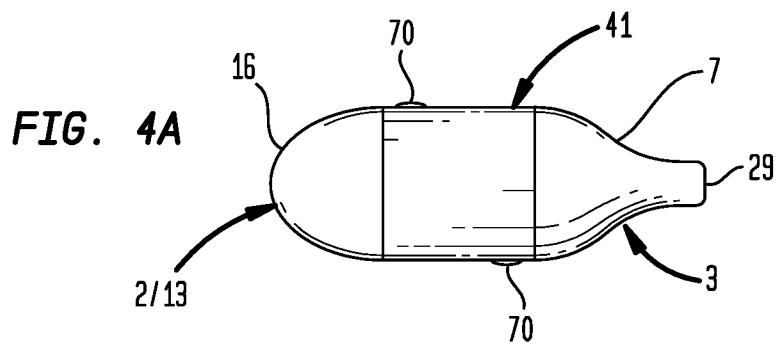
FIG. 4A is an illustration of a particular embodiment of an external ear canal pressure regulation device.
Figure 4B:
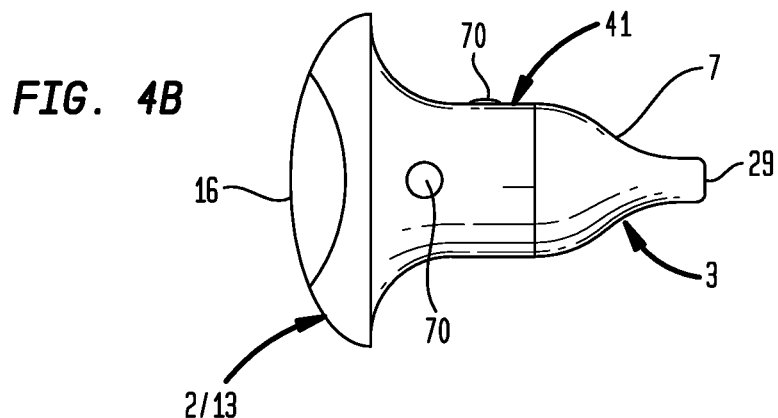
FIG. 4B is an illustration of a particular embodiment of an external ear canal pressure regulation device.
Figure 4C:
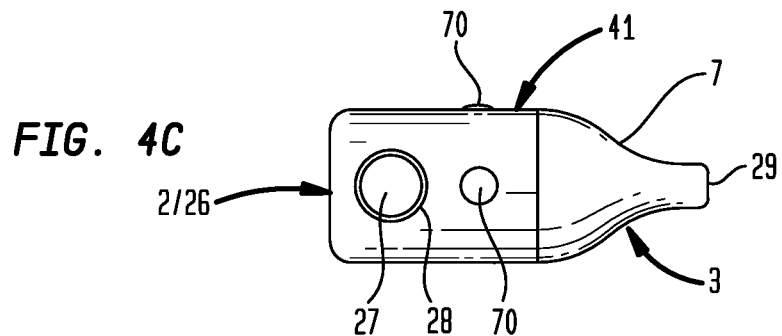
FIG. 4C is an illustration of a particular embodiment of an external ear canal pressure regulation device.
Figure 4D:
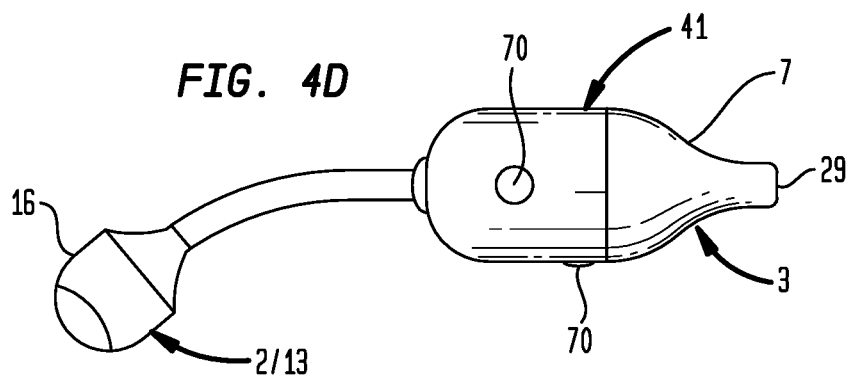
FIG. 4D is an illustration of a particular embodiment of an external ear canal pressure regulation device.

As to other particular embodiments, the fluid flow generator (2) can include a positive displacement pump (26) in which a piston (27) reciprocally operates in a barrel (28) (as shown in the illustrative example of FIG. 4C) to adjust a barrel internal volume between a lesser volume and a greater volume. The reciprocal motion of the piston (27) within the barrel (28) can generate a fluid flow (8) between the fluid flow generator (2) and the axial earpiece bore (4), which can be regulated by the valved conduit (5). As to particular embodiments, the barrel (28) can have a barrel internal volume which can be insufficient upon complete reduction in barrel internal volume by travel of the piston (27) within the barrel (28) to generate a fluid flow (8) or an amount of pressure (22) capable of causing discomfort to the user (23) of the external ear canal pressure regulation device (1) or injury to the auditory meatus (24) or the tympanic membrane (25).

The fluid flow generator (2) can be configured to generate a fluid flow (8) in the valved conduit (5) between the fluid flow generator (2) and the axial earpiece bore (4), whereby the fluid flow (8) can have a fluid volume (12) typically in a range of between 0 milliliters to about 20 milliliters; however, embodiments can have a lesser or greater fluid volume (12) depending upon the application. As to particular embodiments, the fluid volume (12) can be a pre-selected fluid volume (12), which can be selected from one or more of the group including or consisting of: between 0 milliliters to about 2 milliliters, between about 1 milliliter to about 3 milliliters, between about 2 milliliters to about 4 milliliters, between about 3 milliliters to about 5 milliliters, between about 4 milliliters to about 6 milliliters, between about 5 milliliters to about 7 milliliters, between about 6 milliliters to about 8 milliliters, between about 7 milliliters to about 9 milliliters, between about 8 milliliters to about 10 milliliters, between about 9 milliliters to about 11 milliliters, between about 10 milliliters to about 12 milliliters, between about 11 milliliters to about 13 milliliters, between about 12 milliliters to about 14 milliliters, between about 13 milliliters to about 15 milliliters, between about 14 milliliters to about 16 milliliters, between about 15 milliliters to about 17 milliliters, between about 16 milliliters to about 18 milliliters, between about 17 milliliters to about 19 milliliters, and between about 18 milliliters to about 20 milliliters.

One or more pre-selected fluid volumes (12) can be generated with the external ear canal pressure regulation device (1) depending upon the method of use, which can be further influenced by factors such as user (23) anatomy, physiology, or biochemistry of the auditory meatus (24); disorder symptom targeted for alleviation; disorder targeted for treatment; observable effect(s) of using one or more pre-selected fluid volumes (12) in a particular method of using the external ear canal pressure regulation device (1); or the like; or combinations thereof; but not so much as to cause discomfort to the user (23) or injury to the auditory meatus (24) or the tympanic membrane (25).

Again referring primarily to FIGS. 2A and 2B, the earpiece (3) can have a compliant earpiece external surface (7) configured to insert into the external ear canal (6) of the auditory meatus (24), thus acting as a barrier between the external ear canal pressure (10) and the ambient pressure (11). Embodiments of the earpiece (3) can be configured to sufficiently sealably engage with the external ear canal (6) to resist axial or lateral displacement in view of normal anatomical variations of the external ear canal (6) over a normal range of operating temperatures of between about 20° C. (about 68° F.) to about 50° C. (about 122° F.) and allow generation and maintenance of a normal range of operating pressures of between about negative 50 kilopascals (−50 kPa) below the ambient pressure (11) to about positive 50 kilopascals (+50 kPa) above the ambient pressure (11).

The earpiece (3) of the external ear canal pressure regulation device (1) can be formed from a compliant material which can compressibly deform upon engagement with the external ear canal (6), thereby allowing the earpiece (3) to sealably conform to the external ear canal (6). As to these particular embodiments, the earpiece (3) can be formed, molded, three-dimensionally printed, or otherwise fabricated from any of a numerous and wide variety of materials capable of sealable engagement with the external ear canal (6), including or consisting of: a silicone, a foam (including polyurethane foam), a polyvinylsiloxane, a low durometer elastomer, or the like, or combinations thereof.

As to particular embodiments, the earpiece (3) can be formed from one material, for example a lesser durometer elastomer. As to other particular embodiments, the earpiece (3) can be formed from a plurality of layers, for example an inner core layer having a greater durometer surrounded by an outer layer having a lesser durometer or an inner core layer having a lesser durometer surrounded by an outer layer having a greater durometer. As to yet other particular embodiments, a flexible earpiece wall can define a hollow inner space of the earpiece (3), whereby the flexible earpiece wall can deform to allow the earpiece external surface (7) to sealably conform to the external ear canal (6).

Figure 4E:
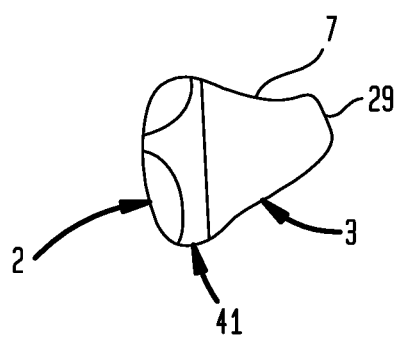
FIG. 4E is an illustration of a particular embodiment of an external ear canal pressure regulation device.
Figure 4F:
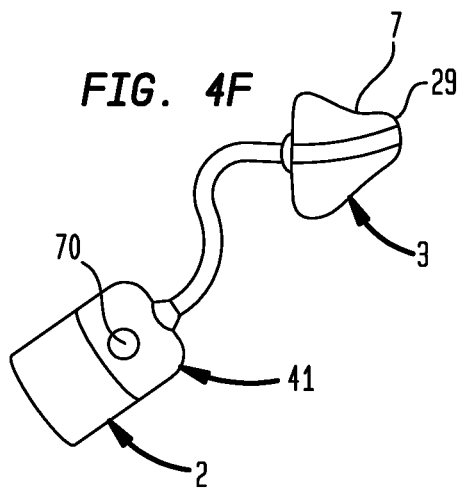
FIG. 4F is an illustration of a particular embodiment of an external ear canal pressure regulation device.
Figure 4G:
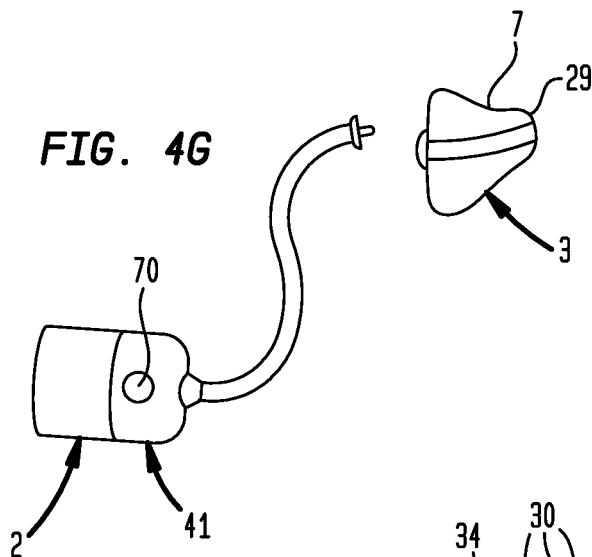
FIG. 4G is an illustration of the particular embodiment of the external ear canal pressure regulation device shown in FIG. 4F in which an earpiece uncouples from a fluid flow generator and a conduit body.

As to particular embodiments, a portion of the earpiece external surface (7) can inwardly taper approaching an earpiece second end (29) (as shown in the examples of FIG. 4A through FIG. 4D). As an illustrative example of particular embodiments of this configuration, the earpiece external surface (7) can be configured in the general form of a truncated cone inwardly tapering approaching the earpiece second end (29) (as shown in the examples of FIG. 4E through FIG. 4G).

Figure 4H:
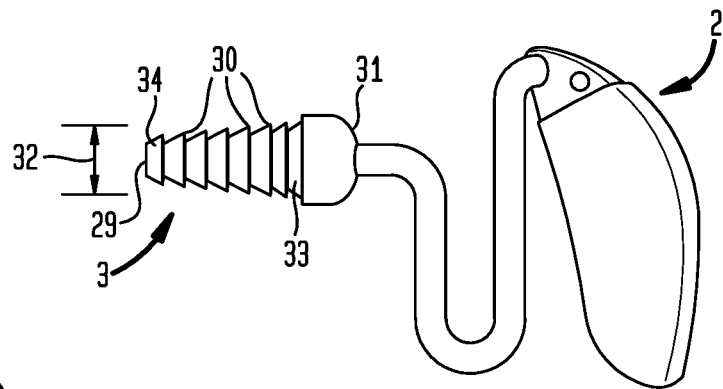
FIG. 4H is an illustration of a particular embodiment of an external ear canal pressure regulation device.
Figure 4I:
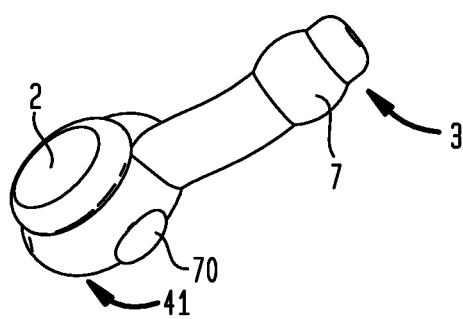
FIG. 4I is an illustration of a particular embodiment of an external ear canal pressure regulation device.

The earpiece external surface (7) can further include a plurality of circumferential ribs (30) disposed in spaced apart relation between an earpiece first end (31) and the earpiece second end (29). Each of the plurality of circumferential ribs (30) can extend from the earpiece external surface (7) a substantially uniform height; however, as to those embodiments of the earpiece external surface (7) having a conical configuration, the plurality of circumferential ribs (30) can have a rib diameter (32) which decreases approaching the earpiece second end (29) (as shown in example of FIG. 4H). As an illustrative example, the rib diameter (32) of a first circumferential rib (33) proximate the earpiece first end (31) can be about seven centimeters and the rib diameter (32) of a last circumferential rib (34) proximate the earpiece second end (29) can be about four centimeters, with the circumferential ribs (30) disposed between the first circumferential rib (33) and the last circumferential rib (34) having rib diameters (32) which respectively decrease from the first circumferential rib (33) to the last circumferential rib (34). However, embodiments need not necessarily be so limited and the plurality of circumferential ribs (30) can be configured in any of a wide variety of numerous configurations adapted to insert into and sealably engage with the external ear canal (6), thus acting as a barrier between the external ear canal pressure (10) and the ambient pressure (11).

The earpiece external surface (7) can remain sealably engaged with the external ear canal (6) by frictional forces between the earpiece external surface (7) and the external ear canal (6). As to particular embodiments, the earpiece external surface (7) can remain engaged with the external ear canal (6) by forcible urging against the external ear canal pressure regulation device (1) during normal operation. As to other particular embodiments, a restraint element coupled to the external ear canal pressure regulation device (1) can be worn about the ear (35) or the head (36) to assist with retention of the earpiece (3) within the external ear canal (6).

Again referring primarily to FIG. 2A and FIG. 2B, the earpiece (3) can have an axial earpiece bore (4) which communicates between the earpiece first end (31) and the earpiece second end (29). The axial earpiece bore (4) proximate the earpiece first end (31) can be fluidicly coupled to a valved conduit (5) and configured to allow a fluid flow (8) between the earpiece first and second ends (31)(29).

Figure 5:
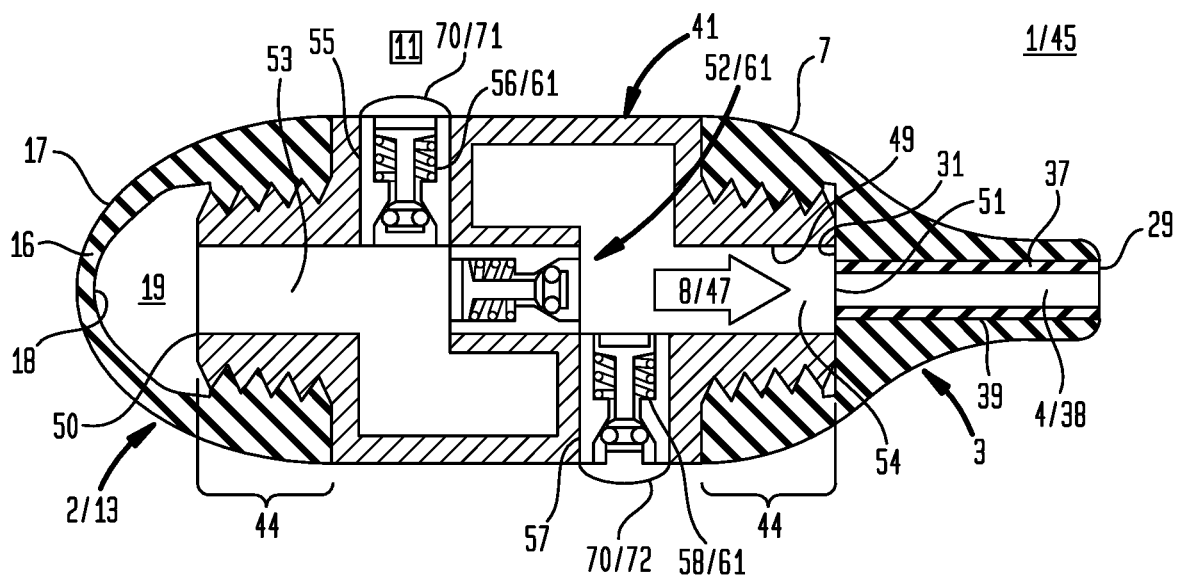
FIG. 5 is a cross sectional view of a particular embodiment of an external ear canal pressure regulation device operable to achieve an external ear canal pressure greater than the ambient pressure.
Figure 6:
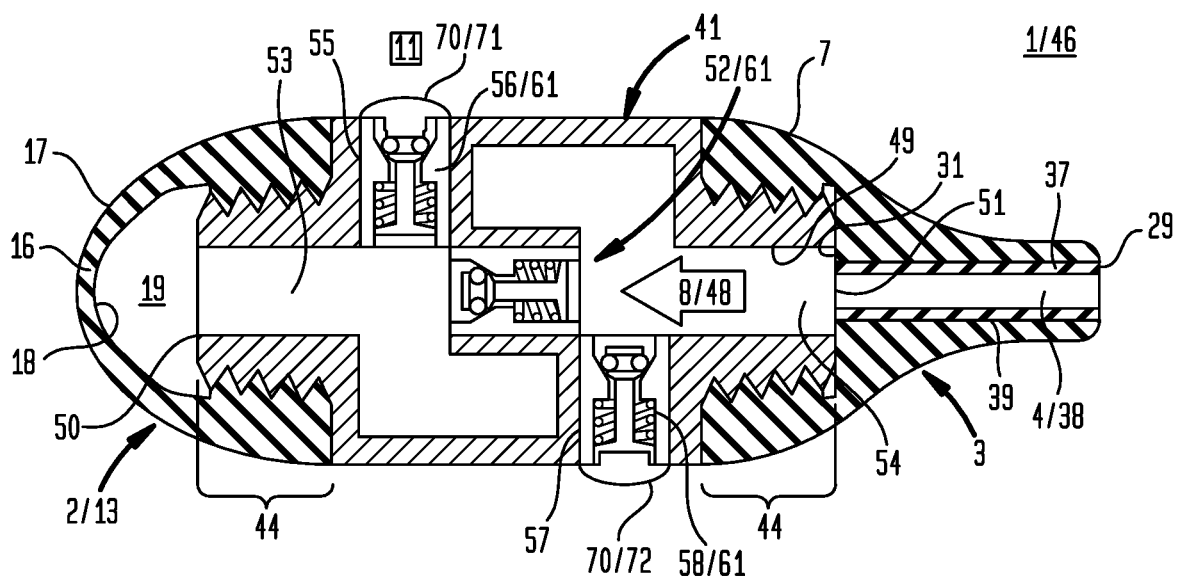
FIG. 6 is a cross sectional view of a particular embodiment of an external ear canal pressure regulation device operable to achieve an external ear canal pressure lesser than the ambient pressure.

Now referring primarily to FIG. 5 and FIG. 6, the earpiece (3) can further include a tubular bolt (37) disposed about the axial earpiece bore (4). The tubular bolt (37) can communicate, whether in whole or in part, between the earpiece first end (31) and the earpiece second end (29), providing a bolt bore (38) communicating, whether in whole or in part, between the earpiece first end (31) and the earpiece second end (29). The tubular bolt (37) can be sufficiently rigid to reduce or prevent deformation of the axial earpiece bore (4) upon sealable engagement of the earpiece external surface (7) with the external ear canal (6) to maintain sufficient fluid flow (8) within the axial earpiece bore (4) during normal use as described above, for example over a normal range of operating temperatures and a normal range of operating pressures.

The tubular bolt (37) can further include a bolt external surface (39) dimensioned for removable insertion into the axial earpiece bore (4), providing an adequate fluid-tight seal to maintain sufficient fluid flow (8) within the axial earpiece bore (4) during normal use as described above, for example over a normal range of operating temperatures and a normal range of operating pressures. As to particular embodiments, the bolt external surface (39) can further include a plurality of circumferential barbs spaced apart along the bolt external surface (39) to assist in retaining the tubular bolt (37) within the axial earpiece bore (4) and in providing the fluid-tight seal.

As to particular embodiments including a discrete tubular bolt (37), the earpiece (3) and the tubular bolt (37) can be provided as a one-piece construct having the earpiece (3) molded or formed about the tubular bolt (37). As to other particular embodiments, the earpiece (3) can be formed or molded to provide increasing rigidity approaching the axial earpiece bore (4). However, embodiments need not necessarily be so limited, as any of a wide variety of numerous structures known to those of ordinary skill in the art can be utilized to provide a tubular bolt (37) in fluid-tight relation with the axial earpiece bore (4).

Figure 7:
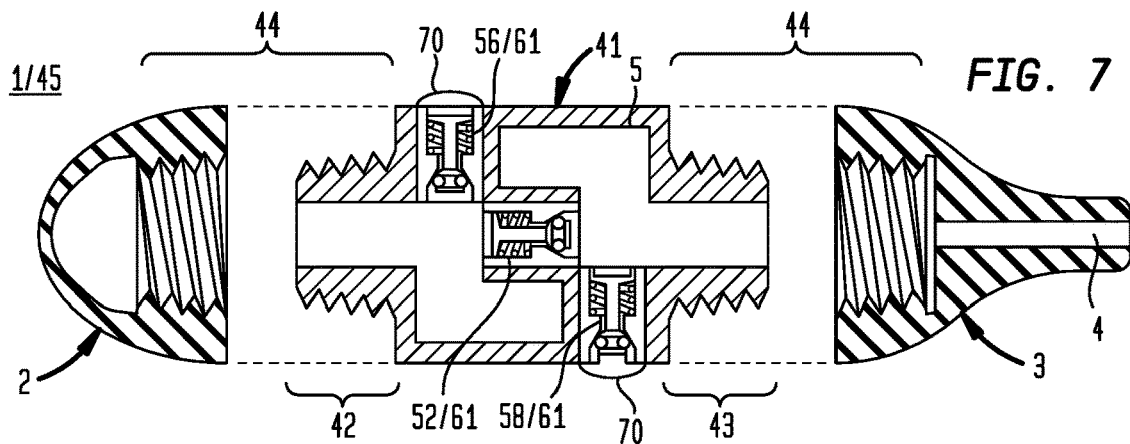
FIG. 7 is an exploded view of the particular embodiment of the external ear canal pressure regulation device shown in FIG. 5 operable to achieve an external ear canal pressure greater than the ambient pressure.

Now referring primarily to FIG. 7 through FIG. 10, the external ear canal pressure regulation device (1) can include a valved conduit (5) fluidicly coupled to the fluid flow generator (2) and the axial earpiece bore (4). As to particular embodiments, the valved conduit (5) can be included in a conduit body (41) having a configuration which removably couples to the fluid flow generator (2) and the earpiece (3), whereby the fluid flow generator (2) and the earpiece (3) can be removably coupled to either one of a conduit body first end (42) or a conduit body second end (43). The releasably couplable surfaces (44) of the fluid flow generator (2), the earpiece (3), the conduit body first end (42), and the conduit body second end (43) can have sufficiently similar configurations (as shown in the example of FIG. 7) to allow the fluid flow generator (2) and the earpiece (3) to releasable couple to either of the conduit body first end (42) or the conduit body second end (43) depending upon whether the valved conduit (5) operates to achieve a pressure differential (9) having the external ear canal pressure (10) greater than the ambient pressure (11) (as shown in the example of FIG. 5) or whether the valved conduit (5) operates to achieve a pressure differential (9) having the external ear canal pressure (10) lesser than ambient the pressure (11) (as shown in the example of FIG. 6).

The releasably couplable surfaces (44) of the fluid flow generator (2), the earpiece (3), the conduit body first end (42), and the conduit body second end (43) can matably engage. As an illustrative example, the releasably couplable surfaces (44) can be configured as rotatably matable spiral threads. However, embodiments need not necessarily be so limited and can have releasably couplable surfaces (44) configured in any of a wide variety of numerous manners which allow the conduit body (41) including the valved conduit (5) to be positioned in a first configuration (45) to operationally achieve a pressure differential (9) having the external ear canal pressure (10) greater than the ambient pressure (11) (as shown in the example of FIG. 5) and further allows the conduit body (41) including the valved conduit (5) to be positioned in a second configuration (46) to operationally achieve a pressure differential (9) having the external ear canal pressure (10) lesser than the ambient pressure (11) (as shown in the example of FIG. 6).

Figure 8:
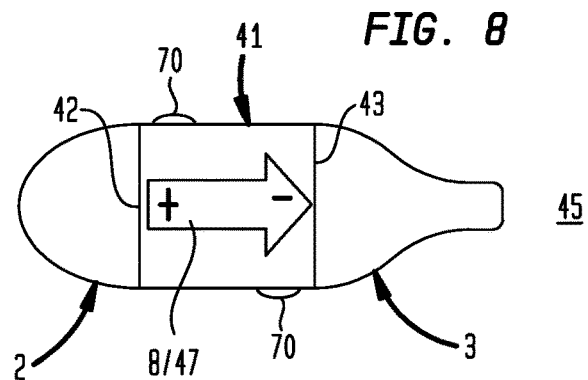
FIG. 8 is an illustration of a first configuration of an external ear canal pressure regulation device operable to achieve an external ear canal pressure greater than the ambient pressure.

As an illustrative example, the conduit body (41) including the valved conduit (5) can be positioned in the first configuration (45) by removably coupling the conduit body first end (42) with the fluid flow generator (2) and removably coupling the conduit body second end (43) with the earpiece (3) (as shown in the example of FIG. 8). As such, the fluid flow (8) can be regulated in a first direction (47) in the valved conduit (8) to operationally achieve a pressure differential (9) having the external ear canal pressure (10) greater than the ambient pressure (11) (as shown in the example of FIG. 5).

Figure 9:
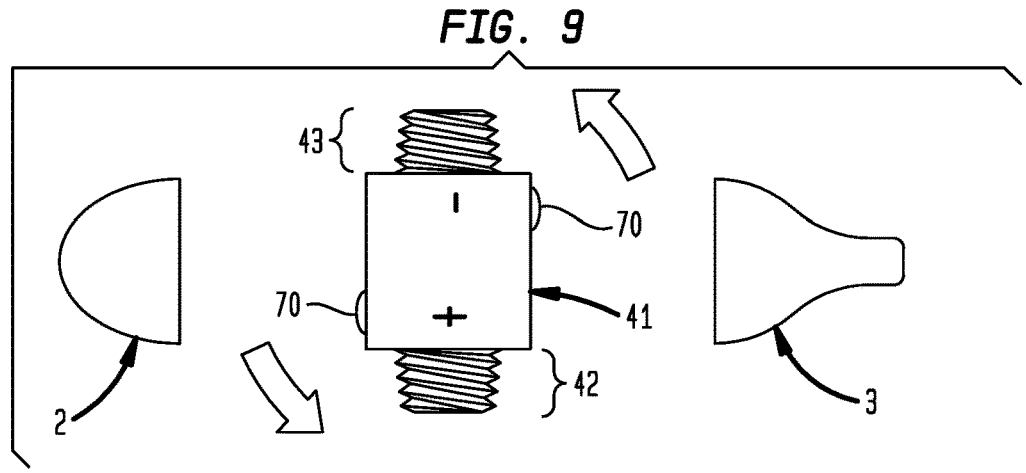
FIG. 9 is an illustration of a method of reconfiguring the first configuration of the external ear canal pressure regulation device shown in FIG. 8 by end-to-end rotation of a conduit body.
Figure 10:
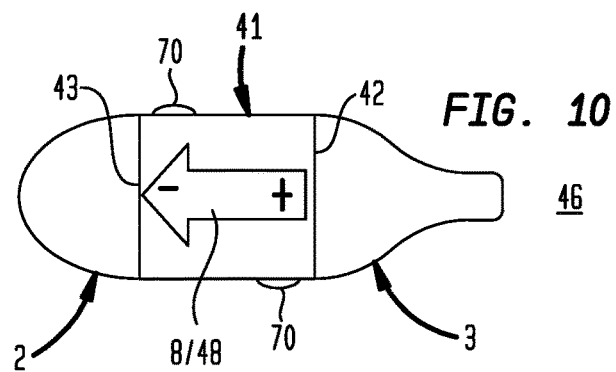
FIG. 10 is an illustration of a second configuration of the external ear canal pressure regulation device achieved by end-to-end rotation of a conduit body operable to achieve an external ear canal pressure lesser than the ambient pressure.

As to particular embodiments, the fluid flow generator (2) can be removed from the conduit body first end (42) and the earpiece (3) can be removed from the conduit body second end (43) to disassemble the first configuration (45). The conduit body (41) can be rotated without any structural alteration to reverse orientation of the conduit body first and second ends (42)(43) (as shown in the example of FIG. 9). The valved conduit (5) can be positioned in the second configuration (46) by removably coupling the conduit body first end (42) with the earpiece (3) and removably coupling the conduit body second end (43) with the fluid flow generator (2) (as shown in the example of FIG. 10). As such, the fluid flow (8) can be regulated in a second direction (48) in the valved conduit (5) to operationally achieve a pressure differential (9) having the external ear canal pressure (10) lesser than the ambient pressure (11) (as shown in the example of FIG. 6).

Now referring primarily to FIG. 2A, FIG. 2B, FIG. 5, and FIG. 6, the valved conduit (5) can include a first fluid flow conduit (49) communicating between a first fluid flow conduit first end (50) and a first fluid flow conduit second end (51). As to the particular embodiments of the external ear canal pressure regulation device (1) described herein, the first fluid flow conduit first end (50) communicates with the fluid flow generator (2) and the first fluid flow conduit second end (51) communicates with the axial earpiece bore (4) of the earpiece (3), whether the conduit body (41) is positioned in the first configuration (45) or the second configuration (46).

The first fluid flow conduit (49) can be interruptible by a first valve (52) to unidirectionally regulate the fluid flow (8) between the first fluid flow conduit first and second ends (50)(51) and, correspondingly, between the fluid flow generator (2) and the axial earpiece bore (4). In the first configuration (45) described above, the fluid flow generator (2) can be sealably engaged with the first fluid flow conduit first end (50) and the axial earpiece bore (4) can be sealably engaged with the first fluid flow conduit second end (51) to unidirectionally regulate the fluid flow (8) in the first direction (47) from the fluid flow generator (2) toward the axial earpiece bore (4). As such, the external ear canal pressure regulation device (1) sealably engaged with an external ear canal (6) can operationally achieve a pressure differential (9) having the external ear canal pressure (10) greater than the ambient pressure (11) by transferring a fluid volume (12) from the fluid flow generator (2) toward the external ear canal (6). In the second configuration (46) described above, the fluid flow generator (2) can be sealably engaged with the first fluid flow conduit first end (50) and the axial earpiece bore (4) can be sealably engaged with the first fluid flow conduit second end (51) to unidirectionally regulate the fluid flow (8) in the second direction (48) from the axial earpiece bore (4) toward the fluid flow generator (2). As such, the external ear canal pressure regulation device (1) sealably engaged with an external ear canal (6) can operationally achieve a pressure differential (9) having the external ear canal pressure (10) lesser than the ambient pressure (11) by transferring a fluid volume (12) from the external ear canal (6) toward the fluid flow generator (2).

Again referring primarily to FIG. 2A, FIG. 2B, FIG. 5, and FIG. 6, the first valve (52) can divide the first fluid flow conduit (49) into a first portion (53) proximate the first fluid flow conduit first end (50) and, correspondingly, proximate the fluid flow generator (2), and a second portion (54) proximate the first flow fluid conduit second end (51), and, correspondingly, proximate the axial earpiece bore (4) of the earpiece (3). As to particular embodiments, the valved conduit (5) can further include a second fluid flow conduit (55) fluidicly coupled between the first portion (53) of the first fluid flow conduit (49) and the ambient pressure (11). As to the particular embodiments of the external ear canal pressure regulation device (1) described herein, the second fluid flow conduit (55) fluidicly couples to the first portion (53) of the first fluid flow conduit (49) proximate the fluid flow generator (2), whether the conduit body (41) is positioned in the first configuration (45) or the second configuration (46). The second fluid flow conduit (55) can be interruptible by a second valve (56) to unidirectionally regulate the fluid flow (8) in the second fluid flow conduit (55).

Now referring primarily to FIG. 2A and FIG. 5, as to particular embodiments of the first configuration (45) having a fluid flow generator (2) which includes a volumetrically adjustable element (13) having an internal volume (19) bounded by a resiliently flexible wall (16), a deformed condition (20) of the resiliently flexible wall (16) can decrease the internal volume (19) to generate a fluid flow (8) in the first direction (47) in the first fluid flow conduit (49) from the fluid flow generator (2) toward the axial earpiece bore (4) of the earpiece (3), whereby the first valve (52) and the second valve (56) unidirectionally regulate the fluid flow (8) to egress from the axial earpiece bore (4). As such, the external ear canal pressure regulation device (1) sealably engaged with an external ear canal (6) can operationally achieve a pressure differential (9) having the external ear canal pressure (10) greater than the ambient pressure (11) by transferring a fluid volume (12) from the fluid flow generator (2) toward the external ear canal (6).

The resiliently flexible wall (16) of the volumetrically adjustable element (13) can return to a non-deformed condition (21) which can increase the internal volume (19) to generate a fluid flow (8) in the second fluid flow conduit (55), whereby the second valve (56) unidirectionally regulates the fluid flow (8) to ingress from an ambient pressure (11) toward the fluid flow generator (2). The first valve (52) can interrupt the fluid flow (8) in the first fluid flow conduit (49) from the axial earpiece bore (4) toward the fluid flow generator (2). Embodiments of the external ear canal pressure regulation device (1) sealably engaged with an external ear canal (6) can operationally maintain a pressure differential (9) in which the external ear canal pressure (10) can be maintained greater than the ambient pressure (11) and concurrently transfer a fluid volume (12) from the ambient pressure (11) toward the fluid flow generator (2) to return the resiliently flexible wall (16) of the volumetrically adjustable element (13) toward the non-deformed condition (21).

Now referring primarily to FIG. 2B and FIG. 6, as to particular embodiments of the second configuration (46) having a fluid flow generator (2) which includes a volumetrically adjustable element (13) having an internal volume (19) bounded by a resiliently flexible wall (16), a deformed condition (20) of the resiliently flexible wall (16) can decrease the internal volume (19) to generate a fluid flow (8) in the second fluid flow conduit (55) from the fluid flow generator (2) toward the ambient pressure (11), whereby the first valve (52) and the second valve (56) unidirectionally regulate the fluid flow (8) to egress from the second fluid flow conduit (55) toward the ambient pressure (11).

The resiliently flexible wall (16) of the volumetrically adjustable element (13) can return to a non-deformed condition (21) which can increase the internal volume (19) to generate a fluid flow (8) in the second direction (48) in the first fluid flow conduit (49), whereby the first valve (52) unidirectionally regulates the fluid flow (8) to ingress from the axial earpiece bore (4) of the earpiece (3) toward the fluid flow generator (2). The second valve (56) can interrupt the fluid flow (8) in the second fluid flow conduit (55) from the ambient pressure (11) toward the fluid flow generator (2). As such, the external ear canal pressure regulation device (1) sealably engaged with an external ear canal (6) can operationally achieve and maintain a pressure differential (9) in which the external ear canal pressure (10) can be maintained lesser than the ambient pressure (11) and concurrently transfer a fluid volume (12) from the external ear canal (6) toward the fluid flow generator (2) to return the resiliently flexible wall (16) of the volumetrically adjustable element (13) toward the non-deformed condition (21).

Now referring primarily to FIG. 2A, FIG. 2B, FIG. 5, and FIG. 6, as to particular embodiments, the valved conduit (5) can further include a third fluid flow conduit (57) fluidicly coupled between the second portion (54) of the first fluid flow conduit (49) and the ambient pressure (11). As to the particular embodiments of the external ear canal pressure regulation device (1) described herein, the third fluid flow conduit (57) fluidicly couples to the second portion (54) of the first fluid flow conduit (49) proximate the axial earpiece bore (4), whether the conduit body (41) is positioned in the first configuration (45) or the second configuration (46).

The third fluid flow conduit (57) can be interruptible by a third valve (58) to unidirectionally regulate the fluid flow (8) in the third fluid flow conduit (57). As to particular embodiments, the third valve (58) can regulate the fluid flow (8) to egress toward the ambient pressure (11) from the third fluid flow conduit (57). As to other particular embodiments, the third valve (58) can regulate the fluid flow (8) to ingress from the ambient pressure (11) toward the third fluid flow conduit (57).

As to particular embodiments, the third valve (58) can interrupt the fluid flow (8) within the third fluid flow conduit (57) until a pressure differential (9) between the second portion (54) of the first fluid flow conduit (49) and the ambient pressure (11) exceeds a pre-selected pressure differential (9) having a pressure differential amplitude (59) typically in a range of between 0 kilopascals to about 50 kilopascals; however embodiments can have a lesser or greater pre-selected pressure differential amplitude (59) depending upon the application. As to particular embodiments, the pre-selected pressure differential amplitude (59) can be selected from the group including of consisting of: between 0 kilopascals to about 5 kilopascals, between about 2.5 kilopascals to about 7.5 kilopascals, between about 5 kilopascals to about 10 kilopascals, between about 7.5 kilopascals to about 12.5 kilopascals, between about 10 kilopascals to about 15 kilopascals, between about 12.5 kilopascals to about 17.5 kilopascals, between about 15 kilopascals to about 20 kilopascals, between about 17.5 kilopascals to about 22.5 kilopascals, between about 20 kilopascals to about 25 kilopascals, between about 22.5 kilopascals to about 27.5 kilopascals, between about 25 kilopascals to about 30 kilopascals, between about 27.5 kilopascals to about 32.5 kilopascals, between about 30 kilopascals to about 35 kilopascals, between about 32.5 kilopascals to about 37.5 kilopascals, between about 35 kilopascals to about 40 kilopascals, between about 37.5 kilopascals to about 42.5 kilopascals, between about 40 kilopascals to about 45 kilopascals, between about 42.5 kilopascals to about 47.5 kilopascals, and between about 45 kilopascals to about 50 kilopascals.

One or more pre-selected pressure differential amplitudes (59) can be generated with the external ear canal pressure regulation device (1) depending upon the method of use, which can be further influenced by factors such as user (23) anatomy, physiology, or biochemistry of the auditory meatus (24); disorder symptom targeted for alleviation; disorder targeted for treatment; observable effect(s) of using one or more pre-selected pressure differential amplitudes (59) in a particular method of using the external ear canal pressure regulation device (1); or the like; or combinations thereof; but not so much as to cause discomfort to the user (23) or injury to the auditory meatus (24) or the tympanic membrane (25).

Now referring primarily to FIG. 2A and FIG. 2B, the valved conduit (5) can include a fluid flow manifold (60) interruptible by operation of one or more valves (61), for example the first valve (52), the second value (56), the third value (58), or additional valves (61) to correspondingly alter the configuration of a manifold fluid flow path (62) within the fluid flow manifold (60) to regulate the fluid flow (8) within the fluid flow manifold (60). While the figures schematically illustrate particular configurations of the fluid flow manifold (60) which correspondingly define particular configurations of the manifold fluid flow path (62), these embodiments need not necessarily be so limited in regard to the configuration of the fluid flow manifold (60) or the manifold fluid flow path (62) of the valved conduit (5) and embodiments can include any of a wide variety of numerous configurations which can fluidicly couple the first, second, or third fluid flow conduits (49)(55)(57) as above described (or additional fluid flow conduits) whether as a plurality of discrete conduits, a one-piece manifold, or defined by a conduit body (41) whether formed, molded, three-dimensionally printed, or otherwise fabricated as a one-piece construct or assembled from a plurality of pieces into which the first, second, or third valves (52)(56)(58) (or additional valves (61)) can be disposed, assembled, or otherwise coupled to generate the valved conduit (5) and without limitation to the breadth of the foregoing, include the configurations of the conduit body (41) shown in illustrative examples of FIG. 4A through FIG. 6, which can be injection molded as a one-piece conduit body (41) about or which can receive the first, second, or third valves (52)(56)(58) (or additional valves).

Figure 3A:
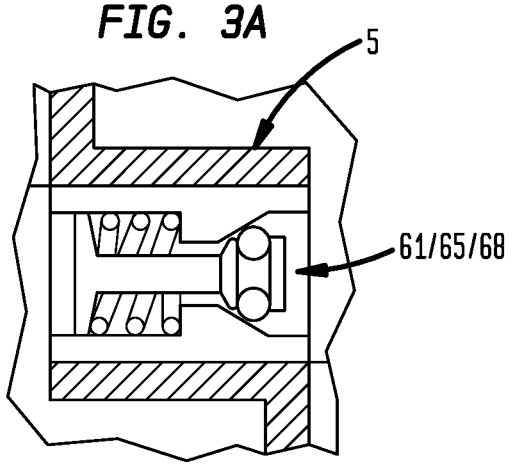
FIG. 3A is a cross sectional view of a particular embodiment of a valve which can be utilized in embodiments of the external ear canal pressure regulation device.
Figure 3B:
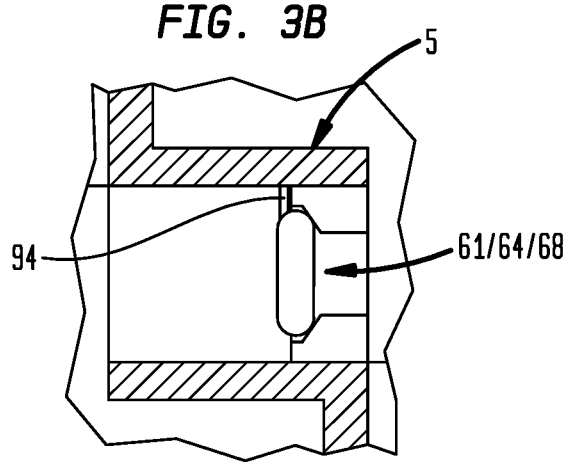
FIG. 3B is a cross sectional view of a particular embodiment of a valve which can be utilized in embodiments of the external ear canal pressure regulation device.
Figure 3C:
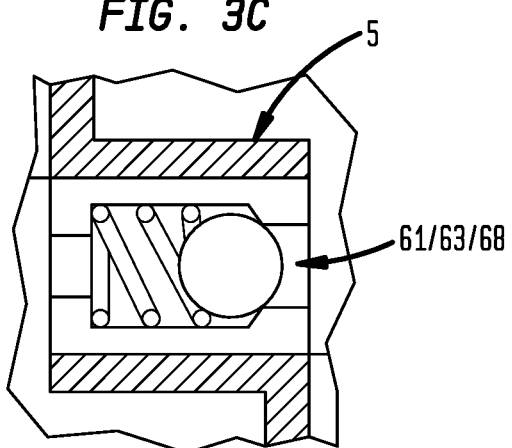
FIG. 3C is a cross sectional view of a particular embodiment of a valve which can be utilized in embodiments of the external ear canal pressure regulation device.
Figure 3D:
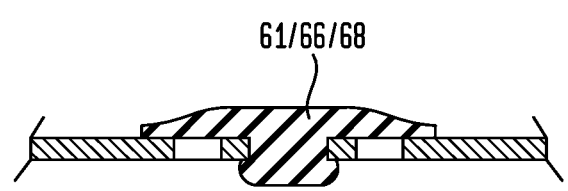
FIG. 3D is a cross sectional view of a particular embodiment of a valve which can be utilized in embodiments of the external ear canal pressure regulation device.
Figure 3E:
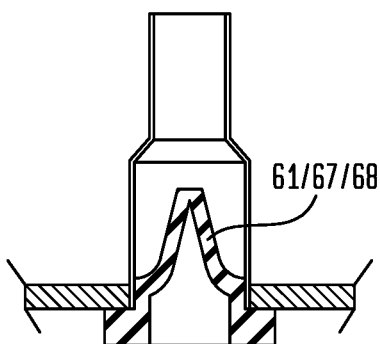
FIG. 3E is a cross sectional view of a particular embodiment of a valve which can be utilized in embodiments of the external ear canal pressure regulation device.

Now referring primarily to FIG. 3A through FIG. 3E, the first, second, or third valves (52)(56)(58) schematically illustrated in FIG. 2A and FIG. 2B can have any type of valve configuration capable of regulating a fluid flow (8) as described herein and without limitation to the breadth of the foregoing, can include a spring-loaded ball check valve (63) (as shown in the example of FIG. 3C), a flapper valve (64) having a hinge (94) (as shown in the example of FIG. 3B), a spring-loaded valve having a seat and seatable deformable circular lip (65) (as shown in the example of FIG. 3A), an umbrella valve (66) (as shown in the example of FIG. 3D), a duckbill valve (67) (as shown in the example of FIG. 3E), or other valves (61) which can operate between a closed condition (68) and an open condition (69) to unidirectionally regulate fluid flow (8) in a pre-selected range.

As to particular embodiments, each of the first, second, or third valves (52)(56)(58) can operate between the closed condition (68), which can be substantially leak-tight to backward flow and substantially leak-tight to forward fluid flow (8) up to about a 50 kilopascal pressure differential amplitude (59) on opposed sides of the valve (61), and the open condition (69), which can have a forward flow in the range of about 0.2 milliliters per second to about 20 milliliters per second. As to particular embodiments, the pressure differential (9) between opposed sides of a valve (61) or the forward fluid flow (8) in the open condition (69) of a valve (61) can be adjusted by the configuration of the valve (61), the unrestricted cross-sectional area of the manifold fluid flow path (62), or the like, or combinations thereof. Additionally, while examples of the external ear canal pressure regulation device (1) disclosed can generate a pressure differential amplitude (59) between the external ear canal pressure (10) and the ambient pressure (11) of up to 50 kilopascals, these examples are not intended to teach or suggest that all embodiments of the external ear canal pressure regulation device (1) necessarily achieve this pressure differential amplitude (59) between the external ear canal pressure (10) and the ambient pressure (11). Rather, particular embodiments of the external ear canal pressure regulation device (1) can be configured to achieve a pressure differential (9) between the external ear canal pressure (10) and the ambient pressure (11) based on being effective to alleviate one or more disorder symptoms, for example neurologically-mediated pain, or treat one or more disorders, for example craniofacial pain syndromes or headache syndromes.

Now referring primarily to FIG. 5, FIG. 6, and FIG. 11A through FIG. 12D, as to particular embodiments, a valve (61) can be operatively coupled to a pressure relief element (70) configured to allow manual operation of the valve (61) between the closed condition (68) and the open condition (69). As an illustrative example, a pressure relief element (70) can be operable to allow the external ear canal pressure (10) to return toward the ambient pressure (11), whether from an external ear canal pressure (10) greater than the ambient pressure (11) or an external ear canal pressure (10) lesser than the ambient pressure (11). As to particular embodiments, a pressure relief element (70) can be operable to allow a fluid volume (12) to egress from a portion of the valved conduit (5) toward the ambient pressure (11) or ingress from the ambient pressure (11) toward a portion of the valved conduit (5) upon reaching or exceeding a pre-selected threshold external ear canal pressure (10), thereby reducing the risk of discomfort to a user (23) or injury to the auditory meatus (24) or the tympanic membrane (25).

As to particular embodiments, the pressure relief element (70) can be configured to extend a sufficient distance outward from the conduit body (41) to allow gripping engagement by a user (23). As to other particular embodiments, the pressure relief element (70) can be configured as a resiliently flexible portion of the conduit body (41) which can flex upon pressing engagement, placing the valve (61) in the open condition (69). Upon disengagement of the pressure relief element (70), the valve (61) can return to the closed condition (68).

Again referring primarily to FIG. 5, FIG. 6, and FIG. 11A through FIG. 12D, as to particular embodiments, a second valve pressure relief element (71) can be coupled to the second valve (56) and a third valve pressure relief element (72) can be coupled to the third valve (58). Each of the second and third valve pressure relief elements (71)(72) can be manually operable to correspondingly generate a fluid flow (8) in the second or third fluid flow conduits (55)(57), respectively.

Now referring primarily to FIG. 11A through FIG. 12D, as to particular embodiments, the external ear canal pressure regulation device (1) can be configured to achieve an external ear canal pressure (10) which can be lesser or greater than the ambient pressure (11). The effective amount of external ear canal pressure (10) to alleviate one or more disorder symptoms or treat one or more disorders, or the greatest amount of external ear canal pressure (10) achieved in a pressure regulation profile (73) generated by an embodiment of the external ear canal pressure regulation device (1) can have a range from just above or just below the ambient pressure (11) to just above or below the external ear canal pressure (10) at which discomfort may occur to a user (23) or injury may occur to the auditory meatus (24) or the tympanic membrane (25). While authorities vary on the external ear canal pressure (10) that may result in discomfort to a user (23) or injury to the auditory meatus (24) or the tympanic membrane (25), typically embodiments of the external ear canal pressure regulation device (1) would not be configured to operate in excess of about −50 kilopascals below the ambient pressure (11) or about +50 kilopascals above the ambient pressure (11).

Now referring primarily to FIG. 2A, FIG. 5, and FIG. 11A through FIG. 11D, as to particular embodiments, the external ear canal pressure regulation device (1) can be configured to achieve an external ear canal pressure (10) which can be greater than the ambient pressure (11). As such, the valved conduit (5) can be coupled to the fluid flow generator (2) and the axial earpiece bore (4) of the earpiece (3) in the first configuration (45) to unidirectionally regulate the fluid flow (8) in the first direction (47) in the first fluid flow conduit (5) to egress from the axial earpiece bore (4) toward the external ear canal (6).

As shown in FIG. 11A and FIG. 11B, the earpiece external surface (7) of the earpiece (3) can be sealably engaged with the external ear canal (6) as described above. Operation of the fluid flow generator (2) can compress an amount of fluid (74) in the first portion (53) of the first fluid flow conduit (49). As to those embodiments including a volumetrically adjustable element (13), the resiliently flexible wall (16) can be deformed to reduce the internal volume (19) of the volumetrically adjustable element (13) to compress the amount of fluid (74) in the first portion (53) of the first fluid flow conduit (49), resulting in a pressure differential (9) between opposite sides of the first valve (52) and the second valve (56). As to those embodiments including a piston (27) which reciprocally operates in a barrel (28), the piston (27) can travel within the barrel (28) to reduce the barrel internal volume, thus resulting in a pressure differential (9) between opposite sides of the first valve (52) and the second valve (56). Regardless of the configuration of the fluid flow generator (2), the pressure differential (9) between opposite sides of the first valve (52) can be such that a fluid pressure (75) in the first portion (53) of the first fluid flow conduit (49) can be greater than the fluid pressure (75) in the second portion (54) of the first fluid flow conduit (49). This pressure differential (9) can be sufficient to generate the open condition (69) of the first valve (52). The pressure differential (9) between opposite sides of the second valve (56) can be such that the fluid pressure (75) in the first portion (53) of the first fluid flow conduit (49) can be greater than the ambient pressure (11), which can be sufficient to generate the closed condition (68) of the second valve (56). The open condition (69) of the first valve (52) and the closed condition (68) of the second valve (56) can result in a fluid flow (8) in the first direction (47) in the first fluid flow conduit (49) which flows from the fluid flow generator (2) through the axial earpiece bore (4) to egress from the earpiece second end (29) into the external ear canal (6), thus increasing the external ear canal pressure (10) to greater than the ambient pressure (11).

As shown in FIG. 11C, continued operation of the fluid flow generator (2) can further act to reduce the pressure differential (9) between opposite sides of the first valve (52) and the second valve (56), for example by allowing the resiliently flexible wall (16) of the volumetrically adjustable element (13) to return toward the non-deformed condition (21). The pressure differential (9) between opposite sides of the first valve (52) can be such that the fluid pressure (75) in the first portion (53) of the first fluid flow conduit (49) can be lesser than the fluid pressure (75) in the second portion (54) of the first fluid flow conduit (49). This pressure differential (9) can be sufficient to generate the closed condition (68) of the first valve (52), thus interrupting the fluid flow (8) in the first fluid flow conduit (49) from the axial earpiece bore (4) toward the fluid flow generator (2) and thereby correspondingly maintaining the pressure differential (9) between the external ear canal pressure (10) and the ambient pressure (11).

Again referring to FIG. 11C, continued reduction in fluid pressure (75) within the first portion (53) of the first fluid flow conduit (49) can result in a pressure differential (9) between opposite sides of the second valve (56) such that the fluid pressure (75) in the first portion (53) of the first fluid flow conduit (49) can be lesser than the ambient pressure (11), which can be sufficient to generate the open condition (69) of the second valve (56). As such, a fluid flow (8) can be generated from the ambient pressure (11) through the second fluid flow conduit (55) toward the fluid flow generator (2). As to those embodiments having a volumetrically adjustable element (13), the fluid flow (8) from the ambient pressure (11) toward the fluid flow generator (2) can allow the resiliently flexible wall (16) to return toward the non-deformed condition (21) by increasing the internal volume (19). As to those embodiments having a piston (27) which reciprocally operates in a barrel (28), the fluid flow (8) through the second fluid flow conduit (55) from the ambient pressure (11) toward the fluid flow generator (2) can allow the piston (27) to return to a location within the barrel (28) which increases the barrel internal volume.

Now referring to FIG. 11D, the third valve (58) in the closed condition (68) can remain substantially leak-tight to fluid flow (8) in the third fluid flow conduit (57) up to about a 50 kilopascal pressure differential amplitude (59) between the external ear canal pressure (10) and the ambient pressure (11). Accordingly, the external ear canal pressure regulation device (1) can be operated to achieve a desired external ear canal pressure (10) greater than the ambient pressure (11) or to achieve a pre-selected external ear canal pressure (10) greater than the ambient pressure (11), beyond which results in the open condition (69) of the third valve (58), allowing a fluid flow (8) from the external ear canal pressure (10) toward ambient pressure (11) to maintain the desired or pre-selected external ear canal pressure (10).

Now referring primarily to FIG. 5 and FIG. 11D, the third valve (58) can be operably coupled to a third valve pressure relief element (72) configured to allow manual operation of the third valve (58) between the closed condition (68) and the open condition (69), facilitating the return of the external ear canal pressure (10) toward the ambient pressure (11).

Now referring primarily to FIG. 2B, FIG. 6, and FIG. 12A through FIG. 12D, as to particular embodiments, the external ear canal pressure regulation device (1) can be configured to achieve an external ear canal pressure (10) which can be lesser than the ambient pressure (11). As such, the valved conduit (5) can be coupled to the fluid flow generator (2) and the axial earpiece bore (4) of the earpiece (3) in the second configuration (46) to unidirectionally regulate the fluid flow (8) in the second direction (48) in the first fluid flow conduit (49) to ingress to the axial earpiece bore (4) from the external ear canal (6) toward the fluid flow generator (2).

As shown in FIG. 12A and FIG. 12B, the earpiece external surface (7) of the earpiece (3) can be sealably engaged with the external ear canal (6) as described above. Operation of the fluid flow generator (2) can compress an amount of fluid (74) in the first portion (53) of the first fluid flow conduit (49). As to those embodiments including a volumetrically adjustable element (13), the resiliently flexible wall (16) can be deformed to reduce the internal volume (19) of the volumetrically adjustable element (13) to compress the amount of fluid (74) in the first portion (53) of the first fluid flow conduit (49), resulting in a pressure differential (9) between opposite sides of the first valve (52) and the second valve (56). As to those embodiments including a piston (27) which reciprocally operates in a barrel (28), the piston (27) can travel within the barrel (28) to reduce the barrel internal volume, thus resulting in a pressure differential (9) between opposite sides of the first valve (52) and the second valve (56). Regardless of the configuration of the fluid flow generator (2), the pressure differential (9) between opposite sides of the first valve (52) can be such that a fluid pressure (75) in the first portion (53) of the first fluid flow conduit (49) can be greater than the fluid pressure (75) in the second portion (54) of the first fluid flow conduit (49). This pressure differential (9) can be sufficient to generate the closed condition (68) of the first valve (52). The pressure differential (9) between opposite sides of the second valve (56) can be such that the fluid pressure (75) in the first portion (53) of the first fluid flow conduit (49) can be greater than the ambient pressure (11), which can be sufficient to generate the open condition (69) of the second valve (56), which can generate a fluid flow (8) in the second fluid flow conduit (55) from the fluid flow generator (2) toward the ambient pressure (11).

As shown in FIG. 12C, continued operation of the fluid flow generator (2) can further act to reduce the pressure differential (9) between opposite sides of the first valve (52) and the second valve (56), for example by allowing the resiliently flexible wall (16) of the volumetrically adjustable element (13) to return toward the non-deformed condition (21). The pressure differential (9) between opposite sides of the first valve (52) can be such that the fluid pressure (75) in the first portion (53) of the first fluid flow conduit (49) can be lesser than the fluid pressure (75) in the second portion (54) of the first fluid flow conduit (49). This pressure differential (9) can be sufficient to generate the open condition (69) of the first valve (52), which can result in a fluid flow (8) from the external ear canal (6) toward the fluid flow generator (2), thus decreasing the external ear canal pressure (10) to lesser than the ambient pressure (11).

Again referring to FIG. 12C, continued reduction in fluid pressure (75) within the first portion (53) of the first fluid flow conduit (49) can result in a pressure differential (9)

between opposite sides of the second valve (56) such that the fluid pressure (75) in the first portion (53) of the first fluid flow conduit (49) can be lesser than the ambient pressure (11), which can be sufficient to generate the closed condition (68) of the second valve (56), thus interrupting the fluid flow (8) in the second fluid flow conduit (55) from the fluid flow generator (2) toward the ambient pressure (11) and correspondingly maintaining the pressure differential (9) between the external ear canal pressure (10) and the ambient pressure (11).

As to those embodiments having a volumetrically adjustable element (13), the fluid flow (8) from the external ear canal (6) toward the fluid flow generator (2) can allow the resiliently flexible wall (16) to return toward the non-deformed condition (21) by increasing the internal volume (19). As to those embodiments having a piston (27) which reciprocally operates in a barrel (28), the fluid flow (8) through the first fluid flow conduit (49) from the external ear canal (6) toward the fluid flow generator (2) can allow the piston (27) to return to a location within the barrel (28) which increases the barrel internal volume.

Now referring to FIG. 12D, the third valve (58) in the closed condition (68) can remain substantially leak-tight to fluid flow (8) in the third fluid flow conduit (57) up to about a 50 kilopascal pressure differential amplitude (59) between the external ear canal pressure (10) and the ambient pressure (11). Accordingly, the external ear canal pressure regulation device (1) can be operated to achieve a desired external ear canal pressure (10) lesser than the ambient pressure (11) or to achieve a pre-selected external ear canal pressure (10) lesser than ambient pressure (11), beyond which results in the open condition (69) of the third valve (58), allowing a fluid flow (8) from the ambient pressure (11) toward the external ear canal (6) to maintain the desired or pre-selected external ear canal pressure (10).

Now referring primarily to FIG. 6 and FIG. 12D, the third valve (58) can be operably coupled to a third valve pressure relief element (72) configured to allow manual operation of the third valve (58) between the closed condition (68) and the open condition (69), facilitating the return of the external ear canal pressure (10) toward the ambient pressure (11).

Now referring primarily to FIG. 13A through FIG. 13F, a particular embodiment of the external ear canal pressure regulation device (1) can include a fluid flow generator (2) configured as a diaphragm (15), which has a resiliently flexible wall (16) having a wall external surface (17) and a wall internal surface (18), which defines an internal volume (19) (whether in whole or in part as an assembly with the valved conduit (5)). The resiliently flexible wall (16) in a deformed condition (20) can decrease the internal volume (19), and in return toward a non-deformed condition (21), can increase the internal volume (19). The change in the internal volume (19) can generate a fluid flow (8) between the fluid flow generator (2) and an axial earpiece bore (4) of an earpiece (3), which can be regulated by a valved conduit (5).

Again referring primarily to FIG. 13A through FIG. 13F, the external ear canal pressure regulation device (1) can include a valved conduit (5) fluidically coupled between the fluid flow generator (2) and the axial earpiece bore (4). As to particular embodiments, the earpiece (3) having the axial earpiece bore (4) and first, second, and third fluid flow conduits (49)(55)(57) can be included in a conduit body (41) having a configuration which removably couples to the fluid flow generator (2) and the first, second, and third valves (52)(56)(58). As to particular embodiments, the first and second valves (52)(56) can be included in a first valve assembly (83), which can be fluidicly coupled between the fluid flow generator (2) and the first and second fluid flow conduits (49)(55) to interrupt the fluid flow (8) between the fluid flow generator (2) and the first and second fluid flow conduits (49)(55), thereby unidirectionally regulating the fluid flow (8) in the first and second fluid flow conduits (49)(55).

The third valve (58) can be included in a second valve assembly (84), which can be fluidicly coupled to a third fluid flow conduit (57) communicating between the first fluid flow conduit (49) and the ambient pressure (11) to interrupt the fluid flow (8) between the third fluid flow conduit (57) and the ambient pressure (11), thereby unidirectionally regulating the fluid flow (8) in the third fluid flow conduit (57) between the first fluid flow conduit (49) and the ambient pressure (11). As to particular embodiments, the fluid flow generator (2) and the first and second valve assemblies (83)(84) can be provided as a one-piece construct. As to other particular embodiments, the fluid flow generator (2), the first valve assembly (83), and the second valve assembly (84) can be provided as a plurality of pieces which can be assembled into a configuration capable of removably coupling to the conduit body (41).

As to particular embodiments, the first and second valves (52)(56) included in the first valve assembly (83) can have any type of valve configuration, as described above, which can operate between a closed condition (68) and an open condition (69) to unidirectionally regulate fluid flow (8) in a pre-selected range. As an illustrative example, the first and second valves (52)(56) included in the first valve assembly (83) can both be configured as flapper valves (64) having hinges (94) (as shown in the example of FIG. 3B, and FIG. 13C though FIG. 13F) having opposing configurations.

As to particular embodiments, the second valve assembly (84) can be operable to allow the external ear canal pressure (10) to return toward the ambient pressure (11). The second valve assembly (84) can include a resiliently deformable annular member (85) and a pressure relief element (70) configured as a deformation member (86) capable of deforming the resiliently deformable annular member (85). The resiliently deformable annular member (85) can have an annular member external surface (87) which can be disposed adjacent to and sealably engage with the conduit internal surface (88) of the first fluid flow conduit (49).

An annular member aperture element (89) communicating between an annular member internal surface (90) and the annular member external surface (87) can align with the axial earpiece bore (4) to form a pass-through (91) between the first fluid flow conduit (49) and the axial earpiece bore (4). The deformation member (86) can be disposed through the third fluid flow conduit (57) communicating between the first fluid flow conduit (49) and the ambient pressure (11) such that a deformation member first end (92) can extend outward from the third fluid flow conduit (57) and the conduit body (41) and a deformation member second end (93) can deformably engage the annular member external surface (87). Upon gripping engagement of the deformation member first end (92), the deformation member (86) can be urged toward the resiliently deformable annular member (85) to deform the resiliently deformable annular member (85) such that the annular member external surface (87) disengages from the conduit internal surface (88) of the first fluid flow conduit (49), thereby positioning the third valve (58) in the open condition (69) to allow the fluid flow (8) to flow between the axial earpiece bore (4), the first and third fluid flow conduits (49)(57), and the ambient pressure (11). As such, the third valve (58) in the open condition (69) can generate a fluid flow (8) between the external ear canal (6) and the ambient pressure (11) to return the external ear canal pressure (10) toward the ambient pressure (11), whether from an external ear canal pressure (10) greater than the ambient pressure (11) or an external ear canal pressure (10) lesser than the ambient pressure (11).

The fluid flow generator (2), the first valve assembly (83), and the second valve assembly (84) can be removably coupled to the conduit body (41) in either one of a first configuration (45) or a second configuration (46). The releasably couplable surfaces (44) of the conduit body (41), the fluid flow generator (2), the first valve assembly (83), and the second valve assembly (84) can have sufficiently similar configurations to allow the conduit body (41) to removably couple to the fluid flow generator (2), the first valve assembly (83), and the second valve assembly (84) in either one of the first configuration (45) or the second configuration (46) depending upon whether the valved conduit (5) operates to achieve a pressure differential (9) having the external ear canal pressure (10) greater than the ambient pressure (11) (as shown in the example of FIG. 13E) or whether the valved conduit (5) operates to achieve a pressure differential (9) having the external ear canal pressure (10) lesser than ambient the pressure (11) (as shown in the example of FIG. 13F). As to particular embodiments, to removably couple, the releasably couplable surfaces (44) of the conduit body (41), the fluid flow generator (2), the first valve assembly (83), and the second valve assembly (84) can matably engage.

As to the particular embodiments of the external ear canal pressure regulation device (1) described herein, the first and second valves (52)(56) fluidicly couple to the corresponding first and second fluid flow conduits (49)(55) to interrupt the fluid flow (8) within the corresponding first and second fluid flow conduits (49)(55), whether the conduit body (41) can be positioned in the first configuration (45) or the second configuration (46).

Now referring primarily to FIG. 13E, as an illustrative example, the fluid flow generator (2), the first valve assembly (83), and the conduit body (41) can be positioned in the first configuration (45) by removably coupling the fluid flow generator (2) and the first valve assembly (83) to the conduit body (41). In the first configuration (45), the first valve (52) can be operable to unidirectionally regulate the fluid flow (8) in the first fluid flow conduit (49), whereby the first valve (52) in the open condition (69) allows the fluid flow (8) to flow from the fluid flow generator (2) toward the axial earpiece bore (4) and, in the closed condition (68), precludes the fluid flow (8) from flowing between the fluid flow generator (2) and the axial earpiece bore (4). As such, the fluid flow (8), generated by deforming the resiliently flexible wall (16) of the diaphragm (15) to decrease the internal volume (19), can be regulated in a first direction (47) in the first fluid flow conduit (49) to egress from the axial earpiece bore (4) toward the external ear canal (6), thereby achieving a pressure differential (9) having the external ear canal pressure (10) greater than the ambient pressure (11). Upon achieving the desired pressure differential (9) between the external ear canal pressure (10) and the ambient pressure (11), the resiliently flexible wall (16) of the diaphragm (15) can be allowed to return to the non-deformed condition (21), thereby closing the first valve (52) and precluding the fluid flow (8) from flowing from the axial earpiece bore (4) toward the fluid flow generator (2), thereby maintaining the desired pressure differential (9).

In the first configuration (45), the second valve (56) can be operable to unidirectionally regulate the fluid flow (8) in the second fluid flow conduit (55), whereby the second valve (56) in the open condition (69) allows the fluid flow (8) to flow from the ambient pressure (11) toward the fluid flow generator (2) and, in the closed condition (68), precludes the fluid flow (8) from flowing between the ambient pressure (11) and the fluid flow generator (2).

As such, the fluid flow (8), generated upon return of the resiliently flexible wall (16) of the diaphragm (15) to the non-deformed condition (21) to increase the internal volume (19), can be regulated in the second fluid flow conduit (55) to ingress from the ambient pressure (11) toward the fluid flow generator (2), thereby maintaining the desired pressure differential (9) between the external ear canal pressure (10) and the ambient pressure (11) while allowing the resiliently flexible wall (16) of the diaphragm (15) to return toward the non-deformed condition (21).

As to particular embodiments, the fluid flow generator (2), the first valve assembly (83), and the conduit body (41) in the first configuration (45) can further include the second valve assembly (84), positioned such that the third valve (58) can be fluidicly coupled to the third fluid flow conduit (57) communicating between the first fluid flow conduit (49) and the ambient pressure (11) to unidirectionally regulate the fluid flow (8) in the third fluid flow conduit (57) between the first fluid flow conduit (49) and the ambient pressure (11). The third valve (58) in the open condition (69) allows the fluid flow (8) to flow from the axial earpiece bore (4), through the first and third fluid flow conduits (49)(57), and toward the ambient pressure (11) and, in the closed condition (68), precludes the fluid flow (8) from flowing between the axial earpiece bore (4) and the ambient pressure (11). As such, the third valve (58) in the open condition (69) can generate a fluid flow (8) from the external ear canal (6) toward the ambient pressure (11) to return the external ear canal pressure (10) toward the ambient pressure (11).

As to particular embodiments, the fluid flow generator (2), the first valve assembly (83), and the second valve assembly (84) can be removed from the conduit body (41) to disassemble the first configuration (45). The first valve assembly (83) can be rotated without any structural alteration to reverse orientation of the first valve assembly (83) in relation to the conduit body (41), thereby achieving the second configuration (46).

Now referring primarily to FIG. 13F, as an illustrative example, the fluid flow generator (2), the first valve assembly (83), and the conduit body (41) can be positioned in the second configuration (46) as described above. In the second configuration (46), the second valve (56) can be operable to unidirectionally regulate the fluid flow (8) in the second fluid flow conduit (55), whereby the second valve (56) in the open condition (69) allows the fluid flow (8) to flow from the fluid flow generator (2) toward the ambient pressure (11) and, in the closed condition (68), precludes the fluid flow (8) from flowing between the fluid flow generator (4) and the ambient pressure (11). As such, the fluid flow (8), generated by deforming the resiliently flexible wall (16) of the diaphragm (15) to decrease the internal volume (19), can be regulated in the second fluid flow conduit (55) to egress from the second fluid flow conduit (55) toward the ambient pressure (11). The resiliently flexible wall (16) of the diaphragm (15) can be allowed to return to the non-deformed condition (21), thereby closing the second valve (56) and precluding the fluid flow (8) from flowing between the fluid flow generator (2) and the ambient pressure (11).

In the second configuration (46), the first valve (52) can be operable to unidirectionally regulate the fluid flow (8) in the first fluid flow conduit (49), whereby the first valve (52)

in the open condition (69) allows the fluid flow (8) to flow from the axial earpiece bore (4) toward the fluid flow generator (2) and, in the closed condition (68), precludes the fluid flow (8) from flowing between the axial earpiece bore (4) and the fluid flow generator (2).

As such, the fluid flow (8), generated upon return of the resiliently flexible wall (16) of the diaphragm (15) to the non-deformed condition (21) to increase the internal volume (19), can be regulated in a second direction (48) in the first fluid flow conduit (56) to ingress from the external ear canal (6) to the axial earpiece bore (4) toward the fluid flow generator (2), thereby achieving a pressure differential (9) having the external ear canal pressure (10) lesser than the ambient pressure (11). Upon achieving the desired pressure differential (9) between the external ear canal pressure (10) and the ambient pressure (11), the first valve (52) can return toward the closed condition (68), precluding the fluid flow (8) from flowing between the axial earpiece bore (4) and the fluid flow generator (2), thereby maintaining the desired pressure differential (9) between the external ear canal pressure (10) and the ambient pressure (11).

As to particular embodiments, the fluid flow generator (2), the first valve assembly (83), and the conduit body (41) in the second configuration (46) can further include the second valve assembly (84), positioned such that the third valve (58) can be fluidicly coupled to the third fluid flow conduit (57) communicating between the first fluid flow conduit (49) and the ambient pressure (11) to unidirectionally regulate the fluid flow (8) in the third fluid flow conduit (57) between the first fluid flow conduit (49) and the ambient pressure (11). The third valve (58) in the open condition (69) allows the fluid flow (8) to flow from the ambient pressure (11), through the third and first fluid flow conduits (57)(49), and toward the axial earpiece bore (4) and, in the closed condition (68), precludes the fluid flow (8) from flowing between the ambient pressure (11) and the axial earpiece bore (4). As such, the third valve (58) in the open condition (69) can generate a fluid flow (8) from the ambient pressure (11) toward the external ear canal (6) to return the external ear canal pressure (10) toward the ambient pressure (11).

Now referring primarily to FIG. 14A through FIG. 15G, which show a pressure differential (9) between the external ear canal pressure (10) and the ambient pressure (11) achieved over a time period (76) by operation of embodiments of the external ear canal pressure regulation device (1). As to particular embodiments, a fluid flow generator (2) comprising a volumetrically adjustable element (13) can be operated from a non-deformed condition (21) toward a deformed condition (20) to generate a fluid flow (8) in a first direction (47) which egresses from the axial earpiece bore (4) toward the external ear canal (6) over a time period (76), resulting in a positive external ear canal pressure (10) relative to the ambient pressure (11) (as shown in the examples of FIG. 14A through FIG. 14G). As to other particular embodiments, a fluid flow generator (2) comprising a volumetrically adjustable element (13) can be operated from a deformed condition (20) toward a non-deformed condition (21) to generate a fluid flow (8) in a second direction (48) which ingresses to the axial earpiece bore (4) from the external ear canal (6) toward the fluid flow generator (2) over a time period (76), resulting in a negative external ear canal pressure (10) relative to the ambient pressure (11) (as shown in the examples of FIG. 15A through FIG. 15G).

Now referring primarily to FIG. 14A and FIG. 15A, the fluid flow generator (2) can be operated to maintain a constant pressure amplitude (77) over a time period (76). As to particular embodiments, a constant pressure amplitude (77) can be maintained substantially without fluid flow (8) of a fluid volume (12) within the external ear canal (6) over the time period (76). As an illustrative example, the external ear canal pressure regulation device (1) having the earpiece external surface (7) sealably engaged with the external ear canal (6), as described above, can be operated by manipulating the fluid flow generator (2) to generate a fluid flow (8) of a fluid volume (12) between the fluid flow generator (2) and the external ear canal (6) through the axial earpiece bore (4) of the earpiece (3) to achieve a pressure differential (9) between the external ear canal pressure (10) and the ambient pressure (11). Once the desired pressure differential (9) between the external ear canal pressure (10) and the ambient pressure (11) has been achieved, the pressure amplitude (77) can be maintained for a time period (76) without additional fluid flow (8) of the fluid volume (12), for example by operation of the first valve (52) configured to allow unidirectional fluid flow (8) of the fluid volume (12) through the first fluid flow conduit (49) such that the fluid volume (12) can only either ingress or egress from the external ear canal (6). As to other embodiments, once the desired pressure differential (9) between the external ear canal pressure (10) and the ambient pressure (11) has been achieved, the pressure amplitude (77) can be maintained for a time period (76) by additional fluid flow (8) of a fluid volume (12) to or from the external ear canal (6) to offset leakage about engagement of the earpiece external surface (7) with the external ear canal (6). As to other embodiments, the pressure amplitude (77) can be maintained for a time period (76) by continuous fluid flow (8) of a fluid volume (12) in the external ear canal (6).

The constant pressure amplitude (77) can be maintained over a time period (76) to alleviate a disorder symptom or treat a disorder, whereby the constant pressure amplitude (77) can be in a range of between about +50 kilopascals above the ambient pressure (11) to about −50 kilopascals below the ambient pressure (11). A positive external ear canal pressure (10) relative to the ambient pressure (11) can be achieved by maintaining the constant pressure amplitude (77) in a range of between about 0 kilopascals to about +50 kilopascals above the ambient pressure (11). Alternatively, a negative external ear canal pressure (10) relative to the ambient pressure (11) can be achieved by maintaining the constant pressure amplitude (77) in a range of between about −50 kilopascals to about 0 kilopascals below the ambient pressure (11).

Now referring primarily to FIG. 14B through FIG. 14G and FIG. 15B through FIG. 15G, the fluid flow generator (2) can be configured for repeated operation to generate a fluid flow (8) having a pressure wave (78) including a pressure wave amplitude (77) and a pressure wave frequency (79). As to particular embodiments, a fluid flow generator (2) comprising a volumetrically adjustable element (13) can be operated from a non-deformed condition (21) toward a deformed condition (20) to generate a fluid flow (8) which egresses from the axial earpiece bore (4) toward the external ear canal (6) over a time period (76), whereby the fluid flow (8) has a pressure wave (78) including a pressure wave amplitude (77) and a pressure wave frequency (79) which results in a positive external ear canal pressure (10) relative to the ambient pressure (11) (as shown in the examples of FIG. 14B through FIG. 14G). As to other particular embodiments, a fluid flow generator (2) comprising a volumetrically adjustable element (13) can be operated from a deformed condition (20) toward a non-deformed condition (21) to generate a fluid flow (8) which ingresses to the axial earpiece bore (4) from the external ear canal (6) toward the fluid flow generator (2) over a time period (76), whereby the fluid flow (8) has a pressure wave (78) including a pressure wave amplitude (77) and a pressure wave frequency (79) which results in a negative external ear canal pressure (10) relative to the ambient pressure (11) (as shown in the examples of FIG. 15B through FIG. 15G).

Again referring primarily to FIG. 14A through FIG. 15G, the fluid flow generator (2) can be configured for repeated operation to generate a fluid flow (8) having a pressure wave (78) including a pressure wave amplitude (77) as described above and a pressure wave frequency (79) typically in a range of between 0 Hertz to about 10 Hertz; however, embodiments can have a lesser or greater pressure wave frequency (79) depending upon the application. As to particular embodiments, one or more pressure wave frequencies (79) can be selected from the group including or consisting of: between 0 Hertz to about 1 Hertz, between about 0.5 Hertz to about 1.5 Hertz, between about 1 Hertz to about 2 Hertz, between about 1.5 Hertz to about 2.5 Hertz, between about 2 Hertz to about 3 Hertz, between about 2.5 Hertz to about 3.5 Hertz, between about 3 Hertz to about 4 Hertz, between about 3.5 Hertz to about 4.5 Hertz, between about 4 Hertz to about 5 Hertz, between about 4.5 Hertz to about 5.5 Hertz, between about 5 Hertz to about 6 Hertz, between about 5.5 Hertz to about 6.5 Hertz, between about 6 Hertz to about 7 Hertz, between about 6.5 Hertz to about 7.5 Hertz, between about 7 Hertz to about 8 Hertz, between about 7.5 Hertz to about 8.5 Hertz, between about 8 Hertz to about 9 Hertz, between about 8.5 Hertz to about 9.5 Hertz, and between about 9 Hertz to about 10 Hertz.

One or more pressure wave frequencies (79) can be generated with the external ear canal pressure regulation device (1) depending upon the method of use, which can be further influenced by factors such as user (23) anatomy, physiology, or biochemistry of the auditory meatus (24); disorder symptom targeted for alleviation; disorder targeted for treatment; observable effect(s) of using one or more pressure wave frequencies (79) in a particular method of using the external ear canal pressure regulation device (1); or the like; or combinations thereof; but not so much as to cause discomfort to the user (23) or injury to the auditory meatus (24) or the tympanic membrane (25).

The pressure wave (78) can oscillate with a desired pressure wave frequency (79) within only positive pressure amplitudes (77) in a range of between 0 kilopascals to about +50 kilopascals above the ambient pressure (11) (as shown in the examples of FIG. 14B through FIG. 14G), which can correspondingly generate a positive external ear canal pressure (10) relative to the ambient pressure (11) by increasing the external ear canal pressure (10) relative to the ambient pressure (11), for example to alleviate a disorder symptom or treat a disorder. As to yet other particular embodiments, the pressure wave (78) can oscillate with a desired pressure wave frequency (79) within only negative pressure amplitudes (77) in a range of between about −50 kilopascals to 0 kilopascals below the ambient pressure (11) (as shown in the examples of FIG. 15B through FIG. 15G), which can correspondingly generate a negative external ear canal pressure (10) relative to the ambient pressure (11) by decreasing the external ear canal pressure (10) relative to the ambient pressure (11), for example to alleviate a disorder symptom or treat a disorder.

Again referring primarily to FIG. 14B through FIG. 15G, the pressure wave (78) can have a numerous and wide variety of waveforms, depending upon the application, corresponding to the numerous and wide variety of symptoms which can be alleviated or disorders which can be treated by operation of the external ear canal pressure regulation device (1). As illustrative examples, the pressure wave (78) can be sine wave having smooth repetitive periodic oscillations (as shown in the example of FIG. 14B and FIG. 15B), a square wave in which the pressure amplitude (77) alternates at a steady frequency between fixed minimum and maximum values, a rectangular wave, a trapezoidal wave or a truncated wave in which the apex of the pressure wave (78) has a constant pressure amplitude (77) over a time period (76) (as shown in the example of FIG. 14C, FIG. 15C, FIG. 14F, and FIG. 15F), a triangle wave having linear leading and trailing edges (as shown in the example of FIG. 14D and FIG. 15D), a sawtooth wave in which the leading edge changes pressure amplitude (77) over a time period (76) which is greater than the time period (76) in which the trailing edge changes pressure amplitude (77) (as shown in the example of FIG. 14E), a reverse sawtooth wave in which the leading edge changes pressure amplitude (77) over a time period (76) which is lesser than the time period (76) in which the trailing edge changes pressure amplitude (77) (as shown in the example of FIG. 15E), or combinations thereof (as shown in the example of FIG. 14G and FIG. 15G).

As to particular embodiments, the fluid flow generator (2) and the third valve pressure relief element (72) coupled to the third valve (58) can be alternately repeatedly operated to generate a fluid flow (8) having a pressure wave (78) including a pressure wave amplitude (77) and a pressure wave frequency (79).

Now referring primarily to FIG. 14A through FIG. 14G, which show a pressure differential (9) between the external ear canal pressure (10) and the ambient pressure (11) achieved over a time period (76) by operation of embodiments of the external ear canal pressure regulation device (1) to generate a positive external ear canal pressure (10) relative to the ambient pressure (11) (as shown in the examples of FIG. 2A, FIG. 5, and FIG. 11A through FIG. 11D). The particular embodiment of the external ear canal pressure regulation device (1) includes a third valve (58) which remains substantially leak-tight to fluid flow (8) in the third fluid flow conduit (57) up to about a 50 kilopascal pressure differential amplitude (59) between the external ear canal pressure (10) and the ambient pressure (11) (represented in each graph as having a pressure amplitude (77) of zero). However, this need not limit embodiments solely to those capable of generating a positive external ear canal pressure (10) relative to the ambient pressure (11) pre-selected to a maximum of +50 kilopascals. Other embodiments can operate to generate a positive external ear canal pressure (10) relative to the ambient pressure (11) which can be any amount greater than the ambient pressure (11), but not an amount so great as to cause discomfort to the user (23) or injury to the auditory meatus (24) or the tympanic membrane (25).

Now referring primarily to FIG. 14A, as to a particular embodiment, the fluid flow generator (2) can be operated to generate an external ear canal pressure (10) having a maximum pressure amplitude (77) of up to about +50 kilopascals above the ambient pressure (11). The external ear canal pressure (10) can be maintained for a time period (76) at about +50 kilopascals above the ambient pressure (11). After elapse of the time period (76), the third valve pressure relief element (72) can be operated to return the external ear canal pressure (10) toward the ambient pressure (11). The operation can be, but is not necessarily, repeated.

Now referring primarily to FIG. 14B, as to a particular embodiment, the fluid flow generator (2) can be operated to generate an external ear canal pressure (10) having a maximum pressure amplitude (77) of up to about +50 kilopascals above the ambient pressure (11). The third valve pressure relief element (72) can be operated to return the external ear canal pressure (10) toward the ambient pressure (11), whereby the pressure wave (78) can be a sine wave having smooth repetitive periodic oscillations. The operation can be repeated to administer a pulsatile change in the external ear canal pressure (10).

Now referring primarily to FIG. 14D, as to a particular embodiment, the fluid flow generator (2) can be operated to generate an external ear canal pressure (10) having a maximum pressure amplitude (77) of up to about +50 kilopascals above the ambient pressure (11). The third valve pressure relief element (72) can be operated to return the external ear canal pressure (10) toward the ambient pressure (11), whereby the pressure wave (78) can be a triangle wave having linear leading and trailing edges. The operation can be repeated to administer a pulsatile change in the external ear canal pressure (10).

Now referring primarily to FIG. 14E, as to a particular embodiment, the fluid flow generator (2) can be operated to generate an external ear canal pressure (10) having a maximum pressure amplitude (77) of up to about +50 kilopascals above the ambient pressure (11). The third valve pressure relief element (72) can be operated to return the external ear canal pressure (10) toward the ambient pressure (11), whereby the pressure wave (78) can be a sawtooth wave in which the leading edge changes pressure amplitude (77) over a time period (76) which is greater than the time period (76) in which the trailing edge changes pressure amplitude (77). The operation can be repeated to administer a pulsatile change in the external ear canal pressure (10).

Now referring primarily to FIG. 14C and FIG. 14F, as to a particular embodiment, the fluid flow generator (2) can be operated to generate an external ear canal pressure (10) having a maximum pressure amplitude (77) of up to about +50 kilopascals above the ambient pressure (11). The external ear canal pressure (10) can be maintained for a time period (76) at about +50 kilopascals above the ambient pressure (11). After elapse of the time period (76), the third valve pressure relief element (72) can be operated to return the external ear canal pressure (10) toward the ambient pressure (11). The operation can be repeated to administer a pulsatile change in the external ear canal pressure (10).

Now referring primarily to FIG. 14G, as to a particular embodiment, the fluid flow generator (2) can be operated to increase the external ear canal pressure (10) in a series of incremental pressure increases having a maximum pressure amplitude (77) of about +50 kilopascals above the ambient pressure (11). Each of the series of incremental pressure increases can increase the external ear canal pressure (10) by about 10 kilopascals to about 15 kilopascals above the ambient pressure (11), with each incremental pressure increase in the external ear canal pressure (10) maintained for a time period (76). After achieving the maximum pressure amplitude (77) of about +50 kilopascals above the ambient pressure (11) and elapse of the time period (76), the third valve pressure relief element (72) can be operated to return the external ear canal pressure (10) toward the ambient pressure (11). The operation can be repeated to administer a pulsatile change in the external ear canal pressure (10).

Now referring primarily to FIG. 15A through FIG. 15G, which show a pressure differential (9) between the external ear canal pressure (10) and the ambient pressure (11) achieved over a time period (76) by operation of embodiments of the external ear canal pressure regulation device (1) to generate a negative external ear canal pressure (10) relative to the ambient pressure (9) (as shown in the examples of FIG. 2B, FIG. 6, and FIG. 12A through FIG. 12D). The particular embodiment of the external ear canal pressure regulation device (1) includes a third valve (58) which remains substantially leak-tight to fluid flow (8) in the third fluid flow conduit (57) up to about a 50 kilopascal pressure differential amplitude (59) between the external ear canal pressure (10) and the ambient pressure (11) (represented in each graph as having a pressure amplitude (77) of zero). However, this need not limit embodiments solely to those capable of generating a negative external ear canal pressure (10) relative to the ambient pressure (77) preselected to a maximum of −50 kilopascals. Other embodiments can operate to generate a negative external ear canal pressure (10) relative to the ambient pressure (11) which can be any amount lesser than the ambient pressure (11), but not an amount so great as to cause discomfort to the user (23) or injury to the auditory meatus (24) or the tympanic membrane (25).

Now referring primarily to FIG. 15A, as to a particular embodiment, the fluid flow generator (2) can be operated to generate an external ear canal pressure (10) having a maximum pressure amplitude (77) of up to about −50 kilopascals below the ambient pressure (11). The external ear canal pressure (10) can be maintained for a time period (76) at about −50 kilopascals below the ambient pressure (11). After elapse of the time period (76), the third valve pressure relief element (72) can be operated to return the external ear canal pressure (10) toward the ambient pressure (11). The operation can be, but is not necessarily, repeated.

Now referring primarily to FIG. 15B, as to a particular embodiment, the fluid flow generator (2) can be operated to generate an external ear canal pressure (10) having a maximum pressure amplitude (77) of up to about −50 kilopascals below the ambient pressure (11). The third valve pressure relief element (72) can be operated to return the external ear canal pressure (10) toward the ambient pressure (11), whereby the pressure wave (78) can be a sine wave having smooth repetitive periodic oscillations. The operation can be repeated to administer a pulsatile change in the external ear canal pressure (10).

Now referring primarily to FIG. 15D, as to a particular embodiment, the fluid flow generator (2) can be operated to generate an external ear canal pressure (10) having a maximum pressure amplitude (77) of up to about −50 kilopascals below the ambient pressure (11). The third valve pressure relief element (72) can be operated to return the external ear canal pressure (10) toward the ambient pressure (11), whereby the pressure wave (78) can be a triangle wave having linear leading and trailing edges. The operation can be repeated to administer a pulsatile change in the external ear canal pressure (10).

Now referring primarily to FIG. 15E, as to a particular embodiment, the fluid flow generator (2) can be operated to generate an external ear canal pressure (10) having a maximum pressure amplitude (77) of up to about −50 kilopascals below the ambient pressure (11). The third valve pressure relief element (72) can be operated to return the external ear canal pressure (10) toward the ambient pressure (11), whereby the pressure wave (78) can be a reverse sawtooth wave in which the leading edge changes pressure amplitude (77) over a time period (76) which is lesser than the time period (76) in which the trailing edge changes pressure amplitude (77). The operation can be repeated to administer a pulsatile change in the external ear canal pressure (10).

Now referring primarily to FIG. 15C and FIG. 15F, as to a particular embodiment, the fluid flow generator (2) can be operated to generate an external ear canal pressure (10) having a maximum pressure amplitude (77) of up to about −50 kilopascals below the ambient pressure (11). The external ear canal pressure (10) can be maintained for a time period (76) at about −50 kilopascals below the ambient pressure (11). After elapse of the time period (76), the third valve pressure relief element (72) can be operated to return the external ear canal pressure (10) toward the ambient pressure (11). The operation can be repeated to administer a pulsatile change in the external ear canal pressure (10).

Now referring primarily to FIG. 15G, as to a particular embodiment, the fluid flow generator (2) can be operated to decrease the external ear canal pressure (10) in a series of incremental pressure decreases having a maximum pressure amplitude (77) of about −50 kilopascals below the ambient pressure (11). Each of the series of incremental pressure decreases can decrease the external ear canal pressure (10) by about −10 kilopascals to about −15 kilopascals below the ambient pressure (11), with each incremental pressure decrease in the external ear canal pressure (10) maintained for a time period (76). After achieving the maximum pressure amplitude (77) of about −50 kilopascals below the ambient pressure (11) and elapse of the time period (76), the third valve pressure relief element (72) can be operated to return the external ear canal pressure (10) toward the ambient pressure (11). The operation can be repeated to administer a pulsatile change in the external ear canal pressure (10).

As to particular embodiments, the external ear canal pressure regulation device (1) can further include a housing (80) having a housing internal surface defining a generally hollow internal space in which components of the external ear canal pressure regulation device (1) can be housed. As to particular embodiments, the housing (80) can be configured to fill a concha area (82) of the ear (35), whether in whole or in part, without extending any substantial distance outside of the external auditory meatus (24), thereby providing a discrete, unobtrusive, portable configuration which can be used upon occurrence to alleviate one or more disorder symptoms, for example neurologically-mediated pain, or treat one or more disorders, for example craniofacial pain syndromes or headache syndromes.

While the fluid flow generator (2) of the external ear canal pressure regulation device (1) above described typically delivers a fluid flow (8) of air to the external ear canal (6) to achieve the pressure differential (9) between the external ear canal pressure (10) and the ambient pressure (11), this is not intended to be limiting with respect to the wide variety of fluids which can be delivered to the external ear canal (6) by the external ear canal pressure regulation device (1). As illustrative examples, the wide variety of fluids can include: a purified gas, such as oxygen, nitrogen, argon, or the like; a mixture of partial pressures of gases; a liquid, such as water, oil, alcohol, or the like; or combinations thereof.

Additionally, while the fluid flow (8) or the transfer of a fluid volume (12) between components of the external ear canal pressure regulation device (1), between components of the external ear canal pressure regulation device (1) and the external ear canal (6), or between components of the external ear canal pressure regulation device (1) and the ambient pressure (11) can be above described as typically between a first point and a second point for the purpose of brevity, the fluid flow (8) or the transfer of the fluid volume (12) includes all points within the manifold fluid flow path (62) between the first point and the second point. For example, a fluid volume (12) transferred from the fluid flow generator (2) to the external ear canal (6) can travel along a fluid flow path (62) including the fluid flow generator (2), the first fluid flow conduit first end (50), the first portion (53) of the first fluid flow conduit (49), the first valve (52), the second portion (54) of the first fluid flow conduit (49), the first fluid flow conduit second end (51), the earpiece first end (31), the axial earpiece bore (4), the earpiece second end (29), and the external ear canal (6).

A method of producing particular embodiments of the external ear canal pressure regulation device (1) can include providing a fluid flow generator (2) capable of generating a fluid flow (8); providing a valved conduit (5) capable of fluidicly coupling to the fluid flow generator (2), the valved conduit (5) having a first fluid flow conduit (49); providing a first valve (52) capable of interrupting the first fluid flow conduit (49) to unidirectionally regulate the fluid flow (8) in the first fluid flow conduit (49); and providing an axial earpiece bore (4), which communicates between an earpiece first end (31) and an earpiece second end (32) of an earpiece (3), the axial earpiece bore (4) capable of fluidicly coupling to the valved conduit (5) opposite the fluid flow generator (2), the earpiece (3) having a compliant earpiece external surface (7) configured to sealably engage an external ear canal (6) as a barrier between an external ear canal pressure (10) and an ambient pressure (11).

The method of producing particular embodiments of the external ear canal pressure regulation device (1) can further include providing a fluid flow generator (2) having a configuration capable of generating the fluid flow (8) having a fluid volume (12) in a range of between 0 milliliters to about 20 milliliters. As to particular embodiments, the fluid volume (12) can have a pre-selected fluid volume (12), which can be selected from one or more of the group including or consisting of: between 0 milliliters to about 2 milliliters, between about 1 milliliter to about 3 milliliters, between about 2 milliliters to about 4 milliliters, between about 3 milliliters to about 5 milliliters, between about 4 milliliters to about 6 milliliters, between about 5 milliliters to about 7 milliliters, between about 6 milliliters to about 8 milliliters, between about 7 milliliters to about 9 milliliters, between about 8 milliliters to about 10 milliliters, between about 9 milliliters to about 11 milliliters, between about 10 milliliters to about 12 milliliters, between about 11 milliliters to about 13 milliliters, between about 12 milliliters to about 14 milliliters, between about 13 milliliters to about 15 milliliters, between about 14 milliliters to about 16 milliliters, between about 15 milliliters to about 17 milliliters, between about 16 milliliters to about 18 milliliters, between about 17 milliliters to about 19 milliliters, and between about 18 milliliters to about 20 milliliters.

The method of producing particular embodiments of the external ear canal pressure regulation device (1) can further include providing the valved conduit (5) having a configuration capable of removably coupling to the fluid flow generator (2) and the earpiece (3). As to particular embodiments, the method can further include providing the valved conduit (5) having a configuration capable of coupling in a first configuration (45) with the fluid flow generator (2) and the earpiece (3) to unidirectionally regulate the fluid flow (8) in a first direction (47) in the first fluid flow conduit (49). As to other particular embodiments, the method can further include providing the valved conduit (5) having a configuration capable of coupling in a second configuration (46) with the fluid flow generator (2) and the earpiece (3) to unidirectionally regulate the fluid flow (8) in a second direction (48) in the first fluid flow conduit (49).

The method of producing particular embodiments of the external ear canal pressure regulation device (1) can further include providing the first valve (52) having a configuration capable of dividing the first fluid flow conduit (49) into a first portion (53) proximate a first fluid flow conduit first end (50) and a second portion (54) proximate a first fluid flow conduit second end (51), and further comprising providing a second fluid flow conduit (55) having a configuration capable of fluidicly coupling between the first portion (53) of the first fluid flow conduit (49) and the ambient pressure (11), and further comprising providing a second valve (56) having a configuration capable of interrupting the second fluid flow conduit (55) to unidirectionally regulate the fluid flow (8) in the second fluid flow conduit (55).

The method of producing particular embodiments of the external ear canal pressure regulation device (1) can further include providing the fluid flow generator (2) configured as a volumetrically adjustable element (13) having an internal volume (19), the volumetrically adjustable element (13) having a deformed condition (20) which decreases the internal volume (19) to generate the fluid flow (8) in the first fluid flow conduit (49), the first valve (52) unidirectionally regulating the fluid flow (8) to egress from the axial earpiece bore (4) of the earpiece (3). As to particular embodiments, the volumetrically adjustable element (13) can return to a non-deformed condition (21) which increases the internal volume (19) to generate the fluid flow (8) in the second fluid flow conduit (55), the second valve (56) unidirectionally regulating the fluid flow (8) to ingress from the ambient pressure (11) toward the volumetrically adjustable element (13), the first valve (52) interrupting the fluid flow (8) in the first fluid flow conduit (49) from the second portion (54) toward the first portion (53).

The method of producing particular embodiments of the external ear canal pressure regulation device (1) can further include providing the fluid flow generator (2) configured as a volumetrically adjustable element (13) having an internal volume (19), the volumetrically adjustable element (13) having a deformed condition (20) which decreases the internal volume (19) to generate the fluid flow (8) in the second fluid flow conduit (55), the second valve (52) unidirectionally regulating the fluid flow (8) to egress from the second fluid flow conduit (55) toward the ambient pressure (11). As to particular embodiments, the volumetrically adjustable element (13) can return to a non-deformed condition (21) which increases the internal volume (19) to generate the fluid flow (8) in the first fluid flow conduit (49), the first valve (52) unidirectionally regulating the fluid flow (8) to ingress from the axial earpiece bore (4) of the earpiece (3) toward the volumetrically adjustable element (13), the second valve (56) interrupting the fluid flow (8) in the second fluid flow conduit (55) from the ambient pressure (11) toward the first portion (53).

The method of producing particular embodiments of the external ear canal pressure regulation device (1) can further include providing a third fluid flow conduit (57) having a configuration capable of fluidicly coupling between the second portion (54) of the first fluid flow conduit (49) and the ambient pressure (11), and further comprising providing a third valve (58) having a configuration capable of interrupting the third fluid flow conduit (57) to unidirectionally regulate the fluid flow (8) in the third fluid flow conduit (57). As to particular embodiments, the method can further include providing the third valve (58) having a configuration capable of regulating the fluid flow (8) to egress to the ambient pressure (11). As to other particular embodiments, the method of producing particular embodiments of the external ear canal pressure regulation device (1) can further include providing the third valve (58) having a configuration capable of regulating the fluid flow (8) to ingress from the ambient pressure (11).

The method of producing particular embodiments of the external ear canal pressure regulation device (1) can further include providing the third valve (58) having a configuration capable of interrupting the fluid flow (8) between the second portion (54) of the first fluid flow conduit (49) and the ambient pressure (11) until a pressure differential (9) between the second portion (54) of the first fluid conduit (49) and the ambient pressure (11) exceeds a pre-selected pressure differential (9) having a pressure differential amplitude (59) of between 0 kilopascals to about 50 kilopascals. As to particular embodiments, the one or more pre-selected pressure differential amplitudes (59) can be selected from the group including or consisting of: between 0 kilopascals to about 5 kilopascals, between about 2.5 kilopascals to about 7.5 kilopascals, between about 5 kilopascals to about 10 kilopascals, between about 7.5 kilopascals to about 12.5 kilopascals, between about 10 kilopascals to about 15 kilopascals, between about 12.5 kilopascals to about 17.5 kilopascals, between about 15 kilopascals to about 20 kilopascals, between about 17.5 kilopascals to about 22.5 kilopascals, between about 20 kilopascals to about 25 kilopascals, between about 22.5 kilopascals to about 27.5 kilopascals, between about 25 kilopascals to about 30 kilopascals, between about 27.5 kilopascals to about 32.5 kilopascals, between about 30 kilopascals to about 35 kilopascals, between about 32.5 kilopascals to about 37.5 kilopascals, between about 35 kilopascals to about 40 kilopascals, between about 37.5 kilopascals to about 42.5 kilopascals, between about 40 kilopascals to about 45 kilopascals, between about 42.5 kilopascals to about 47.5 kilopascals, and between about 45 kilopascals to about 50 kilopascals.

The method of producing particular embodiments of the external ear canal pressure regulation device (1) can further include providing a second valve pressure relief element (71) having a configuration capable of coupling to the second valve (56) and a third valve pressure relief element (72) having a configuration capable of coupling to the third valve (58), each one manually operable to correspondingly generate the fluid flow (8) in the second or third fluid flow conduits (55)(57).

The method of producing particular embodiments of the external ear canal pressure regulation device (1) can further include providing the valved conduit (5) having a configuration capable of coupling to the fluid flow generator (2) and the earpiece (3) in a first configuration (45) to unidirectionally regulate the fluid flow (8) in a first direction (47) in the first fluid flow conduit (49) to egress from the axial earpiece bore (4) of the earpiece (3). As to particular embodiments, the method can further include providing the fluid flow generator (2) configured as a volumetrically adjustable element (13) operable from a non-deformed condition (21) toward a deformed condition (20) to generate the fluid flow (2) which egresses from the axial earpiece bore (4) over a time period (76).

The method of producing particular embodiments of the external ear canal pressure regulation device (1) can further include providing the fluid flow generator (2) having a configuration capable of repeated operation from the non-deformed condition (21) toward the deformed condition (20) to generate the fluid flow (8) having a pressure wave (78) including a pressure wave amplitude (77) and a pressure wave frequency (79). As to particular embodiments, the pressure wave frequency (79) can be in a range of between 0 Hertz to about 10 Hertz. As to particular embodiments, one or more pressure wave frequencies (79) can be selected from the group including or consisting of: between 0 Hertz to about 1 Hertz, between about 0.5 Hertz to about 1.5 Hertz, between about 1 Hertz to about 2 Hertz, between about 1.5 Hertz to about 2.5 Hertz, between about 2 Hertz to about 3 Hertz, between about 2.5 Hertz to about 3.5 Hertz, between about 3 Hertz to about 4 Hertz, between about 3.5 Hertz to about 4.5 Hertz, between about 4 Hertz to about 5 Hertz, between about 4.5 Hertz to about 5.5 Hertz, between about 5 Hertz to about 6 Hertz, between about 5.5 Hertz to about 6.5 Hertz, between about 6 Hertz to about 7 Hertz, between about 6.5 Hertz to about 7.5 Hertz, between about 7 Hertz to about 8 Hertz, between about 7.5 Hertz to about 8.5 Hertz, between about 8 Hertz to about 9 Hertz, between about 8.5 Hertz to about 9.5 Hertz, and between about 9 Hertz to about 10 Hertz.

The method of producing particular embodiments of the external ear canal pressure regulation device (1) can further include providing a third valve pressure relief element (72) having a configuration capable of coupling to the third valve (56), whereby the fluid flow generator (2) and the third valve pressure relief element (72) can be capable of alternate repeated operation to generate the fluid flow (2) having the pressure wave (78) including the pressure wave amplitude (77) and the pressure wave frequency (79).

The method of producing particular embodiments of the external ear canal pressure regulation device (1) can further include providing the valved conduit (5) having a configuration capable of coupling to the fluid flow generator (2) and the earpiece (3) in a second configuration (46) to unidirectionally regulate the fluid flow (8) in a second direction (48) in the first fluid flow conduit (49) to ingress to the axial earpiece bore (4) of the earpiece (3). As to particular embodiments, the method can further include providing the fluid flow generator (2) configured as a volumetrically adjustable element (13) operable from a deformed condition (20) toward a non-deformed condition (21) to generate the fluid flow (2) which ingresses from the axial earpiece bore (4) over a time period (76).

The method of producing particular embodiments of the external ear canal pressure regulation device (1) can further include providing the fluid flow generator (2) having a configuration capable of repeated operation from the deformed condition (20) toward the non-deformed condition (21) to generate the fluid flow (8) having a pressure wave (78) including a pressure wave amplitude (77) and a pressure wave frequency (79). As to particular embodiments, the pressure wave frequency (79) can be in a range of between 0 Hertz to about 10 Hertz. As to particular embodiments, one or more pressure wave frequencies (79) can be selected from the group including or consisting of: between 0 Hertz to about 1 Hertz, between about 0.5 Hertz to about 1.5 Hertz, between about 1 Hertz to about 2 Hertz, between about 1.5 Hertz to about 2.5 Hertz, between about 2 Hertz to about 3 Hertz, between about 2.5 Hertz to about 3.5 Hertz, between about 3 Hertz to about 4 Hertz, between about 3.5 Hertz to about 4.5 Hertz, between about 4 Hertz to about 5 Hertz, between about 4.5 Hertz to about 5.5 Hertz, between about 5 Hertz to about 6 Hertz, between about 5.5 Hertz to about 6.5 Hertz, between about 6 Hertz to about 7 Hertz, between about 6.5 Hertz to about 7.5 Hertz, between about 7 Hertz to about 8 Hertz, between about 7.5 Hertz to about 8.5 Hertz, between about 8 Hertz to about 9 Hertz, between about 8.5 Hertz to about 9.5 Hertz, and between about 9 Hertz to about 10 Hertz.

The method of producing particular embodiments of the external ear canal pressure regulation device (1) can further include providing a third valve pressure relief element (72) having a configuration capable of coupling to the third valve (56), whereby the fluid flow generator (2) and the third valve pressure relief element (72) can be capable of alternate repeated operation to generate the fluid flow (2) having the pressure wave (78) including the pressure wave amplitude (77) and the pressure wave frequency (79).

As to particular embodiments, components of the external ear canal pressure regulation device (1) can be entirely formed of the same material, or alternatively, various components of the external ear canal pressure regulation device (1) can be formed from different materials. Additionally, as to particular embodiments, the external ear canal pressure regulation device (1) or components of the external ear canal pressure regulation device (1) can be produced from any of a wide variety of processes depending upon the application, such as press molding, injection molding, fabrication, machining, printing, three-dimensional printing, or the like, or combinations thereof, as one piece or assembled from a plurality of pieces into an embodiment of the external ear canal pressure regulation device (1) or provided as a plurality of pieces for assembly into an embodiment of the external ear canal pressure regulation device (1).

Components of the external ear canal pressure regulation device (1) can be produced from any of a wide variety of materials which can provide an embodiment of the external ear canal pressure regulation device (1) useful to generate and regulate a fluid flow (1). By way of non-limiting example, the valved conduit (1) can be produced from a variety of elastomeric compounds, plastic, plastic-like material, acrylic, polyamide, polyester, polypropylene, polyvinyl chloride-based materials, silicone-based materials, or the like, or combinations thereof.

A method of using a particular embodiment of the external ear canal pressure regulation device (1) can include obtaining the external ear canal pressure regulation (1) device including a fluid flow generator (2) which generates a fluid flow; a valved conduit (5) fluidicly coupled to the fluid flow generator (2), the valved conduit (5) having a first fluid flow conduit (49) interruptible by a first valve (52) to unidirectionally regulate the fluid flow (8) in the first fluid flow conduit (49); and an earpiece (3) having an axial earpiece bore (4) which communicates between an earpiece first end (31) and an earpiece second end (29), the axial earpiece bore (4) fluidicly coupled to the valved conduit (5) opposite the fluid flow generator (2), the earpiece (3) having a compliant earpiece external surface (7) configured to sealably engage an external ear canal (6) as a barrier between an external ear canal pressure (10) and an ambient pressure (11); sealably engaging the earpiece external surface (7) of the earpiece (3) with the external ear canal (6); generating the fluid flow (8) between the fluid flow generator (2) and the axial earpiece bore (4); and regulating a pressure differential (9) between the external ear canal pressure (10) and the ambient pressure (11).

As to particular embodiments, a method of using the external ear canal pressure regulation device (1) can include obtaining the external ear canal pressure regulation device (1) including a fluid flow generator (2) which generates a fluid flow (8); a valved conduit (5) having a first fluid flow conduit (49) interruptible by a first valve (52) to unidirectionally regulate the fluid flow (8) in the first fluid flow conduit (49); and an earpiece (3) having an axial earpiece bore (4) which communicates between an earpiece first end (31) and an earpiece second end (29), the earpiece (3) having a compliant earpiece external surface (7) configured to sealably engage an external ear canal (6) as a barrier between an external ear canal pressure (10) and an ambient pressure (11); fluidicly coupling the valved conduit (5) in a first configuration (45) with the fluid flow generator (2) and the axial earpiece bore (4) of the earpiece (3) to unidirectionally regulate the fluid flow (8) in a first direction (47) in the first fluid flow conduit (49); sealably engaging the earpiece external surface (7) of the earpiece (3) with the external ear canal (6); generating the fluid flow (8) between the fluid flow generator (2) and the axial earpiece bore (4) in the first direction (47) in the first fluid flow conduit (49); and regulating a pressure differential (9) between the external ear canal pressure (10) and the ambient pressure (11) wherein the external ear canal pressure (10) is greater than the ambient pressure (11).

As to particular embodiments, the method of using the external ear canal pressure regulation device (1) can further include operating a pressure relief element (70) to generate the fluid flow (8) from the external ear canal (6) toward the ambient pressure (11) to return the external ear canal pressure (10) toward the ambient pressure (11). As to particular embodiments, the method can further include disengaging the earpiece external surface (7) of the earpiece (3) from the external ear canal (6).

As to particular embodiments, the method of using the external ear canal pressure regulation device (1) can further include uncoupling the valved conduit (5) in the first configuration (45) from the fluid flow generator (2) and the axial earpiece bore (4) of the earpiece (3).

As to particular embodiments, the method of using the external ear canal pressure regulation device (1) can further include fluidicly coupling the valved conduit (5) in a second configuration (46) with the fluid flow generator (2) and the axial earpiece bore (4) of the earpiece (3) to unidirectionally regulate the fluid flow (8) in a second direction (48) in the first fluid flow conduit (49); sealably engaging the earpiece external surface (7) of the earpiece (3) with the external ear canal (7); generating the fluid flow (8) between the fluid flow generator (2) and the axial earpiece bore (4) in the second direction (48) in the first fluid flow conduit (49); and regulating a pressure differential (9) between the external ear canal pressure (10) and the ambient pressure (11) wherein the external ear canal pressure (10) is lesser than the ambient pressure (11).

As to particular embodiments, the method of using the external ear canal pressure regulation device (1) can further include operating a pressure relief element (70) to generate the fluid flow (8) from the ambient pressure (11) toward the external ear canal (6) to return the external ear canal pressure (10) toward the ambient pressure (11). As to particular embodiments, the method can further include disengaging the earpiece external surface (7) of the earpiece (3) from the external ear canal (6).

As to particular embodiments, the method of using the external ear canal pressure regulation device (1) can further include uncoupling the valved conduit (5) in the second configuration (46) from the fluid flow generator (2) and the axial earpiece bore (4) of the earpiece (3).

As can be easily understood from the foregoing, the basic concepts of the present invention may be embodied in a variety of ways. The invention involves numerous and varied embodiments of an external ear canal pressure regulation device and methods for making and using such external ear canal pressure regulation devices including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "fluid flow" should be understood to encompass disclosure of the act of "flowing fluid"—whether explicitly discussed or not—and, conversely, were there effectively disclosure of the act of "flowing fluid", such a disclosure should be understood to encompass disclosure of a "fluid flow" and even a "means for flowing fluid." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the external ear canal pressure regulation devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method for alleviating a user's headache pain, the method comprising:

sealably engaging an earpiece of a fluid transfer device with an ear of the user as a barrier between an external ear canal pressure of an external ear canal of the user and an ambient pressure outside the external ear canal; and operating a fluid flow generator of the fluid transfer device to generate a fluid flow between the earpiece and the external ear canal, operating the fluid flow generator comprises at least one of:

operating the fluid flow generator in a first configuration to increase the external ear canal pressure relative to the ambient pressure so as to generate a positive external ear canal pressure differential between the external ear canal pressure and the ambient pressure, or operating the fluid flow generator in a second configuration to decrease the external ear canal pressure relative to the ambient pressure so as to generate a negative external ear canal pressure differential between the external ear canal pressure and the ambient pressure, wherein at least one of the positive external ear canal pressure differential or the negative external ear canal pressure differential causes a physiological response that alleviates the headache pain.

2. The method of claim 1, wherein operating the fluid flow generator comprises operating the fluid flow generator in the first configuration to increase the external ear canal pressure relative to the ambient pressure so as to generate the positive external ear canal pressure differential between the external ear canal pressure and the ambient pressure.

3. The method of claim 2, wherein operating the fluid flow generator further comprises operating the fluid flow generator in the second configuration to decrease the external ear canal pressure relative to the ambient pressure so as to generate the negative external ear canal pressure differential between the external ear canal pressure and the ambient pressure.

4. The method of claim 1, wherein operating the fluid flow generator comprises operating the fluid flow generator in the second configuration to decrease the external ear canal pressure relative to the ambient pressure so as to generate the negative external ear canal pressure differential between the external ear canal pressure and the ambient pressure.

5. The method of claim 1, wherein the fluid flow generator comprises a valve.

6. The method of claim 5, wherein the fluid flow generator is in the first configuration when the valve is in a first position, and wherein the fluid flow generator is in the second configuration when the valve is in a second position.

7. The method of claim 5, wherein the valve comprises a unidirectional valve.

8. The method of claim 1, wherein at least one of the positive external ear canal pressure differential or the negative external ear canal pressure differential is configured to move a tympanic membrane of the ear.

9. The method of claim 1, wherein operating the fluid flow generator further comprises generating the fluid flow having a pressure wave.

10. The method of claim 9, wherein the pressure wave comprises a pressure wave amplitude and a pressure wave frequency.

11. A method for alleviating a user's headache pain, the method comprising:

engaging a fluid transfer device with an ear of the user as a barrier between an external ear canal pressure of an external ear canal of the user and an ambient pressure outside the external ear canal, the fluid transfer device comprising:

a fluid flow generator, and
a valved conduit in fluid communication with the fluid flow generator; and
operating the fluid transfer device to generate a fluid flow between the fluid transfer device and the external ear canal, operating the fluid transfer device comprises at least one of:
operating the fluid flow generator when the valved conduit is in a first configuration to increase the external ear canal pressure relative to the ambient pressure so as to generate a positive external ear canal pressure differential between the external ear canal pressure and the ambient pressure, or
operating the fluid flow generator when the valved conduit is in a second configuration to decrease the external ear canal pressure relative to the ambient pressure so as to generate a negative external ear canal pressure differential between the external ear canal pressure and the ambient pressure,
wherein at least one of the positive external ear canal pressure differential or the negative external ear canal pressure differential causes a physiological response that alleviates the headache pain.

12. The method of claim 11, wherein operating the fluid transfer device comprises operating the fluid flow generator when the valved conduit is in the first configuration to increase the external ear canal pressure relative to the ambient pressure so as to generate the positive external ear canal pressure differential between the external ear canal pressure and the ambient pressure.

13. The method of claim 12, wherein operating the fluid transfer device further comprises operating the fluid flow generator when the valved conduit is in the second configuration to decrease the external ear canal pressure relative to the ambient pressure so as to generate the negative external ear canal pressure differential between the external ear canal pressure and the ambient pressure.

14. The method of claim 11, wherein operating the fluid transfer device comprises operating the fluid flow generator when the valved conduit is in the second configuration to decrease the external ear canal pressure relative to the ambient pressure so as to generate the negative external ear canal pressure differential between the external ear canal pressure and the ambient pressure.

15. The method of claim 11, wherein the fluid transfer device comprises an earpiece.

16. The method of claim 15, wherein engaging the fluid transfer device with the ear comprises sealably engaging the earpiece with the external ear canal of the user.

17. The method of claim 11, wherein the headache pain comprises a migraine headache pain.

18. The method of claim 11, wherein at least one of the positive external ear canal pressure differential or the negative external ear canal pressure differential is configured to move a tympanic membrane of the user.

19. The method of claim 11, wherein operating the fluid transfer device further comprises generating the fluid flow having a pressure wave.

20. The method of claim 19, wherein the pressure wave comprises a pressure wave amplitude and a pressure wave frequency.

* * * * *